US012378299B2

(12) United States Patent
Song et al.

(10) Patent No.: US 12,378,299 B2
(45) Date of Patent: Aug. 5, 2025

(54) CD80 VARIANT PROTEINS AND USES THEREOF

(71) Applicants: XUANZHU BIOPHARMACEUTICAL CO., LTD., Shijiazhuang (CN); BEIJING XUANZHU COMBIO CO., LTD., Beijing (CN)

(72) Inventors: Yuntao Song, Palo Alto, CA (US); Jianhui Zhou, Redwood City, CA (US); Yi Ding, Milpitas, CA (US); Ping Hui Szu, Walnut Creek, CA (US); Chen Dong, Cupertino, CA (US)

(73) Assignees: XUANZHU BIOPHARMACEUTICAL CO., LTD., Shijiazhuang (CN); BEIJING XUANZHU COMBIO CO., LTD., Beijing (CN)

( * ) Notice: Subject to any disclaimer, the term of this patent is extended or adjusted under 35 U.S.C. 154(b) by 954 days.

(21) Appl. No.: 17/606,577

(22) PCT Filed: Apr. 24, 2020

(86) PCT No.: PCT/US2020/029834
§ 371 (c)(1),
(2) Date: Oct. 26, 2021

(87) PCT Pub. No.: WO2020/219896
PCT Pub. Date: Oct. 29, 2020

(65) Prior Publication Data
US 2022/0227833 A1 Jul. 21, 2022

Related U.S. Application Data

(60) Provisional application No. 62/839,542, filed on Apr. 26, 2019.

(51) Int. Cl.
*C07K 14/705* (2006.01)
*A61K 38/00* (2006.01)
*A61P 35/00* (2006.01)

(52) U.S. Cl.
CPC ........ *C07K 14/70532* (2013.01); *A61P 35/00* (2018.01); *A61K 38/00* (2013.01); *C07K 2319/30* (2013.01)

(58) Field of Classification Search
CPC .............................................. C07K 14/70532
See application file for complete search history.

(56) References Cited

U.S. PATENT DOCUMENTS

| 11,639,375 B2 * | 5/2023 | Swanson ................. A61P 35/00 424/134.1 |
| 2011/0002956 A1 | 1/2011 | Weiner et al. |
| 2015/0232532 A1 | 8/2015 | Ostrand-Rosenberg |
| 2018/0244759 A1 | 8/2018 | Anderson et al. |

FOREIGN PATENT DOCUMENTS

| CN | 109475628 A | 3/2019 |
| JP | 2018502550 A | 2/2018 |
| WO | WO-2002000717 A2 | 1/2002 |
| WO | 2004029197 A2 | 4/2004 |
| WO | WO-2017181152 A2 | 10/2017 |

OTHER PUBLICATIONS

"Both Extracellular Immunoglobulin-like Domains of CD80 Contains Residues Critical for Binding T Cell Surface Receptors CTLA-4 and CD28", Peach et al, The Journal of Biological Chemistry (Year: 1995).*
International Search Report and Written Opinion of the International Searching Authority, issued in PCT/US2020/029834, mailed Oct. 5, 2020; ISA/US.
Wang, Y.G., and Huang, F., "Targeting Cancer Therapy of Adeno-associated Virus Vector," Chinese Journal of Cell Biology, 29: 651-656 (2007)—Abstract only.
Peach, R.J., et al., "Both Extracellular Immunoglobin-like Domains of CD80 Contain Residues Critical for Binding T Cell Surface Receptors CTLA-4 and CD28*," Journal of Biological Chemistry, American Society for Biochemistry and Molecular Biology, 270(36): 21181-21187 (1995).
Guo, Y., et al., "Identification of conserved amino acids in murine B7-1IgV domain critical for CTLA4/CD28:B7 interaction by site-directed mutagenesis: a novel structural model of the binding site," Molecular Immunology, 35: 215-225 (1998).
Fargeas, C.A., et al., "Identification of Residues in the V Domain of CD80 (B7-1) Implicated in Functional Interactions with CD28 and CTLA4," J. Exp. Med., 182: 667-675 (1995).
Office Action from corresponding Australian Application No. 2020262424 dated Oct. 10, 2022.
Decision for Allowance from Korean Application No. 10-2021-7038749 dated Dec. 30, 2024.

* cited by examiner

*Primary Examiner* — Janet L Epps-Smith
*Assistant Examiner* — Nada Ahmed Mahmou Elmansy
(74) *Attorney, Agent, or Firm* — Harness Dickey & Pierce P.L.C.

(57) ABSTRACT

The present disclosure provides variant CD80 polypeptides that have altered affinity for their cognate binding partners, and immunomodulatory fusion proteins comprising the variant CD80 polypeptides. The present disclosure also provides pharmaceutical compositions comprising such polypeptides and/or proteins and methods for modulating immune responses and/or treatment of cancer, infectious diseases, and/or immunological diseases.

10 Claims, 37 Drawing Sheets

Specification includes a Sequence Listing.

FIG. 1. Wild-type Human CD80 Extracellular Domain (ECD) (CD80_Human: UniProtKB – P33681)

```
            10         20         30         40         50
     VIHVTKEVKE VATLSCGHNV SVEELAQTRI YWQKEKKMVL TMMSGDMNIW
            60         70         80         90        100
     PEYKNRTIFD ITNNLSIVIL ALRPSDEGTY ECVVLKYEKD AFKREHLAEV
           110        120        130        140        150
     TLSVKADFPT PSISDFEIPT SNIRRIICST SGGFPEPHLS WLENGEELNA
           160        170        180        190        200
     INTTVSQDPE TELYAVSSKL DFNMTTNHSF MCLIKYGHLR VNQTFNWNTT
           208
     KQEHFPDN    (SEQ ID NO:1)
```

FIG. 2. Human IgG1 Fc (IGHG1_HUMAN: UniProKB – P01857)

```
           110        120        130        140        150
       DKTHTCP PCPAPELLGG PSVFLFPPKP KDTLMISRTP EVTCVVVDVS
           160        170        180        190        200
    HEDPEVKFNW YVDGVEVHNA KTKPREEQYN STYRVVSVLT VLHQDWLNGK
           210        220        230        240        250
    EYKCKVSNKA LPAPIEKTIS KAKGQPREPQ VYTLPPSRDE LTKNQVSLTC
           260        270        280        290        300
    LVKGFYPSDI AVEWESNGQP ENNYKTTPPV LDSDGSFFLY SKLTVDKSRW
           310        320        330
    QQGNVFSCSV MHEALHNHYT QKSLSLSPGK  (SEQ ID NO:2)
```

FIG. 3. Human IgG2 Fc (IGHG2_HUMAN: UniProKB – P01859)

```
           110        120        130        140        150
        VECPPCP APPVAGPSVF LFPPKPKDTL MISRTPEVTC VVVDVSHEDP
           160        170        180        190        200
    EVQFNWYVDG VEVHNAKTKP REEQFNSTFR VVSVLTVVHQ DWLNGKEYKC
           210        220        230        240        250
    KVSNKGLPAP IEKTISKTKG QPREPQVYTL PPSREEMTKN QVSLTCLVKG
           260        270        280        290        300
    FYPSDISVEW ESNGQPENNY KTTPPMLDSD GSFFLYSKLT VDKSRWQQGN
           310        320
    VFSCSVMHEA LHNHYTQKSL SLSPGK  (SEQ ID NO:3)
```

FIG. 4. Human IgG3 Fc (IGHG3_HUMAN: UniProKB – P01860)

```
            160        170        180        190        200
     DTPPPCPRCP APELLGGPSV FLFPPKPKDT LMISRTPEVT CVVVDVSHED
            210        220        230        240        250
     PEVQFKWYVD GVEVHNAKTK PREEQYNSTF RVVSVLTVLH QDWLNGKEYK
            260        270        280        290        300
     CKVSNKALPA PIEKTISKTK GQPREPQVYT LPPSREEMTK NQVSLTCLVK
            310        320        330        340        350
     GFYPSDIAVE WESSGQPENN YNTTPPMLDS DGSFFLYSKL TVDKSRWQQG
            360        370
     NIFSCSVMHE ALHNRFTQKS LSLSPGK    (SEQ ID NO:4)
```

FIG. 5. Human IgG4 Fc (IGHG4_HUMAN: UniProKB – P01861)

```
            110        120        130        140        150
     KYGPPCPSCP APEFLGGPSV FLFPPKPKDT LMISRTPEVT CVVVDVSQED
            160        170        180        190        200
     PEVQFNWYVD GVEVHNAKTK PREEQFNSTY RVVSVLTVLH QDWLNGKEYK
            210        220        230        240        250
     CKVSNKGLPS SIEKTISKAK GQPREPQVYT LPPSQEEMTK NQVSLTCLVK
            260        270        280        290        300
     GFYPSDIAVE WESNGQPENN YKTTPPVLDS DGSFFLYSRL TVDKSRWQEG
            310        320
     NVFSCSVMHE ALHNHYTQKS LSLSLGK    (SEQ ID NO:5)
```

FIG. 6. Mouse IgG1 Fc (IGHG1_MOUSE, Ig gamma-1 chain C region secreted from: UniProKB – P01868)

```
            110        120        130        140        150
          KPCICT VPEVSSVFIF PPKPKDVLTI TLTPKVTCVV VDISKDDPEV
            160        170        180        190        200
     QFSWFVDDVE VHTAQTQPRE EQFNSTFRSV SELPIMHQDW LNGKEFKCRV
            210        220        230        240        250
     NSAAFPAPIE KTISKTKGRP KAPQVYTIPP PKEQMAKDKV SLTCMITDFF
            260        270        280        290        300
     PEDITVEWQW NGQPAENYKN TQPIMNTNGS YFVYSKLNVQ KSNWEAGNTF
            310        320
     TCSVLHEGLH NHHTEKSLSH SPGK   (SEQ ID NO:6)
```

FIG. 7. Mouse IgG2a Fc (GCAA_MOUSE, Ig gamma-2A chain C region, A allele: UniProKB – P01863)

```
          110        120        130        140        150
   GPTIKPCPPC KCPAPNLLGG PSVFIFPPKI KDVLMISLSP IVTCVVVDVS
          160        170        180        190        200
   EDDPDVQISW FVNNVEVHTA QTQTHREDYN STLRVVSALP IQHQDWMSGK
          210        220        230        240        250
   EFKCKVNNKD LPAPIERTIS KPKGSVRAPQ VYVLPPPEEE MTKKQVTLTC
          260        270        280        290        300
   MVTDFMPEDI YVEWTNNGKT ELNYKNTEPV LDSDGSYFMY SKLRVEKKNW
          310        320        330
   VERNSYSCSV VHEGLHNHHT TKSFSRTPGK   (SEQ ID NO:7)
```

FIG. 8. Mouse IgG2b Fc (IGG2B_MOUSE, Ig gamma-2B chain C region: UniProKB – P01867)

```
          110        120        130        140        150
    STINPCPP CKECHKCPAP NLEGGPSVFI FPPNIKDVLM ISLTPKVTCV
          160        170        180        190        200
   VVDVSEDDPD VQISWFVNNV EVHTAQTQTH REDYNSTIRV VSTLPIQHQD
          210        220        230        240        250
   WMSGKEFKCK VNNKDLPSPI ERTISKIKGL VRAPQVYILP PPAEQLSRKD
          260        270        280        290        300
   VSLTCLVVGF NPGDISVEWT SNGHTEENYK DTAPVLDSDG SYFIYSKLNM
          310        320        330        340        350
   KTSKWEKTDS FSCNVRHEGL KNYYLKKTIS RSPGLDLDDI CAEAKDGELD
          360        370        380        390        400
   GLWTTITIFI SLFLLSVCYS ASVTLFKVKW IFSSVVELKQ KISPDYRNMI

GQGA   (SEQ ID NO:8)
```

FIG. 9. Mouse IgG3 Fc (IGHG3_MOUSE, Ig gamma-3 chain C region: UniProKB – P03987)

```
          110        120        130        140        150
     STPPGSS CPPGNILGGP SVFIFPPKPK DALMISLTPK VTCVVVDVSE
          160        170        180        190        200
   DDPDVHVSWF VDNKEVHTAW TQPREAQYNS TFRVVSALPI QHQDWMRGKE
          210        220        230        240        250
   FKCKVNNKAL PAPIERTISK PKGRAQTPQV YTIPPPREQM SKKKVSLTCL
          260        270        280        290        300
   VTNFFSEAIS VEWERNGELE QDYKNTPPIL DSDGTYFLYS KLTVDTDSWL
          310        320        330        340        350
   QGEIFTCSVV HEALHNHHTQ KNLSRSPELE LNETCAEAQD GELDGLWTTI
          360        370        380        390
   TIFISLFLLS VCYSASVTLF KVKWIFSSVV QVKQTAIPDY RNMIGQGA
    (SEQ ID NO:9)
```

FIG. 10. Human CD28 (CD28_HUMAN: UniProKB – P10747)

```
         10         20         30         40         50
 MLRLLLALNL FPSIQVTGNK ILVKQSPMLV AYDNAVNLSC KYSYNLFSRE
         60         70         80         90        100
 FRASLHKGLD SAVEVCVVYG NYSQQLQVYS KTGFNCDGKL GNESVTFYLQ
        110        120        130        140        150
 NLYVNQTDIY FCKIEVMYPP PYLDNEKSNG TIIHVKGKHL CPSPLFPGPS
        160        170        180        190        200
 KPFWVLVVVG GVLACYSLLV TVAFIIFWVR SKRSRLLHSD YMNMTPRRPG
        210        220
 PTRKHYQPYA PPRDFAAYRS  (SEQ ID NO:10)
```

FIG. 11. Human CTLA-4 (CTLA4_HUMAN: UniProKB – P16410)

```
         10         20         30         40         50
 MACLGFQRHK AQLNLATRTW PCTLLFFLLF IPVFCKAMHV AQPAVVLASS
         60         70         80         90        100
 RGIASFVCEY ASPGKATEVR VTVLRQADSQ VTEVCAATYM MGNELTFLDD
        110        120        130        140        150
 SICTGTSSGN QVNLTIQGLR AMDTGLYICK VELMYPPPYY LGIGNGTQIY
        160        170        180        190        200
 VIDPEPCPDS DFLLWILAAV SSGLFFYSFL LTAVSLSKML KKRSPLTTGV
        210        220
 YVKMPPTEPE CEKQFQPYFI PIN  (SEQ ID NO:11)
```

FIG. 12. Human PD-L1 (PD1L1_HUMAN: UniProKB – Q9NZQ7)

```
         10         20         30         40         50
 MRIFAVFIFM TYWHLLNAFT VTVPKDLYVV EYGSNMTIEC KFPVEKQLDL
         60         70         80         90        100
 AALIVYWEME DKNIIQFVHG EEDLKVQHSS YRQRARLLKD QLSLGNAALQ
        110        120        130        140        150
 ITDVKLQDAG VYRCMISYGG ADYKRITVKV NAPYNKINQR ILVVDPVTSE
        160        170        180        190        200
 HELTCQAEGY PKAEVIWTSS DHQVLSGKTT TTNSKREEKL FNVTSTLRIN
        210        220        230        240        250
 TTTNEIFYCT FRRLDPEENH TAELVIPELP LAHPPNERTH LVILGAILLC
        260        270        280        290
 LGVALTFIFR LRKGRMMDVK KCGIQDTNSK KQSDTHLEET  (SEQ ID NO:12)
```

FIG. 13A
FIG. 13B
Leader Sequence (Human IgG heavy chain GenBank: QBK47409.1)
MGWSCIILFLVATATGVHS (SEQ ID NO:13)
FIG. 13C
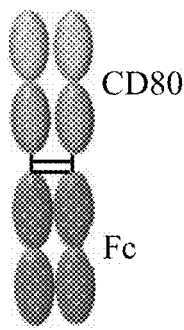
CD80-Fc Fusion Protein

FIG. 14A. Human CD80 + Human IgG1 Fc

```
        10         20         30         40         50
 VIHVTKEVKE VATLSCGHNV SVEELAQTRI YWQKEKKMVL TMMSGDMNIW
        60         70         80         90        100
 PEYKNRTIFD ITNNLSIVIL ALRPSDEGTY ECVVLKYEKD AFKREHLAEV
       110        120        130        140        150
 TLSVKADFPT PSISDFEIPT SNIRRIICST SGGFPEPHLS WLENGEELNA
       160        170        180        190        200
 INTTVSQDPE TELYAVSSKL DFNMTTNHSF MCLIKYGHLR VNQTFNWNTT
       210        220        230        240        250
 KQEHFPDNGS DKTHTCPPCP APELLGGPSV FLFPPKPKDT LMISRTPEVT
       260        270        280        290        300
 CVVVDVSHED PEVKFNWYVD GVEVHNAKTK PREEQYNSTY RVVSVLTVLH
       310        320        330        340        350
 QDWLNGKEYK CKVSNKALPA PIEKTISKAK GQPREPQVYT LPPSRDELTK
       360        370        380        390        400
 NQVSLTCLVK GFYPSDIAVE WESNGQPENN YKTTPPVLDS DGSFFLYSKL
       410        420        430        437
 TVDKSRWQQG NVFSCSVMHE ALHNHYTQKS LSLSPGK  (SEQ ID NO:14)
```

FIG. 14B

Wild type mouse CD80 sequence

MACNCQLMQDTPLLKFPCPRLILLFVLLIRLSQVSSDVDEQLSKSVKDKV
LLPCRYNSPHEDESEDRIYWQKHDKVVLSVIAGKLKVWPEYKNRTLYDNT
TYSLIILGLVLSDRGTYSCVVQKKERGTYEVKHLALVKLSIKADFSTPNI
TESGNPSADTKRITCFASGGFPKPRFSWLENGRELPGINTTISQDPESEL
YTISSQLDFNTTRNHTIKCLIKYGDAHVSEDFTWEKPPEDPPDSKNTLVL
FGAGFGAVITVVVIVVIIKCFCKHRSCFRRNEASRETNNSLTFGPEEALA
EQTVFL (SEQ ID NO:15)

Lane 1: Molecular Weight Marker
Lane 2: S131F, 1.5 ug/lane
Lane 3: S131R, 1.5 ug/lane
Lane 4: S131E, 2.0 ug/lane
Lane 5: S131D, 1.6 ug/lane
Lane 6: S131Q, 1.6 ug/lane
Lane 7: A165V, 1.2 ug/lane
Lane 8: A165I, 1.6 ug/lane
Lane 9: A165F, 1.6 ug/lane
Lane 10: A165R, 1.6 ug/lane
Lane 11: A165D, 1.6 ug/lane
Lane 12: A165Q, 1.6 ug/lane Lane 1: Molecular Weight Marker
Lane 2: S131F, 1.5 ug/lane
Lane 3: S131R, 1.5 ug/lane
Lane 4: S131E, 2.0 ug/lane
Lane 5: S131D, 1.6 ug/lane
Lane 6: S131Q, 1.6 ug/lane
Lane 7: A165V, 1.2 ug/lane
Lane 8: A165I, 1.6 ug/lane
Lane 9: A165F, 1.6 ug/lane
Lane 10: A165R, 1.6 ug/lane
Lane 11: A165D, 1.6 ug/lane
Lane 12: A165Q, 1.6 ug/lane Lane 1: Molecular Weight Marker
Lane 2: V166A, 10/lane
Lane 3: V166T, 10 ug/lane
Lane 4: V166L/L139V, 10 ug/lane
Lane 5: S156A/V155A, 10 ug/lane
Lane 6: S156A/V155I, 10 ug/lane
Lane 7: S156A/V155T, 10 ug/lane
Lane 8: S156A/T130A, 10 ug/lane
Lane 9: S156A/V166A, 10 ug/lane
Lane 10: S156A/V166L/L139V, 10 ug/lane Lane 1: Molecular Weight Marker
Lane 2: V166A, 10/lane
Lane 3: V166T, 10 ug/lane
Lane 4: V166L/L139V, 10 ug/lane
Lane 5: S156A/V155A, 10 ug/lane
Lane 6: S156A/V155I, 10 ug/lane
Lane 7: S156A/V155T, 10 ug/lane
Lane 8: S156A/T130A, 10 ug/lane
Lane 9: S156A/V166A, 10 ug/lane
Lane 10: S156A/V166L/L139V, 10 ug/lane

FIG. 15E        FIG. 15F
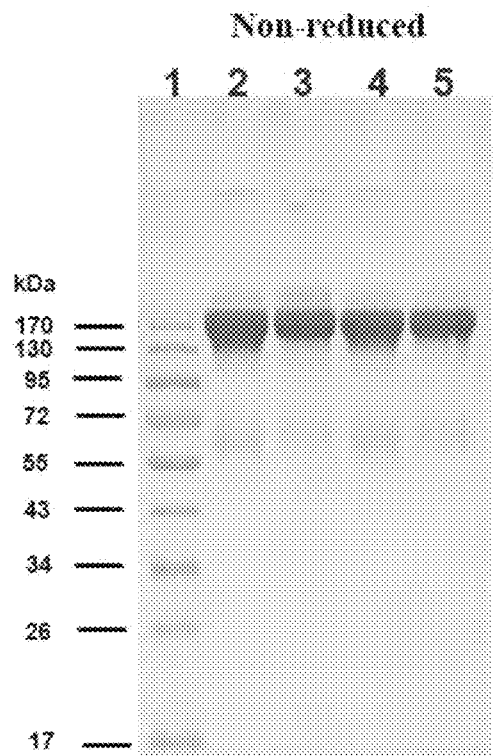
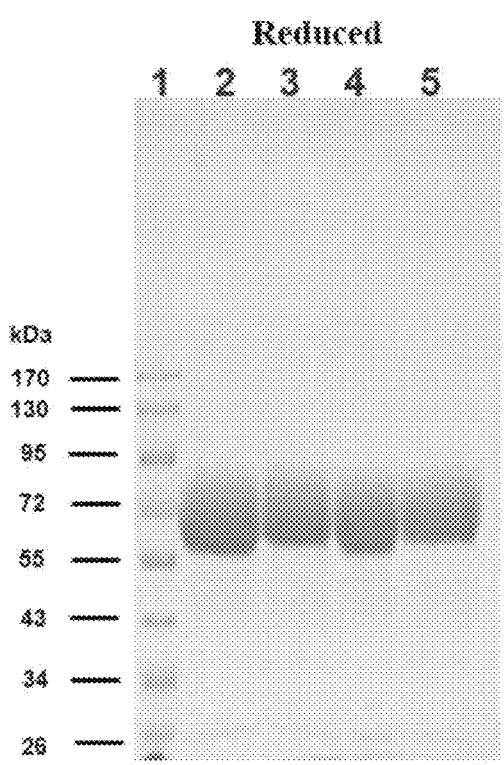
Lane 1: Molecular Weight Marker
Lane 2: S131V, 10 ug/lane
Lane 3: V155A, 10 ug/lane
Lane 4: V155I, 10 ug/lane
Lane 5: V155T, 10 ug/lane Crystal structure of human CD80 complexed with CTLA-4

***P<0.001, All groups compare to Vehicle group

```
                           SEQUENCE LISTING

<160> NUMBER OF SEQ ID NOS: 85

<210> SEQ ID NO 1
<211> LENGTH: 208
<212> TYPE: PRT
<213> ORGANISM: Homo sapiens

<400> SEQUENCE: 1

Val Ile His Val Thr Lys Glu Val Lys Glu Val Ala Thr Leu Ser Cys
1               5                  10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 2
<211> LENGTH: 227
<212> TYPE: PRT
<213> ORGANISM: Homo sapiens

<400> SEQUENCE: 2

Asp Lys Thr His Thr Cys Pro Pro Cys Pro Ala Pro Glu Leu Leu Gly
1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 3
<211> LENGTH: 223
<212> TYPE: PRT
<213> ORGANISM: Homo sapiens

<400> SEQUENCE: 3

Val Glu Cys Pro Pro Cys Pro Ala Pro Pro Val Ala Gly Pro Ser Val
1               5                   10                  15
Phe Leu Phe Pro Pro Lys Pro Lys Asp Thr Leu Met Ile Ser Arg Thr
                20                  25                  30
Pro Glu Val Thr Cys Val Val Val Asp Val Ser His Glu Asp Pro Glu
            35                  40                  45
Val Gln Phe Asn Trp Tyr Val Asp Gly Val Glu Val His Asn Ala Lys
        50                  55                  60
Thr Lys Pro Arg Glu Glu Gln Phe Asn Ser Thr Phe Arg Val Val Ser
65                  70                  75                  80
Val Leu Thr Val Val His Gln Asp Trp Leu Asn Gly Lys Glu Tyr Lys
                85                  90                  95
Cys Lys Val Ser Asn Lys Gly Leu Pro Ala Pro Ile Glu Lys Thr Ile
                100                 105                 110
Ser Lys Thr Lys Gly Gln Pro Arg Glu Pro Gln Val Tyr Thr Leu Pro
        115                 120                 125
Pro Ser Arg Glu Glu Met Thr Lys Asn Gln Val Ser Leu Thr Cys Leu
    130                 135                 140
Val Lys Gly Phe Tyr Pro Ser Asp Ile Ser Val Glu Trp Glu Ser Asn
145                 150                 155                 160
Gly Gln Pro Glu Asn Asn Tyr Lys Thr Thr Pro Pro Met Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Ser Leu Ser Pro Gly Lys
    210                 215                 220
```

<210> SEQ ID NO 4
<211> LENGTH: 227
<212> TYPE: PRT
<213> ORGANISM: Homo sapiens

<400> SEQUENCE: 4

```
Asp Thr Pro Pro Cys Pro Arg Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Gln Phe Lys Trp Tyr Val Asp Gly Val Glu Val
50                  55                  60

His Asn Ala Lys Thr Lys Pro Arg Glu Glu Gln Tyr Asn Ser Thr Phe
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Thr Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Ile Phe Ser Cys Ser Val Met
            195                 200                 205

His Glu Ala Leu His Asn Arg Phe Thr Gln Lys Ser Leu Ser Leu Ser
210                 215                 220

Pro Gly Lys
225
```

<210> SEQ ID NO 5
<211> LENGTH: 227
<212> TYPE: PRT
<213> ORGANISM: Homo sapiens

<400> SEQUENCE: 5

```
Lys Tyr Gly Pro Pro Cys Pro Ser Cys Pro Ala Pro Glu Phe Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser Gln
            35                  40                  45

Glu Asp Pro Glu Val Gln Phe Asn Trp Tyr Val Asp Gly Val Glu Val
50                  55                  60

His Asn Ala Lys Thr Lys Pro Arg Glu Glu Gln Phe Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Gly Leu Pro Ser Ser Ile
```

```
            100                 105                 110
Glu Lys Thr Ile Ser Lys Ala Lys Gly Gln Pro Arg Glu Pro Gln Val
        115                 120                 125

Tyr Thr Leu Pro Pro Ser Gln Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Arg Leu Thr Val
            180                 185                 190

Asp Lys Ser Arg Trp Gln Glu Gly Asn Val Phe Ser Cys Ser Val Met
        195                 200                 205

His Glu Ala Leu His Asn His Tyr Thr Gln Lys Ser Leu Ser Leu Ser
    210                 215                 220

Leu Gly Lys
225

<210> SEQ ID NO 6
<211> LENGTH: 220
<212> TYPE: PRT
<213> ORGANISM: Mus musculus

<400> SEQUENCE: 6

Lys Pro Cys Ile Cys Thr Val Pro Glu Val Ser Ser Val Phe Ile Phe
1               5                   10                  15

Pro Pro Lys Pro Lys Asp Val Leu Thr Ile Thr Leu Thr Pro Lys Val
            20                  25                  30

Thr Cys Val Val Val Asp Ile Ser Lys Asp Asp Pro Glu Val Gln Phe
        35                  40                  45

Ser Trp Phe Val Asp Asp Val Glu Val His Thr Ala Gln Thr Gln Pro
    50                  55                  60

Arg Glu Glu Gln Phe Asn Ser Thr Phe Arg Ser Val Ser Glu Leu Pro
65                  70                  75                  80

Ile Met His Gln Asp Trp Leu Asn Gly Lys Glu Phe Lys Cys Arg Val
                85                  90                  95

Asn Ser Ala Ala Phe Pro Ala Pro Ile Glu Lys Thr Ile Ser Lys Thr
            100                 105                 110

Lys Gly Arg Pro Lys Ala Pro Gln Val Tyr Thr Ile Pro Pro Pro Lys
        115                 120                 125

Glu Gln Met Ala Lys Asp Lys Val Ser Leu Thr Cys Met Ile Thr Asp
    130                 135                 140

Phe Phe Pro Glu Asp Ile Thr Val Glu Trp Gln Trp Asn Gly Gln Pro
145                 150                 155                 160

Ala Glu Asn Tyr Lys Asn Thr Gln Pro Ile Met Asn Thr Asn Gly Ser
                165                 170                 175

Tyr Phe Val Tyr Ser Lys Leu Asn Val Gln Lys Ser Asn Trp Glu Ala
            180                 185                 190

Gly Asn Thr Phe Thr Cys Ser Val Leu His Glu Gly Leu His Asn His
        195                 200                 205

His Thr Glu Lys Ser Leu Ser His Ser Pro Gly Lys
    210                 215                 220

<210> SEQ ID NO 7
<211> LENGTH: 230
```

```
<212> TYPE: PRT
<213> ORGANISM: Mus musculus

<400> SEQUENCE: 7

Gly Pro Thr Ile Lys Pro Cys Pro Cys Lys Cys Pro Ala Pro Asn
1               5                   10                  15

Leu Leu Gly Gly Pro Ser Val Phe Ile Phe Pro Pro Lys Ile Lys Asp
                20                  25                  30

Val Leu Met Ile Ser Leu Ser Pro Ile Val Thr Cys Val Val Val Asp
                35                  40                  45

Val Ser Glu Asp Asp Pro Asp Val Gln Ile Ser Trp Phe Val Asn Asn
50                  55                  60

Val Glu Val His Thr Ala Gln Thr Gln Thr His Arg Glu Asp Tyr Asn
65                  70                  75                  80

Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Pro
                100                 105                 110

Ala Pro Ile Glu Arg Thr Ile Ser Lys Pro Lys Gly Ser Val Arg Ala
            115                 120                 125

Pro Gln Val Tyr Val Leu Pro Pro Pro Glu Glu Met Thr Lys Lys
        130                 135                 140

Gln Val Thr Leu Thr Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
                180                 185                 190

Leu Arg Val Glu Lys Lys Asn Trp Val Glu Arg Asn Ser Tyr Ser Cys
                195                 200                 205

Ser Val Val His Glu Gly Leu His Asn His Thr Thr Lys Ser Phe
            210                 215                 220

Ser Arg Thr Pro Gly Lys
225                 230

<210> SEQ ID NO 8
<211> LENGTH: 302
<212> TYPE: PRT
<213> ORGANISM: Mus musculus

<400> SEQUENCE: 8

Ser Thr Ile Asn Pro Cys Pro Pro Cys Lys Glu Cys His Lys Cys Pro
1               5                   10                  15

Ala Pro Asn Leu Glu Gly Gly Pro Ser Val Phe Ile Phe Pro Pro Asn
                20                  25                  30

Ile Lys Asp Val Leu Met Ile Ser Leu Thr Pro Lys Val Thr Cys Val
                35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Ile Arg Val Val Ser Thr Leu Pro Ile Gln His
                85                  90                  95

Gln Asp Trp Met Ser Gly Lys Glu Phe Lys Cys Lys Val Asn Asn Lys
                100                 105                 110
```

```
Asp Leu Pro Ser Pro Ile Glu Arg Thr Ile Ser Lys Ile Lys Gly Leu
            115                 120                 125

Val Arg Ala Pro Gln Val Tyr Ile Leu Pro Pro Ala Glu Gln Leu
130                 135                 140

Ser Arg Lys Asp Val Ser Leu Thr Cys Leu Val Val Gly Phe Asn Pro
145                 150                 155                 160

Gly Asp Ile Ser Val Glu Trp Thr Ser Asn Gly His Thr Glu Glu Asn
                165                 170                 175

Tyr Lys Asp Thr Ala Pro Val Leu Asp Ser Asp Gly Ser Tyr Phe Ile
            180                 185                 190

Tyr Ser Lys Leu Asn Met Lys Thr Ser Lys Trp Glu Lys Thr Asp Ser
        195                 200                 205

Phe Ser Cys Asn Val Arg His Glu Gly Leu Lys Asn Tyr Tyr Leu Lys
    210                 215                 220

Lys Thr Ile Ser Arg Ser Pro Gly Leu Asp Leu Asp Asp Ile Cys Ala
225                 230                 235                 240

Glu Ala Lys Asp Gly Glu Leu Asp Gly Leu Trp Thr Thr Ile Thr Ile
                245                 250                 255

Phe Ile Ser Leu Phe Leu Leu Ser Val Cys Tyr Ser Ala Ser Val Thr
            260                 265                 270

Leu Phe Lys Val Lys Trp Ile Phe Ser Ser Val Val Glu Leu Lys Gln
        275                 280                 285

Lys Ile Ser Pro Asp Tyr Arg Asn Met Ile Gly Gln Gly Ala
    290                 295                 300

<210> SEQ ID NO 9
<211> LENGTH: 295
<212> TYPE: PRT
<213> ORGANISM: Mus musculus

<400> SEQUENCE: 9

Ser Thr Pro Pro Gly Ser Ser Cys Pro Pro Gly Asn Ile Leu Gly Gly
1               5                   10                  15

Pro Ser Val Phe Ile Phe Pro Pro Lys Pro Lys Asp Ala Leu Met Ile
            20                  25                  30

Ser Leu Thr Pro Lys Val Thr Cys Val Val Val Asp Val Ser Glu Asp
        35                  40                  45

Asp Pro Asp Val His Val Ser Trp Phe Val Asp Asn Lys Glu Val His
    50                  55                  60

Thr Ala Trp Thr Gln Pro Arg Glu Ala Gln Tyr Asn Ser Thr Phe Arg
65                  70                  75                  80

Val Val Ser Ala Leu Pro Ile Gln His Gln Asp Trp Met Arg Gly Lys
                85                  90                  95

Glu Phe Lys Cys Lys Val Asn Asn Lys Ala Leu Pro Ala Pro Ile Glu
            100                 105                 110

Arg Thr Ile Ser Lys Pro Lys Gly Arg Ala Gln Thr Pro Gln Val Tyr
        115                 120                 125

Thr Ile Pro Pro Pro Arg Glu Gln Met Ser Lys Lys Val Ser Leu
130                 135                 140

Thr Cys Leu Val Thr Asn Phe Phe Ser Glu Ala Ile Ser Val Glu Trp
145                 150                 155                 160

Glu Arg Asn Gly Glu Leu Glu Gln Asp Tyr Lys Asn Thr Pro Pro Ile
                165                 170                 175

Leu Asp Ser Asp Gly Thr Tyr Phe Leu Tyr Ser Lys Leu Thr Val Asp
            180                 185                 190
```

```
Thr Asp Ser Trp Leu Gln Gly Glu Ile Phe Thr Cys Ser Val Val His
        195                 200                 205

Glu Ala Leu His Asn His His Thr Gln Lys Asn Leu Ser Arg Ser Pro
210                 215                 220

Glu Leu Glu Leu Asn Glu Thr Cys Ala Glu Ala Gln Asp Gly Glu Leu
225                 230                 235                 240

Asp Gly Leu Trp Thr Thr Ile Thr Ile Phe Ile Ser Leu Phe Leu Leu
                245                 250                 255

Ser Val Cys Tyr Ser Ala Ser Val Thr Leu Phe Lys Val Lys Trp Ile
                260                 265                 270

Phe Ser Ser Val Val Gln Val Lys Gln Thr Ala Ile Pro Asp Tyr Arg
        275                 280                 285

Asn Met Ile Gly Gln Gly Ala
        290                 295
```

<210> SEQ ID NO 10
<211> LENGTH: 220
<212> TYPE: PRT
<213> ORGANISM: Homo sapiens

<400> SEQUENCE: 10

```
Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
        210                 215                 220
```

<210> SEQ ID NO 11
<211> LENGTH: 223
<212> TYPE: PRT
<213> ORGANISM: Homo sapiens

<400> SEQUENCE: 11

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
                20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
    210                 215                 220

<210> SEQ ID NO 12
<211> LENGTH: 290
<212> TYPE: PRT
<213> ORGANISM: Homo sapiens

<400> SEQUENCE: 12

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr

```
                145                 150                 155                 160
        Pro Lys Ala Glu Val Ile Trp Thr Ser Ser Asp His Gln Val Leu Ser
                        165                 170                 175

Gly Lys Thr Thr Thr Thr Asn Ser Lys Arg Glu Glu Lys Leu Phe Asn
                        180                 185                 190

Val Thr Ser Thr Leu Arg Ile Asn Thr Thr Thr Asn Glu Ile Phe Tyr
                        195                 200                 205

Cys Thr Phe Arg Arg Leu Asp Pro Glu Glu Asn His Thr Ala Glu Leu
                        210                 215                 220

Val Ile Pro Glu Leu Pro Leu Ala His Pro Pro Asn Glu Arg Thr His
        225                 230                 235                 240

Leu Val Ile Leu Gly Ala Ile Leu Leu Cys Leu Gly Val Ala Leu Thr
                        245                 250                 255

Phe Ile Phe Arg Leu Arg Lys Gly Arg Met Met Asp Val Lys Lys Cys
                        260                 265                 270

Gly Ile Gln Asp Thr Asn Ser Lys Lys Gln Ser Asp Thr His Leu Glu
                        275                 280                 285

Glu Thr
            290

<210> SEQ ID NO 13
<211> LENGTH: 19
<212> TYPE: PRT
<213> ORGANISM: Homo sapiens

<400> SEQUENCE: 13

Met Gly Trp Ser Cys Ile Ile Leu Phe Leu Val Ala Thr Ala Thr Gly
1               5                   10                  15

Val His Ser

<210> SEQ ID NO 14
<211> LENGTH: 437
<212> TYPE: PRT
<213> ORGANISM: Homo sapiens

<400> SEQUENCE: 14

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
                35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Arg Ile Ile Cys
                115                 120                 125

Ser Thr Ser Gly Gly Phe Pro Glu Pro His Leu Ser Trp Leu Glu Asn
            130                 135                 140

Gly Glu Glu Leu Asn Ala Ile Asn Thr Thr Val Ser Gln Asp Pro Glu
145                 150                 155                 160
```

```
Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
            195                 200                 205

Gly Ser Asp Lys Thr His Thr Cys Pro Pro Cys Pro Ala Pro Glu Leu
            210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
            245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
            275                 280                 285

Thr Tyr Arg Val Val Ser Val Leu Thr Val Leu His Gln Asp Trp Leu
            290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
            325                 330                 335

Gln Val Tyr Thr Leu Pro Pro Ser Arg Asp Glu Leu Thr Lys Asn Gln
            340                 345                 350

Val Ser Leu Thr Cys Leu Val Lys Gly Phe Tyr Pro Ser Asp Ile Ala
            355                 360                 365

Val Glu Trp Glu Ser Asn Gly Gln Pro Glu Asn Asn Tyr Lys Thr Thr
            370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
            405                 410                 415

Val Met His Glu Ala Leu His Asn His Tyr Thr Gln Lys Ser Leu Ser
            420                 425                 430

Leu Ser Pro Gly Lys
            435

<210> SEQ ID NO 15
<211> LENGTH: 306
<212> TYPE: PRT
<213> ORGANISM: Mus musculus

<400> SEQUENCE: 15

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
            35                  40                  45

Lys Val Leu Leu Pro Cys Arg Tyr Asn Ser Pro His Glu Asp Glu Ser
            50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
```

```
                    85                  90                  95
Tyr Asp Asn Thr Thr Tyr Ser Leu Ile Ile Leu Gly Leu Val Leu Ser
                100                 105                 110

Asp Arg Gly Thr Tyr Ser Cys Val Val Gln Lys Lys Glu Arg Gly Thr
            115                 120                 125

Tyr Glu Val Lys His Leu Ala Leu Val Lys Leu Ser Ile Lys Ala Asp
        130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
        290                 295                 300

Phe Leu
305

<210> SEQ ID NO 16
<211> LENGTH: 36
<212> TYPE: DNA
<213> ORGANISM: Artificial Sequence
<220> FEATURE:
<223> OTHER INFORMATION: Primer for site-directed mutagenesis S156I-f

<400> SEQUENCE: 16
ccatcaacac aaccgtgatc caagaccccg aaacag                              36

<210> SEQ ID NO 17
<211> LENGTH: 36
<212> TYPE: DNA
<213> ORGANISM: Artificial Sequence
<220> FEATURE:
<223> OTHER INFORMATION: Primer for site-directed mutagenesis S156I-r

<400> SEQUENCE: 17
ctgtttcggg gtcttggatc acggttgtgt tgatgg                              36

<210> SEQ ID NO 18
<211> LENGTH: 36
<212> TYPE: DNA
<213> ORGANISM: Artificial Sequence
<220> FEATURE:
<223> OTHER INFORMATION: Primer for site-directed mutagenesis A165S-f

<400> SEQUENCE: 18
ccgaaacaga gctctacagc gtgagtagta agctgg                              36
```

<210> SEQ ID NO 19
<211> LENGTH: 36
<212> TYPE: DNA
<213> ORGANISM: Artificial Sequence
<220> FEATURE:
<223> OTHER INFORMATION: Primer for site-directed mutagenesis A165S-r

<400> SEQUENCE: 19
ccagcttact actcacgctg tagagctctg tttcgg					36

<210> SEQ ID NO 20
<211> LENGTH: 31
<212> TYPE: DNA
<213> ORGANISM: Artificial Sequence
<220> FEATURE:
<223> OTHER INFORMATION: Primer for site-directed mutagenesis S131A-f

<400> SEQUENCE: 20
atcatctgca gtaccgctgg tgggttccct g					31

<210> SEQ ID NO 21
<211> LENGTH: 31
<212> TYPE: DNA
<213> ORGANISM: Artificial Sequence
<220> FEATURE:
<223> OTHER INFORMATION: Primer for site-directed mutagenesis S131A-r

<400> SEQUENCE: 21
cagggaaccc accagcggta ctgcagatga t					31

<210> SEQ ID NO 22
<211> LENGTH: 43
<212> TYPE: DNA
<213> ORGANISM: Artificial Sequence
<220> FEATURE:
<223> OTHER INFORMATION: Primer for site-directed mutagenesis S156F-f

<400> SEQUENCE: 22
catcaacaca accgtgttcc aagaccccga aacagagctc tac					43

<210> SEQ ID NO 23
<211> LENGTH: 41
<212> TYPE: DNA
<213> ORGANISM: Artificial Sequence
<220> FEATURE:
<223> OTHER INFORMATION: Primer for site-directed mutagenesis S156F-r

<400> SEQUENCE: 23
gtttcggggt cttggaacac ggttgtgttg atggcgttga g					41

<210> SEQ ID NO 24
<211> LENGTH: 43
<212> TYPE: DNA
<213> ORGANISM: Artificial Sequence
<220> FEATURE:
<223> OTHER INFORMATION: Primer for site-directed mutagenesis S156R-f

<400> SEQUENCE: 24
catcaacaca accgtgaggc aagaccccga aacagagctc tac					43

<210> SEQ ID NO 25
<211> LENGTH: 41
<212> TYPE: DNA
<213> ORGANISM: Artificial Sequence
<220> FEATURE:

<223> OTHER INFORMATION: Primer for site-directed mutagenesis S156R-r

<400> SEQUENCE: 25
gtttcggggt cttgcctcac ggttgtgttg atggcgttga g                       41

<210> SEQ ID NO 26
<211> LENGTH: 43
<212> TYPE: DNA
<213> ORGANISM: Artificial Sequence
<220> FEATURE:
<223> OTHER INFORMATION: Primer for site-directed mutagenesis S156E-f

<400> SEQUENCE: 26
catcaacaca accgtggagc aagaccccga aacagagctc tac                     43

<210> SEQ ID NO 27
<211> LENGTH: 41
<212> TYPE: DNA
<213> ORGANISM: Artificial Sequence
<220> FEATURE:
<223> OTHER INFORMATION: Primer for site-directed mutagenesis S156E-r

<400> SEQUENCE: 27
gtttcggggt cttgctccac ggttgtgttg atggcgttga g                       41

<210> SEQ ID NO 28
<211> LENGTH: 43
<212> TYPE: DNA
<213> ORGANISM: Artificial Sequence
<220> FEATURE:
<223> OTHER INFORMATION: Primer for site-directed mutagenesis S156D-f

<400> SEQUENCE: 28
catcaacaca accgtggacc aagaccccga aacagagctc tac                     43

<210> SEQ ID NO 29
<211> LENGTH: 41
<212> TYPE: DNA
<213> ORGANISM: Artificial Sequence
<220> FEATURE:
<223> OTHER INFORMATION: Primer for site-directed mutagenesis S156D-r

<400> SEQUENCE: 29
gtttcggggt cttggtccac ggttgtgttg atggcgttga g                       41

<210> SEQ ID NO 30
<211> LENGTH: 43
<212> TYPE: DNA
<213> ORGANISM: Artificial Sequence
<220> FEATURE:
<223> OTHER INFORMATION: Primer for site-directed mutagenesis S156Q-f

<400> SEQUENCE: 30
catcaacaca accgtgcagc aagaccccga aacagagctc tac                     43

<210> SEQ ID NO 31
<211> LENGTH: 41
<212> TYPE: DNA
<213> ORGANISM: Artificial Sequence
<220> FEATURE:
<223> OTHER INFORMATION: Primer for site-directed mutagenesis S156Q-r

<400> SEQUENCE: 31
gtttcggggt cttgctgcac ggttgtgttg atggcgttga g                       41

```
<210> SEQ ID NO 32
<211> LENGTH: 40
<212> TYPE: DNA
<213> ORGANISM: Artificial Sequence
<220> FEATURE:
<223> OTHER INFORMATION: Primer for site-directed mutagenesis S131V-f

<400> SEQUENCE: 32
catctgcagt accgtgggtg ggttccctga gccccatctc                              40

<210> SEQ ID NO 33
<211> LENGTH: 38
<212> TYPE: DNA
<213> ORGANISM: Artificial Sequence
<220> FEATURE:
<223> OTHER INFORMATION: Primer for site-directed mutagenesis S131V-r

<400> SEQUENCE: 33
cagggaaccc acccacggta ctgcagatga ttctcctg                                38

<210> SEQ ID NO 34
<211> LENGTH: 40
<212> TYPE: DNA
<213> ORGANISM: Artificial Sequence
<220> FEATURE:
<223> OTHER INFORMATION: Primer for site-directed mutagenesis S131I-f

<400> SEQUENCE: 34
catctgcagt accatcggtg ggttccctga gccccatctc                              40

<210> SEQ ID NO 35
<211> LENGTH: 38
<212> TYPE: DNA
<213> ORGANISM: Artificial Sequence
<220> FEATURE:
<223> OTHER INFORMATION: Primer for site-directed mutagenesis S131I-r

<400> SEQUENCE: 35
cagggaaccc accgatggta ctgcagatga ttctcctg                                38

<210> SEQ ID NO 36
<211> LENGTH: 40
<212> TYPE: DNA
<213> ORGANISM: Artificial Sequence
<220> FEATURE:
<223> OTHER INFORMATION: Primer for site-directed mutagenesis S131F-f

<400> SEQUENCE: 36
catctgcagt accttcggtg ggttccctga gccccatctc                              40

<210> SEQ ID NO 37
<211> LENGTH: 38
<212> TYPE: DNA
<213> ORGANISM: Artificial Sequence
<220> FEATURE:
<223> OTHER INFORMATION: Primer for site-directed mutagenesis S131F-r

<400> SEQUENCE: 37
cagggaaccc accgaaggta ctgcagatga ttctcctg                                38

<210> SEQ ID NO 38
<211> LENGTH: 40
<212> TYPE: DNA
<213> ORGANISM: Artificial Sequence
<220> FEATURE:
<223> OTHER INFORMATION: Primer for site-directed mutagenesis S131R-f
```

```
<400> SEQUENCE: 38
catctgcagt accaggggtg ggttccctga gccccatctc                    40

<210> SEQ ID NO 39
<211> LENGTH: 38
<212> TYPE: DNA
<213> ORGANISM: Artificial Sequence
<220> FEATURE:
<223> OTHER INFORMATION: Primer for site-directed mutagenesis S131R-r

<400> SEQUENCE: 39
cagggaaccc accctggta ctgcagatga ttctcctg                       38

<210> SEQ ID NO 40
<211> LENGTH: 40
<212> TYPE: DNA
<213> ORGANISM: Artificial Sequence
<220> FEATURE:
<223> OTHER INFORMATION: Primer for site-directed mutagenesis S131E-f

<400> SEQUENCE: 40
catctgcagt accgagggtg ggttccctga gccccatctc                    40

<210> SEQ ID NO 41
<211> LENGTH: 38
<212> TYPE: DNA
<213> ORGANISM: Artificial Sequence
<220> FEATURE:
<223> OTHER INFORMATION: Primer for site-directed mutagenesis S131E-r

<400> SEQUENCE: 41
cagggaaccc accctcggta ctgcagatga ttctcctg                      38

<210> SEQ ID NO 42
<211> LENGTH: 40
<212> TYPE: DNA
<213> ORGANISM: Artificial Sequence
<220> FEATURE:
<223> OTHER INFORMATION: Primer for site-directed mutagenesis S131D-f

<400> SEQUENCE: 42
catctgcagt accgacggtg ggttccctga gccccatctc                    40

<210> SEQ ID NO 43
<211> LENGTH: 38
<212> TYPE: DNA
<213> ORGANISM: Artificial Sequence
<220> FEATURE:
<223> OTHER INFORMATION: Primer for site-directed mutagenesis S131D-r

<400> SEQUENCE: 43
cagggaaccc accgtcggta ctgcagatga ttctcctg                      38

<210> SEQ ID NO 44
<211> LENGTH: 40
<212> TYPE: DNA
<213> ORGANISM: Artificial Sequence
<220> FEATURE:
<223> OTHER INFORMATION: Primer for site-directed mutagenesis S131Q-f

<400> SEQUENCE: 44
catctgcagt acccagggtg ggttccctga gccccatctc                    40

<210> SEQ ID NO 45
<211> LENGTH: 38
```

```
<212> TYPE: DNA
<213> ORGANISM: Artificial Sequence
<220> FEATURE:
<223> OTHER INFORMATION: Primer for site-directed mutagenesis S131Q-r

<400> SEQUENCE: 45
cagggaaccc accctgggta ctgcagatga ttctcctg                              38

<210> SEQ ID NO 46
<211> LENGTH: 42
<212> TYPE: DNA
<213> ORGANISM: Artificial Sequence
<220> FEATURE:
<223> OTHER INFORMATION: Primer for site-directed mutagenesis A165V-f

<400> SEQUENCE: 46
gaaacagagc tctacgtggt gagtagtaag ctggacttta ac                         42

<210> SEQ ID NO 47
<211> LENGTH: 39
<212> TYPE: DNA
<213> ORGANISM: Artificial Sequence
<220> FEATURE:
<223> OTHER INFORMATION: Primer for site-directed mutagenesis A165V-r

<400> SEQUENCE: 47
cttactactc accacgtaga gctctgtttc ggggtcttg                             39

<210> SEQ ID NO 48
<211> LENGTH: 42
<212> TYPE: DNA
<213> ORGANISM: Artificial Sequence
<220> FEATURE:
<223> OTHER INFORMATION: Primer for site-directed mutagenesis A165I-f

<400> SEQUENCE: 48
gaaacagagc tctacatcgt gagtagtaag ctggacttta ac                         42

<210> SEQ ID NO 49
<211> LENGTH: 39
<212> TYPE: DNA
<213> ORGANISM: Artificial Sequence
<220> FEATURE:
<223> OTHER INFORMATION: Primer for site-directed mutagenesis A165I-r

<400> SEQUENCE: 49
cttactactc acgatgtaga gctctgtttc ggggtcttg                             39

<210> SEQ ID NO 50
<211> LENGTH: 42
<212> TYPE: DNA
<213> ORGANISM: Artificial Sequence
<220> FEATURE:
<223> OTHER INFORMATION: Primer for site-directed mutagenesis A165F-f

<400> SEQUENCE: 50
gaaacagagc tctacttcgt gagtagtaag ctggacttta ac                         42

<210> SEQ ID NO 51
<211> LENGTH: 39
<212> TYPE: DNA
<213> ORGANISM: Artificial Sequence
<220> FEATURE:
<223> OTHER INFORMATION: Primer for site-directed mutagenesis A165F-r

<400> SEQUENCE: 51
```
cttactactc acgaagtaga gctctgtttc ggggtcttg            39

<210> SEQ ID NO 52
<211> LENGTH: 42
<212> TYPE: DNA
<213> ORGANISM: Artificial Sequence
<220> FEATURE:
<223> OTHER INFORMATION: Primer for site-directed mutagenesis A165R-f

<400> SEQUENCE: 52
gaaacagagc tctacagggt gagtagtaag ctggacttta ac            42

<210> SEQ ID NO 53
<211> LENGTH: 39
<212> TYPE: DNA
<213> ORGANISM: Artificial Sequence
<220> FEATURE:
<223> OTHER INFORMATION: Primer for site-directed mutagenesis A165R-r

<400> SEQUENCE: 53
cttactactc accctgtaga gctctgtttc ggggtcttg            39

<210> SEQ ID NO 54
<211> LENGTH: 42
<212> TYPE: DNA
<213> ORGANISM: Artificial Sequence
<220> FEATURE:
<223> OTHER INFORMATION: Primer for site-directed mutagenesis A165E-f

<400> SEQUENCE: 54
gaaacagagc tctacgaggt gagtagtaag ctggacttta ac            42

<210> SEQ ID NO 55
<211> LENGTH: 39
<212> TYPE: DNA
<213> ORGANISM: Artificial Sequence
<220> FEATURE:
<223> OTHER INFORMATION: Primer for site-directed mutagenesis A165E-r

<400> SEQUENCE: 55
cttactactc acctcgtaga gctctgtttc ggggtcttg            39

<210> SEQ ID NO 56
<211> LENGTH: 42
<212> TYPE: DNA
<213> ORGANISM: Artificial Sequence
<220> FEATURE:
<223> OTHER INFORMATION: Primer for site-directed mutagenesis A165D-f

<400> SEQUENCE: 56
gaaacagagc tctacgacgt gagtagtaag ctggacttta ac            42

<210> SEQ ID NO 57
<211> LENGTH: 39
<212> TYPE: DNA
<213> ORGANISM: Artificial Sequence
<220> FEATURE:
<223> OTHER INFORMATION: Primer for site-directed mutagenesis A165D-r

<400> SEQUENCE: 57
cttactactc acgtcgtaga gctctgtttc ggggtcttg            39

<210> SEQ ID NO 58
<211> LENGTH: 42
<212> TYPE: DNA
<213> ORGANISM: Artificial Sequence

```
<220> FEATURE:
<223> OTHER INFORMATION: Primer for site-directed mutagenesis A165Q-f

<400> SEQUENCE: 58
gaaacagagc tctaccaggt gagtagtaag ctggacttta ac                42

<210> SEQ ID NO 59
<211> LENGTH: 39
<212> TYPE: DNA
<213> ORGANISM: Artificial Sequence
<220> FEATURE:
<223> OTHER INFORMATION: Primer for site-directed mutagenesis A165Q-r

<400> SEQUENCE: 59
cttactactc acctggtaga gctctgtttc ggggtcttg                    39

<210> SEQ ID NO 60
<211> LENGTH: 40
<212> TYPE: DNA
<213> ORGANISM: Artificial Sequence
<220> FEATURE:
<223> OTHER INFORMATION: Primer for site-directed mutagenesis T130A-f

<400> SEQUENCE: 60
caggagaatc atctgcagtg catctggtgg gttccctgag                   40

<210> SEQ ID NO 61
<211> LENGTH: 40
<212> TYPE: DNA
<213> ORGANISM: Artificial Sequence
<220> FEATURE:
<223> OTHER INFORMATION: Primer for site-directed mutagenesis T130A-r

<400> SEQUENCE: 61
ctcagggaac ccaccagatg cactgcagat gattctcctg                   40

<210> SEQ ID NO 62
<211> LENGTH: 39
<212> TYPE: DNA
<213> ORGANISM: Artificial Sequence
<220> FEATURE:
<223> OTHER INFORMATION: Primer for site-directed mutagenesis S131V-f

<400> SEQUENCE: 62
gagaatcatc tgcagtaccg ttggtgggtt ccctgagcc                    39

<210> SEQ ID NO 63
<211> LENGTH: 39
<212> TYPE: DNA
<213> ORGANISM: Artificial Sequence
<220> FEATURE:
<223> OTHER INFORMATION: Primer for site-directed mutagenesis S131V-r

<400> SEQUENCE: 63
ggctcaggga acccaccaac ggtactgcag atgattctc                    39

<210> SEQ ID NO 64
<211> LENGTH: 35
<212> TYPE: DNA
<213> ORGANISM: Artificial Sequence
<220> FEATURE:
<223> OTHER INFORMATION: Primer for site-directed mutagenesis L139V-f

<400> SEQUENCE: 64
gttccctgag ccccatgtta gctggctgga gaacg                        35
```

<210> SEQ ID NO 65
<211> LENGTH: 35
<212> TYPE: DNA
<213> ORGANISM: Artificial Sequence
<220> FEATURE:
<223> OTHER INFORMATION: Primer for site-directed mutagenesis L139V-r

<400> SEQUENCE: 65
cgttctccag ccagctaaca tggggctcag ggaac                          35

<210> SEQ ID NO 66
<211> LENGTH: 41
<212> TYPE: DNA
<213> ORGANISM: Artificial Sequence
<220> FEATURE:
<223> OTHER INFORMATION: Primer for site-directed mutagenesis V155A-f

<400> SEQUENCE: 66
caacgccatc aacacaaccg catcccaaga ccccgaaaca g                   41

<210> SEQ ID NO 67
<211> LENGTH: 41
<212> TYPE: DNA
<213> ORGANISM: Artificial Sequence
<220> FEATURE:
<223> OTHER INFORMATION: Primer for site-directed mutagenesis V155A-r

<400> SEQUENCE: 67
ctgtttcggg gtcttgggat gcggttgtgt tgatggcgtt g                   41

<210> SEQ ID NO 68
<211> LENGTH: 41
<212> TYPE: DNA
<213> ORGANISM: Artificial Sequence
<220> FEATURE:
<223> OTHER INFORMATION: Primer for site-directed mutagenesis V155I-f

<400> SEQUENCE: 68
caacgccatc aacacaacca tctcccaaga ccccgaaaca g                   41

<210> SEQ ID NO 69
<211> LENGTH: 41
<212> TYPE: DNA
<213> ORGANISM: Artificial Sequence
<220> FEATURE:
<223> OTHER INFORMATION: Primer for site-directed mutagenesis V155I-r

<400> SEQUENCE: 69
ctgtttcggg gtcttgggag atggttgtgt tgatggcgtt g                   41

<210> SEQ ID NO 70
<211> LENGTH: 41
<212> TYPE: DNA
<213> ORGANISM: Artificial Sequence
<220> FEATURE:
<223> OTHER INFORMATION: Primer for site-directed mutagenesis V155T-f

<400> SEQUENCE: 70
caacgccatc aacacaacca cctcccaaga ccccgaaaca g                   41

<210> SEQ ID NO 71
<211> LENGTH: 41
<212> TYPE: DNA
<213> ORGANISM: Artificial Sequence
<220> FEATURE:
<223> OTHER INFORMATION: Primer for site-directed mutagenesis V155T-r

```
<400> SEQUENCE: 71
ctgtttcggg gtcttgggag gtggttgtgt tgatggcgtt g                          41

<210> SEQ ID NO 72
<211> LENGTH: 39
<212> TYPE: DNA
<213> ORGANISM: Artificial Sequence
<220> FEATURE:
<223> OTHER INFORMATION: Primer for site-directed mutagenesis S156A-f

<400> SEQUENCE: 72
gccatcaaca caaccgtggc acaagacccc gaaacagag                             39

<210> SEQ ID NO 73
<211> LENGTH: 39
<212> TYPE: DNA
<213> ORGANISM: Artificial Sequence
<220> FEATURE:
<223> OTHER INFORMATION: Primer for site-directed mutagenesis S156A-r

<400> SEQUENCE: 73
ctctgtttcg gggtcttgtg ccacggttgt gttgatggc                             39

<210> SEQ ID NO 74
<211> LENGTH: 43
<212> TYPE: DNA
<213> ORGANISM: Artificial Sequence
<220> FEATURE:
<223> OTHER INFORMATION: Primer for site-directed mutagenesis V166A-f

<400> SEQUENCE: 74
cgaaacagag ctctacgccg caagtagtaa gctggacttt aac                        43

<210> SEQ ID NO 75
<211> LENGTH: 43
<212> TYPE: DNA
<213> ORGANISM: Artificial Sequence
<220> FEATURE:
<223> OTHER INFORMATION: Primer for site-directed mutagenesis V166A-r

<400> SEQUENCE: 75
gttaaagtcc agcttactac ttgcggcgta gagctctgtt tcg                        43

<210> SEQ ID NO 76
<211> LENGTH: 44
<212> TYPE: DNA
<213> ORGANISM: Artificial Sequence
<220> FEATURE:
<223> OTHER INFORMATION: Primer for site-directed mutagenesis V166L-f

<400> SEQUENCE: 76
ccgaaacaga gctctacgcc ctcagtagta agctggactt taac                       44

<210> SEQ ID NO 77
<211> LENGTH: 44
<212> TYPE: DNA
<213> ORGANISM: Artificial Sequence
<220> FEATURE:
<223> OTHER INFORMATION: Primer for site-directed mutagenesis V166L-r

<400> SEQUENCE: 77
gttaaagtcc agcttactac tgagggcgta gagctctgtt tcgg                       44

<210> SEQ ID NO 78
```

```
<211> LENGTH: 44
<212> TYPE: DNA
<213> ORGANISM: Artificial Sequence
<220> FEATURE:
<223> OTHER INFORMATION: Primer for site-directed mutagenesis V166T-f

<400> SEQUENCE: 78
ccgaaacaga gctctacgcc accagtagta agctggactt taac                    44

<210> SEQ ID NO 79
<211> LENGTH: 44
<212> TYPE: DNA
<213> ORGANISM: Artificial Sequence
<220> FEATURE:
<223> OTHER INFORMATION: Primer for site-directed mutagenesis V166T-r

<400> SEQUENCE: 79
gttaaagtcc agcttactac tggtggcgta gagctctgtt tcgg                    44

<210> SEQ ID NO 80
<211> LENGTH: 44
<212> TYPE: DNA
<213> ORGANISM: Artificial Sequence
<220> FEATURE:
<223> OTHER INFORMATION: Primer for site-directed mutagenesis
      S155A/S156A-f

<400> SEQUENCE: 80
caacgccatc aacacaaccg cagcacaaga ccccgaaaca gagc                    44

<210> SEQ ID NO 81
<211> LENGTH: 44
<212> TYPE: DNA
<213> ORGANISM: Artificial Sequence
<220> FEATURE:
<223> OTHER INFORMATION: Primer for site-directed mutagenesis
      S155A/S156A-r

<400> SEQUENCE: 81
gctctgtttc ggggtcttgt gctgcggttg tgttgatggc gttg                    44

<210> SEQ ID NO 82
<211> LENGTH: 44
<212> TYPE: DNA
<213> ORGANISM: Artificial Sequence
<220> FEATURE:
<223> OTHER INFORMATION: Primer for site-directed mutagenesis
      V155I/S156A-f

<400> SEQUENCE: 82
caacgccatc aacacaacca tcgcccaaga ccccgaaaca gagc                    44

<210> SEQ ID NO 83
<211> LENGTH: 44
<212> TYPE: DNA
<213> ORGANISM: Artificial Sequence
<220> FEATURE:
<223> OTHER INFORMATION: Primer for site-directed mutagenesis
      V155I/S156A-r

<400> SEQUENCE: 83
gctctgtttc ggggtcttgg gcgatggttg tgttgatggc gttg                    44

<210> SEQ ID NO 84
<211> LENGTH: 43
<212> TYPE: DNA
<213> ORGANISM: Artificial Sequence
```

```
<220> FEATURE:
<223> OTHER INFORMATION: Primer for site-directed mutagenesis
      V155T/S156A-f

<400> SEQUENCE: 84
caacgccatc aacacaacca ccgcccaaga ccccgaaaca gag        43

<210> SEQ ID NO 85
<211> LENGTH: 43
<212> TYPE: DNA
<213> ORGANISM: Artificial Sequence
<220> FEATURE:
<223> OTHER INFORMATION: Primer for site-directed mutagenesis
      V155T/S156A-r

<400> SEQUENCE: 85
ctctgtttcg gggtcttggg cggtggttgt gttgatggcg ttg        43
```

CD80 VARIANT PROTEINS AND USES THEREOF

CROSS REFERENCE TO RELATED APPLICATIONS

This application is a 371 U.S. National Stage of International Application No. PCT/US2020/029834, filed Apr. 24, 2020, which claims the benefit of priority to U.S. Provisional Application No. 62/839,542, filed on Apr. 26, 2019. The entire disclosures of the above applications are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: Sequence_Listing_2_SeqList_ST25. txt, date recorded: Dec. 7, 2021, file size ~46 kilobytes).

BACKGROUND

T-cell lymphocytes play a critical role in cell-mediated immunity by providing for an adaptive response to specific pathogens. T-cell activation depends on activation of at least two signaling pathways, one that is antigen specific and the other that is antigen nonspecific. Antigen-specific activation of T-cells is mediated by peptide/major histocompatibility complexes on antigen-presenting cells interacting with specific T-cell antigen receptors. Binding of B7-related molecules expressed on antigen-presenting cells, which are CD80 (B7-1) and CD86 (B7-2), to CD28 and/or CTLA-4 on T-cells provides important antigen-nonspecific costimulatory signals essential for optimum immune responses. The binding of CD80 to the T-cell homodimers of CD28 and CTLA-4 generates costimulatory and inhibitory signals in T-cell, and the binding of CD80 to PD-L1 interrupts the interaction between PD-1 and PD-L1 removing the inhibitory signals of T-cell activation. Because these signaling pathways determine the magnitude of a T-cell response to antigen, as well as downstream responses to antigen, agents that specifically modulate one or more costimulatory signals, e.g., by modulating one or more of the interactions between CD80 and CD28 and/or CTLA4, may be effective in treating disorders that result from dysregulated cell-mediated immune responses.

CD80 is a member of the immunoglobulin super-family (IgSF) with its extracellular domain consisting of one amino-terminal Ig variable-like (IgV) and one membrane proximal Ig constant-like (IgC) domain. Efforts modulating the binding affinities towards these three target proteins of CD80, CTLA-4, PD-L1 and CD28 have been carried out. (Peach et al., (1995) JBC, 270 (36), 21181-21187).

CD28 favors the binding of monomeric ligands and CTLA-4 favors that of dimeric ligands, the ratio of CD80 in monomeric versus multimeric forms could influence the ensuing immune response. Accordingly there is a need to provide improved CD80 variants with increased, decreased or a combination of increased and decreased affinity to each of the CTLA-4, PD-L1 and CD28 ligands to selectively modulate T-cell activation to achieve specific therapeutic effects. The present disclosure provides methods and compositions relating to the same.

SUMMARY

The present disclosure provides variant CD80 polypeptides. In some embodiments, the variant CD80 polypeptides comprise an amino acid sequence having at least 80% amino acid sequence identity to SEQ ID NO: 1, wherein the variant CD80 polypeptide comprises one or more of the amino acid substitution modifications compared to SEQ ID NO: 1, wherein the one or more substitution modifications are at positions 131, 139, 155, 165, or 166 of SEQ ID NO: 1. In some embodiments, the variant CD80 polypeptide comprises two or more of the amino acid substitution modifications compared to SEQ ID NO: 1, and wherein the two or more substitution modifications are at positions 130, 131, 139, 155, 156, 165, or 166 of SEQ ID NO: 1. In some embodiments, the variant CD80 polypeptide comprises three or more of the amino acid substitution modifications compared to SEQ ID NO: 1, and wherein the three or more substitution modifications are at positions 130, 131, 139, 155, 156, 165, or 166 of SEQ ID NO: 1. In some embodiments, the variant CD80 polypeptide comprises four or more of the amino acid substitution modifications compared to SEQ ID NO: 1, and wherein the four or more substitution modifications are at positions 130, 131, 139, 155, 156, 165, or 166 of SEQ ID NO: 1. In some embodiments, the variant CD80 polypeptide comprises five or more of the amino acid substitution modifications compared to SEQ ID NO: 1, and wherein the five or more substitution modifications are at positions 130, 131, 139, 155, 156, 165, or 166 of SEQ ID NO: 1.

In some embodiments, the variant CD80 polypeptide has increased or decreased binding affinity for CTLA-4, CD28, or PD-L1 compared to SEQ ID NO: 1.

In other embodiments, the variant CD80 polypeptide further comprises a second polypeptide that is capable of dimerizing. In some embodiments, the second polypeptide is an immunoglobulin Fc domain, which is a human IgG1 Fc domain, a human IgG2 Fc domain, a human IgG3 Fc domain, a human IgG4 Fc domain, a mouse IgG1 Fc domain, a mouse IgG2a Fc domain, a mouse IgG2b Fc domain, or a mouse IgG3 Fc domain. In some embodiments, the variant CD80 polypeptide further comprises a therapeutically active moiety.

The present disclosure also provides a polynucleotide encoding the variant CD80 polypeptide of the present disclosure, which is a synthetic nucleic acid or cDNA. In some embodiments, the polynucleotide is operably linked to a transcriptional control element that is functional in a eukaryotic cell.

The present disclosure also provides a vector comprising the polynucleotide of the present disclosure, which is an expression vector, a mammalian vector or a viral vector.

The present disclosure also provides a cell comprising the vector of the present disclosure, which is a mammalian cell including a human cell.

The present disclosure further provides a pharmaceutical composition comprises the variant CD80 polypeptide of the present disclosure, further comprising a pharmaceutically acceptable excipient. In some embodiments, the pharmaceutical composition is sterile. In some embodiments, a kit comprises the pharmaceutical composition of the present disclosure, and instructions for use.

The present disclosure also provides an article of manufacture comprises the pharmaceutical composition of the present disclosure in a vial, which is sealed. In some embodiments, a kit comprises the article of manufacture of the present disclosure, and instructions for use.

The present disclosure further provides a method of modulating an immune response in a subject, comprising administering the pharmaceutical composition of the present disclosure to the subject. In some embodiments, modulating the immune response treats a disease or condition in the subject. In some embodiments, the immune response is increased or decreased. In some embodiments, the disease or condition is a tumor or cancer. In some embodiments, the disease or condition is an inflammatory or autoimmune disease or condition.

The present disclosure further provides a method of treating a disease or condition in a subject, comprising administering the pharmaceutical composition of the present disclosure to the subject. In some embodiments, the disease or condition is an infection. In some embodiments, the disease or condition is a tumor or cancer. In some embodiments, the disease or condition is an inflammatory or autoimmune disease or condition.

BRIEF DESCRIPTION OF THE DRAWINGS

FIG. 1 provides an amino acid sequence of a Wild-type Human CD80 Extracellular Domain (ECD) (SEQ ID NO: 1), which is obtained from UniProtKB P33681 (CD80_HUMAN). Amino acids are bolded and underlined to display positions of substitutions/mutations of interest.

FIG. 2 provides an amino acid sequence of a Human IgG1 Fc Domain (SEQ ID NO: 2), which is partially obtained from UniProtKB P01857 (IGHG1_HUMAN), Immunoglobulin heavy constant gamma 1.

FIG. 3 provides an amino acid sequence of a Human IgG2 Fc Domain (SEQ ID NO: 3), which is partially obtained from UniProtKB P01859 (IGHG2_HUMAN), Immunoglobulin heavy constant gamma 2.

FIG. 4 provides an amino acid sequence of a Human IgG3 Fc Domain (SEQ ID NO: 4), which is partially obtained from UniProtKB P01860 (IGHG3_HUMAN), Immunoglobulin heavy constant gamma 3.

FIG. 5 provides an amino acid sequence of a Human IgG4 Fc Domain (SEQ ID NO: 5), which is partially obtained from UniProtKB P01861 (IGHG4_HUMAN), Immunoglobulin heavy constant gamma 4.

FIG. 6 provides an amino acid sequence of a Mouse IgG1 Fc Domain (SEQ ID NO: 6), which is partially obtained from UniProtKB P01868 (IGHG1_MOUSE), Ig gamma-1 chain C region secreted from.

FIG. 7 provides an amino acid sequence of a Mouse IgG2a Fc Domain (SEQ ID NO: 7), which is partially obtained from UniProtKB P01863 (GCAA_MOUSE), Ig gamma-2A chain C region, A allele.

FIG. 8 provides an amino acid sequence of a Mouse IgG2b Fc Domain (SEQ ID NO: 8), which is partially obtained from UniProtKB P01867 (IGG2B_MOUSE), Ig gamma-2B chain C region.

FIG. 9 provides an amino acid sequence of a Mouse IgG3 Fc Domain (SEQ ID NO: 9), which is partially obtained from UniProtKB P03987 (IGHG3_MOUSE), Ig gamma-3 chain C region.

FIG. 10 provides an amino acid sequence of a Human CD28 (SEQ ID NO: 10), which is obtained from UniProtKB P10747 (CD28_HUMAN), T-cell-specific surface glycoprotein CD28.

FIG. 11 provides an amino acid sequence of a Human CTLA-4 (SEQ ID NO: 11), which is obtained from UniProtKB P16410 (CTLA4_HUMAN), Cytotoxic T-lymphocyte protein 4.

FIG. 12 provides an amino acid sequence of a Human PD-L1 (SEQ ID NO: 12), which is obtained from UniProtKB Q9NZQ7 (PD1L1_HUMAN), Programmed cell death 1 ligand 1.

FIG. 13A depicts a schematic diagram of a CD80-Fc Expression cassette, encoding (i) Leader Sequence (FIG. 13B), (ii) CD80 (either wild-type human CD80 or Mutated human CD80 variant of interest taught in the present disclosure) and (iii) Ig Fc domains of interest taught in the present disclosure, from an expression vector. FIG. 13B provides an amino acid sequence of leader sequence (SEQ ID NO: 13) obtained from a Human IgG heavy chain (GenBank: QBK47409.1). FIG. 13C depicts a schematic diagram of a CD80-Fc fusion protein consisting of two CD80-Fc fusion polypeptides dimerized and connected via disulfide bonds.

FIG. 14A provides an amino acid sequence of a Human CD80-Fc fusion polypeptide (SEQ ID NO: 14) expressed from a hCD80-Fc expression construct. FIG. 14B provides an amino acid sequence of a wild type mouse CD80 sequence (SEQ ID NO: 15).

FIG. 15E depicts SDS-PAGE analysis results of selected and purified CD80-Fc Fusion Proteins in a non-reducing condition. FIG. 15F depicts SDS-PAGE analysis results of selected and purified CD80-Fc fusion polypeptides in a reducing condition. Samples loaded with purified CD80-Fc fusion protein in FIGS. 15E-15F are as follows; Lane 1: Molecular Weight Marker; Lane 2: S131V, 10 ug/lane; Lane 3: V155A, 10 ug/lane; Lane 4: V155I, 10 ug/lane; Lane 5: V155T, 10 ug/lane.

DETAILED DESCRIPTION

Figure 15A:
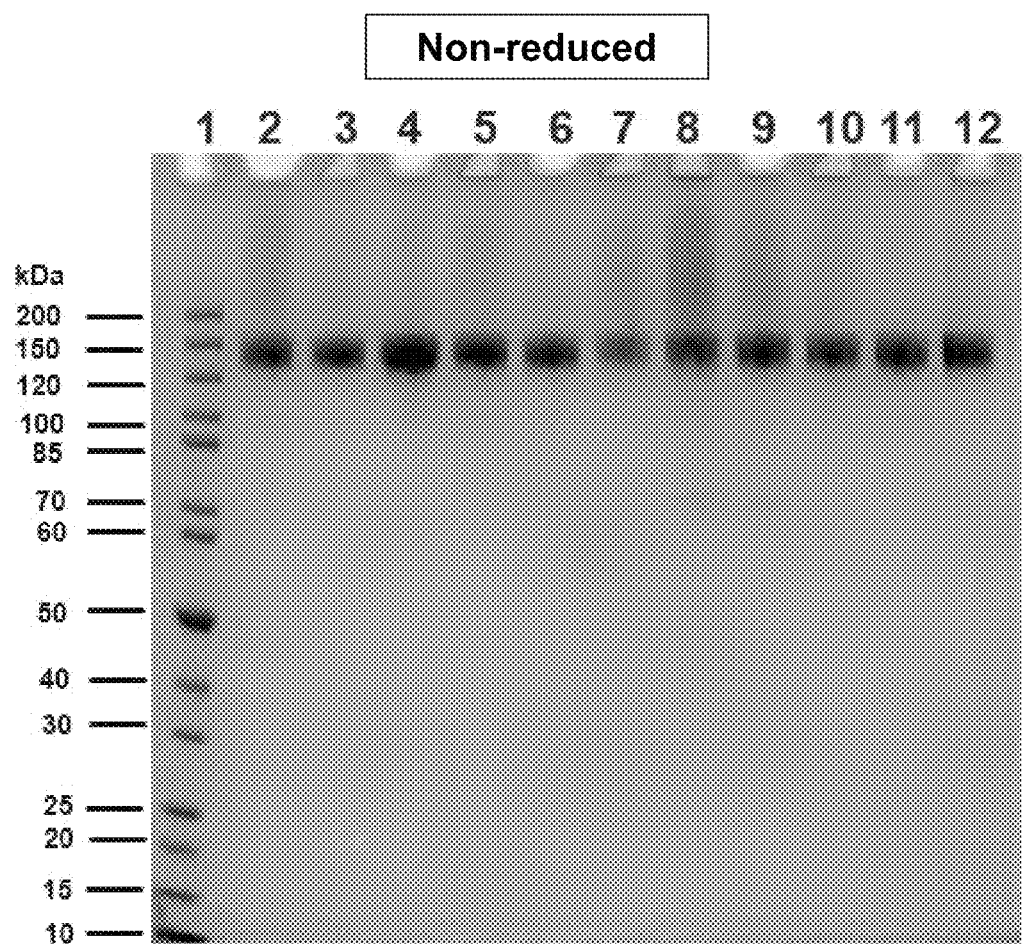
FIG. 15A depicts SDS-PAGE analysis results of selected and purified CD80-Fc Fusion Proteins in a non-reducing condition.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein may be employed in practicing the disclosure. It is also understood that every embodiment of the disclosure may optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act, the order of the acts of the method is not necessarily limited to the order in which the acts of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment found within the prior art, can be explicitly excluded from the claims, regardless of whether or not the specific exclusion is recited in the specification.

Headings are included herein for reference and to aid in locating certain sections. Headings are not intended to limit the scope of the embodiments and concepts described in the sections under those headings, and those embodiments and concepts may have applicability in other sections throughout the entire disclosure.

I. Definitions

While the following terms are believed to be well understood by one of ordinary skill in the art, the following definitions are set forth to facilitate explanation of the presently disclosed subject matter. Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The terms used throughout this specification are defined as follows unless otherwise limited in specific instances. As used in the specification and the appended claims, the singular forms "a," "an," and "the" include plural referents unless the context clearly dictates otherwise. Unless defined otherwise, all technical and scientific terms, acronyms, and abbreviations used herein have the same meaning as commonly understood by one of ordinary skill in the art to which the disclosure pertains. Unless indicated otherwise, abbreviations and symbols for chemical and biochemical names is per IUPAC-IUB nomenclature. Unless indicated otherwise, all numerical ranges are inclusive of the values defining the range as well as all integer values in-between.

The term "affinity modified" as used in the context of an immunoglobulin superfamily domain, means a mammalian immunoglobulin superfamily (IgSF) domain having an altered amino acid sequence (relative to the corresponding wild-type parental or unmodified IgSF domain) such that it has an increased or decreased binding affinity or avidity to at least one of its cognate binding partners (alternatively "counter-structures") compared to the parental wild-type or unmodified (i.e., non-affinity modified) IgSF control domain. Included in this context is an affinity modified CD80 IgSF domain. In some embodiments, the affinity-modified IgSF domain can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions, in a wildtype or unmodified IgSF domain. An increase or decrease in binding affinity or avidity can be determined using well known binding assays such as flow cytometry. Larsen et al., American Journal of Transplantation, Vol 5: 443-453 (2005). See also, Linsley et al., Immunity, 1: 7930801 (1994). An increase in a protein's binding affinity or avidity to its cognate binding partner(s) is to a value at least 10% greater than that of the wild-type IgSF domain control and in some embodiments, at least 20%, 30%, 40%, 50%, 100%, 200%, 300%, 500%, 1000%, 5000%, or 10000% greater than that of the wild-type IgSF domain control value. A decrease in a protein's binding affinity or avidity to at least one of its cognate binding partner is to a value no greater than 90% of the control but no less than 10% of the wild-type IgSF domain control value, and in some embodiments no greater than 80%, 70% 60%, 50%, 40%, 30%, or 20% but no less than 10% of the wild-type IgSF domain control value. An affinity-modified protein is altered in primary amino acid sequence by substitution, addition, or deletion of amino acid residues. The term "affinity modified IgSF domain" is not be construed as imposing any condition for any particular starting composition or method by which the affinity-modified IgSF domain was created. Thus, the affinity modified IgSF domains of the present disclosure are not limited to wild type IgF domains that are then transformed to an affinity modified IgSF domain by any particular process of affinity modification. An affinity modified IgSF domain polypeptide can, for example, be generated starting from wild type mammalian IgSF domain sequence information, then modeled in silico for binding to its cognate binding partner, and finally recombinantly or chemically synthesized to yield the affinity modified IgSF domain composition of matter. In but one alternative example, an affinity modified IgSF domain can be created by site-directed mutagenesis of a wild-type IgSF domain. Thus, affinity modified IgSF domain denotes a product and not necessarily a product produced by any given process. A variety of techniques including recombinant methods, chemical synthesis, or combinations thereof, may be employed.

"Binding" as used herein (e.g. with reference to binding of a T-cell modulatory multimeric polypeptide of the present disclosure to a polypeptide (e.g., a T-cell receptor) on a T-cell) refers to a non-covalent interaction between. Binding interactions are generally characterized by a dissociation constant (KD) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower KD.

The terms "binding affinity," and "binding avidity" as used herein means the specific binding affinity and specific binding avidity, respectively, of a protein for its counter-structure under specific binding conditions. In biochemical kinetics, avidity refers to the accumulated strength of multiple affinities of individual non-covalent binding interactions, such as between CD80 and its counter structures CTLA-4, PD-L1 and/or CD28. As such, avidity is distinct from affinity, which describes the strength of a single interaction. An increase or attenuation in binding affinity of a variant CD80 containing an affinity modified CD80 IgSF domain to its counter-structure is determined relative to the binding affinity of the unmodified CD80, such as an unmodified CD80 containing the native or wild-type IgSF domain, such as IgV or IgC domain. Methods for determining binding affinity or avidity are known in art. See, for example, Larsen et al., American Journal of Transplantation, Vol 5: 443-453 (2005). In some embodiments, a variant CD80 of the disclosure (i.e. a CD80-Fc fusion protein containing an affinity modified IgSF domain) specifically binds to CTLA-4, PD-L1 and/or CD28 measured by flow cytometry with a binding affinity that yields a Mean Fluorescence Intensity (MFI) value at least 10%, 20%, 30%, 40%, 50%, 60%, 70%, 80%, 90%, or 100% greater than a wild-type CD80 control in a binding assay.

The term "cognate binding partner" (used interchangeably with "counter-structure") in reference to a polypeptide, such as in reference to an IgSF domain of a variant CD80, refers to at least one molecule (typically a native mammalian protein) to which the referenced polypeptide specifically binds under specific binding conditions. In some aspects, a variant CD80 containing an affinity modified IgSF domain specifically binds to the counter-structure of the corresponding native or wild-type CD80 but with increased or attenuated affinity. A species of ligand recognized and specifically binding to its cognate receptor under specific binding conditions is an example of a counter-structure or cognate binding partner of that receptor. A "cognate cell surface binding partner" is a cognate binding partner expressed on a mammalian cell surface. A "cell surface molecular species" is a cognate binding partner of ligands of the immunological synapse (IS), expressed on and by cells, such as mammalian cells, forming the immunological synapse.

As used herein, "conjugate," "conjugation" or grammatical variations thereof refers the joining or linking together of two or more compounds resulting in the formation of another compound, by any joining or linking methods known in the art. It can also refer to a compound which is generated by the joining or linking together two or more compounds. For example, variant CD80 polypeptides linked directly or indirectly to one or more chemical moieties or polypeptide is an exemplary conjugate. Such conjugates include fusion proteins, those produced by chemical conjugates and those produced by any other methods.

The term "conservative amino acid substitution" as used herein means an amino acid substitution in which an amino acid residue is substituted by another amino acid residue having a side chain R group with similar chemical properties (e.g., charge or hydrophobicity). Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine, lysine-arginine, alanine-valine, glutamate-aspartate, and asparagine-glutamine.

"Co-stimulatory polypeptide," as the term is used herein, includes a polypeptide on an antigen presenting cell (APC) (e.g., a dendritic cell, a B cell, and the like) that specifically binds a cognate co-stimulatory polypeptide on a T-cell, thereby providing a signal which, in addition to the primary signal provided by, for instance, binding of a TCR/CD3 complex with a major histocompatibility complex (MHC) polypeptide loaded with peptide, mediates a T-cell response, including, but not limited to, proliferation, activation, differentiation, and the like.

The terms "decrease" or "attenuate" "or suppress" as used herein means to decrease by a statistically significant amount. A decrease can be at least 10%, 20%, 30%, 40%, 50%, 60%, 70%, 80%, 90%, or 100%.

The terms "derivatives" or "derivatized" refer to modification of a protein by covalently linking it, directly or indirectly, to a composition so as to alter such characteristics as biological half-life, bioavailability, immunogenicity, solubility, toxicity, potency, or efficacy while retaining or enhancing its therapeutic benefit. Derivatives of immunomodulatory polypeptides of the disclosure are within the scope of the present disclosure and can be made by, for example, glycosylation, pegylation, lipidation, or Fc-fusion.

As used herein, domain (typically a sequence of three or more, generally 5 or 7 or more amino acids, such as 10 to 200 amino acid residues) refers to a portion of a molecule, such as a protein or encoding nucleic acid, that is structurally and/or functionally distinct from other portions of the molecule and is identifiable. For example, domains include those portions of a polypeptide chain that can form an independently folded structure within a protein made up of one or more structural motifs and/or that is recognized by virtue of a functional activity, such as binding activity. A protein can have one, or more than one, distinct domains. For example, a domain can be identified, defined or distinguished by homology of the primary sequence or structure to related family members, such as homology to motifs. In another example, a domain can be distinguished by its function, such as an ability to interact with a biomolecule, such as a cognate binding partner. A domain independently can exhibit a biological function or activity such that the domain independently or fused to another molecule can perform an activity, such as, for example binding. A domain can be a linear sequence of amino acids or a non-linear sequence of amino acids. Many polypeptides contain a plurality of domains. Such domains are known, and can be identified by those of skill in the art. For exemplification herein, definitions are provided, but it is understood that it is well within the skill in the art to recognize particular domains by name. If needed appropriate software can be employed to identify domains.

The terms "effective amount" or "therapeutically effective amount" refer to a quantity and/or concentration of a therapeutic composition of the disclosure, including a protein composition or cell composition, that when administered ex vivo (by contact with a cell from a patient) or in vivo (by administration into a patient) either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. In the case of cell therapy, the effective amount is an effective dose or number of cells administered to a patient by adoptive cell therapy. In some embodiments the patient is a mammal such as a non-human primate or human patient.

The terms "enhanced" or "increased" as used herein in the context of increasing immunological activity of a mammalian lymphocyte means to increase one or more activities the lymphocyte. An increased activity can be one or more of increase cell survival, cell proliferation, cytokine production, or T-cell cytotoxicity, such as by a statistically significant amount. In some embodiments, reference to increased immunological activity means to induce IL-2 production in T-cell. In some embodiments, the immunological activity can be assessed by detection of IL-2 release. In some embodiments, reference to increased immunological activity means to increase interferon gamma (IFN-gamma) production, such as by a statistically significant amount. In some embodiments, the immunological activity can be assessed in a mixed lymphocyte reaction (MLR) assay. Methods of conducting MLR assays are known in the art. Wang et al., Cancer Immunol Res. 2014 September: 2(9):846-56. Other methods of assessing activities of lymphocytes are known in the art, including any assay as described herein. In some embodiments an enhancement can be an increase of at least 10%, 20%, 30%, 40%, 50%, 75%, 100%, 200%, 300%, 400%, or 500% greater than a non-zero control value.

The term "engineered cell" as used herein refers to a mammalian cell that has been genetically modified by human intervention such as by recombinant DNA methods or viral transduction. In some embodiments, the cell is an immune cell, such as a lymphocyte (e.g. T-cell, B cell, NK cell) or an antigen presenting cell (e.g. dendritic cell). The cell can be a primary cell from a patient or can be a cell line. In some embodiments, an engineered cell of the disclosure comprises a variant CD80 of the disclosure engineered to modulate immunological activity of a T-cell expressing CD28, PD-L1, or CTLA-4 to which the variant CD80 specifically binds. In some embodiments, the variant CD80 is a transmembrane immunomodulatory protein (hereinafter referred to as "TIP") containing the extracellular domain or a portion thereof containing the IgV and/or IgC domain linked to a transmembrane domain and, optionally, an intracellular signaling domain. In some cases, the TIP is formatted as a chimeric receptor containing a heterologous cytoplasmic signaling domain or endodomain. In some embodiments, an engineered cell is capable of expressing and secreting a immunomodulatory protein as described herein. Among provided engineered cells also are cells further containing an engineered T-cell receptor (TCR) or chimeric antigen receptor (CAR).

The term "engineered T-cell" as used herein refers to a T-cell such as a T helper cell, cytotoxic T-cell (alternatively, cytotoxic T lymphocyte or CTL), natural killer T-cell, regulatory T-cell, memory T-cell, or gamma delta T-cell, that has been genetically modified by human intervention such as by recombinant DNA methods or viral transduction methods. The term "engineered T-cell receptor" or "engineered TCR" refers to a T-cell receptor (TCR) engineered to specifically bind with a desired affinity to a major histocompatibility complex (MHC)/peptide target antigen that is selected, cloned, and/or subsequently introduced into a population of T-cells, often used for adoptive immunotherapy. In contrast to engineered TCRs, CARs are engineered to bind target antigens in a MHC independent manner.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T-cell, a natural killer cell, and the like. An immunological synapse between an APC and a T-cell is generally initiated by the interaction of a T-cell antigen receptor and major histocompatibility complex molecules, e.g., as described in Bromley et al., Annu Rev Immunol. 2001; 19:375-96; the disclosure of which is incorporated herein by reference in its entirety.

An Fc (fragment crystallizable) region or domain of an immunoglobulin molecule (also termed an Fc polypeptide) corresponds largely to the constant region of the immunoglobulin heavy chain, and is responsible for various functions, including the antibody's effector function(s). The Fc domain contains part or all of a hinge domain of an immunoglobulin molecule plus a CH2 and a CH3 domain. The Fc domain can form a dimer of two polypeptide chains joined by one or more disulfide bonds. In some embodiments, the Fc is a variant Fc that exhibits reduced (e.g. reduced greater than 30%, 40%, 50%, 60%, 70%, 80%, 90% or more)

activity to facilitate an effector function. In some embodiments, reference to amino acid substitutions in an Fc region is by EU numbering system unless described with reference to a specific SEQ ID NO: EU numbering is known and is according to the most recently updated IMGT Scientific Chart (IMGT®, the international ImMunoGeneTics information system®, webpage at imgt.org/IMGTScientific-Chart/Numbering/Hu_IGHGnber.html and the EU index as reported in Kabat, E. A. et al. Sequences of Proteins of Immunological interest. 5th ed. US Department of Health and Human Services, NIH publication No. 91-3242 (1991).

An immunoglobulin Fc fusion ("Fc-fusion"), such as an immunomodulatory Fc fusion protein, is a molecule comprising one or more polypeptides (or one or more small molecules) operably linked to an Fc region of an immunoglobulin. An Fc-fusion may comprise, for example, the Fc region of an antibody (which facilitates effector functions and pharmacokinetics) and a variant CD80. An immunoglobulin Fc region may be linked indirectly or directly to one or more variant CD80 or small molecules (fusion partners). Various linkers are known in the art and can optionally be used to link an Fc to a fusion partner to generate an Fc-fusion. Fc-fusions of identical species can be dimerized to form Fc-fusion homodimers, or using non-identical species to form Fc-fusion heterodimers. In some embodiments, the Fc is a mammalian Fc such as a murine or human Fc.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

"Heterologous," as used herein, means a nucleotide or polypeptide that is not found in the native nucleic acid or protein, respectively.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a multimeric polypeptide of the present disclosure), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. The term "host cell" refers to a cell that can be used to express a protein encoded by a recombinant expression vector. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include Chinese hamster ovary (CHO) cells or their derivatives such as Veggie CHO and related cell lines which grow in serum-free media or CHO strain DX-B 11, which is deficient in DHFR. In some embodiments, a host cell is a mammalian cell (e.g., a human cell, a monkey cell, a hamster cell, a rat cell, a mouse cell, or an insect cell).

The term "immunoglobulin" (abbreviated "Ig") as used herein refers to a mammalian immunoglobulin protein including any of the five human classes of antibody: IgA (which includes subclasses IgA1 and IgA2), IgD, IgE, IgG (which includes subclasses IgG1, IgG2, IgG3, and IgG4), and IgM. The term is also inclusive of immunoglobulins that are less than full-length, whether wholly or partially synthetic (e.g., recombinant or chemical synthesis) or naturally produced, such as antigen binding fragment (Fab), variable fragment (Fv) containing VH and VL, the single chain variable fragment (scFv) containing VH and VL linked together in one chain, as well as other antibody V region fragments, such as Fab', F(ab)2, F(ab')2, dsFv diabody, Fc, and Fd polypeptide fragments. Bispecific antibodies, homobispecific and heterobispecific, are included within the meaning of the term.

The term "immunoglobulin superfamily" or "IgSF" as used herein means the group of cell surface and soluble proteins that are involved in the recognition, binding, or adhesion processes of cells. Molecules are categorized as members of this superfamily based on shared structural features with immunoglobulins (i.e., antibodies); they all possess a domain known as an immunoglobulin domain or fold. Members of the IgSF include cell surface antigen receptors, co-receptors and co-stimulatory molecules of the immune system, molecules involved in antigen presentation to lymphocytes, cell adhesion molecules, certain cytokine receptors and intracellular muscle proteins. They are commonly associated with roles in the immune system. Proteins in the immunological synapse are often members of the IgSF. IgSF can also be classified into "subfamilies" based on shared properties such as function. Such subfamilies typically consist of from 4 to 30 IgSF members.

The terms "IgSF domain" or "immunoglobulin domain" or "Ig domain" as used herein refers to a structural domain of IgSF proteins. Ig domains are named after the immunoglobulin molecules. They contain about 70-110 amino acids and are categorized according to their size and function. Ig-domains possess a characteristic Ig-fold, which has a sandwich-like structure formed by two sheets of antiparallel beta strands. Interactions between hydrophobic amino acids on the inner side of the sandwich and highly conserved disulfide bonds formed between cysteine residues in the B and F strands, stabilize the Ig-fold. One end of the Ig domain has a section called the complementarity determining region that is important for the specificity of antibodies for their ligands. The Ig like domains can be classified (into classes) as: IgV, IgC1, IgC2, or IgI. Most Ig domains are either variable (IgV) or constant (IgC). IgV domains with 9 beta strands are generally longer than IgC domains with 7 beta strands. Ig domains of some members of the IgSF resemble IgV domains in the amino acid sequence, yet are similar in size to IgC domains. These are called IgC2 domains, while standard IgC domains are called IgC1 domains. T-cell receptor (TCR) chains contain two Ig domains in the extracellular portion; one IgV domain at the N-terminus and one IgC1 domain adjacent to the cell membrane. CD80 contains two Ig domains: IgV and IgC.

The term "IgSF species" as used herein means an ensemble of IgSF member proteins with identical or substantially identical primary amino acid sequence. Each mammalian immunoglobulin superfamily (IgSF) member defines a unique identity of all IgSF species that belong to that IgSF member. Thus, each IgSF family member is unique from other IgSF family members and, accordingly, each species of a particular IgSF family member is unique from the species of another IgSF family member. Nevertheless, variation between molecules that are of the same IgSF species may occur owing to differences in post-translational modification such as glycosylation, phosphorylation, ubiquitination, nitrosylation, methylation, acetylation, and lipidation. Additionally, minor sequence differences within a single IgSF species owing to gene polymorphisms constitute another form of variation within a single IgSF species as do wild type truncated forms of IgSF species owing to, for example, proteolytic cleavage. A "cell surface IgSF species" is an IgSF species expressed on the surface of a cell, generally a mammalian cell.

An "immunomodulatory polypeptide" is a polypeptide that modulates immunological activity. By "modulation" or "modulating" an immune response is meant that immunological activity is either increased or decreased. An immunomodulatory polypeptide can be a single polypeptide chain or a multimer (dimers or higher order multimers) of at least two polypeptide chains covalently bonded to each other by, for example, interchain disulfide bonds. Thus, monomeric, dimeric, and higher order multimeric polypeptides are within the scope of the defined term. Multimeric polypeptides can be homomultimeric (of identical polypeptide chains) or heteromultimeric (of non-identical polypeptide chains). An immunomodulatory polypeptide of the disclosure comprises a variant CD80.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

The term "lymphocyte" as used herein means any of three subtypes of white blood cell in a mammalian immune system. They include natural killer cells (NK cells) (which function in cell-mediated, cytotoxic innate immunity), T-cells (for cell-mediated, cytotoxic adaptive immunity), and B cells (for humoral, antibody-driven adaptive immunity). T-cells include: T helper cells, cytotoxic T-cells, natural killer T-cells, memory T-cells, regulatory T-cells, or gamma delta T-cells. Innate lymphoid cells (ILC) are also included within the definition of lymphocyte.

The terms "mammal," or "patient" specifically includes reference to at least one of a: human, chimpanzee, rhesus monkey, cynomolgus monkey, dog, cat, mouse, or rat. A "modulatory domain" or "immunomodulatory domain" of a T-cell modulatory multimeric polypeptide of the present disclosure comprises a co-stimulatory polypeptide.

The terms "modulating" or "modulate" as used herein in the context of an immune response, such as a mammalian immune response, refer to any alteration, such as an increase or a decrease, of existing or potential immune responses that occurs as a result of administration of an immunomodulatory polypeptide comprising a variant CD80 of the present disclosure or as a result of administration of engineered cells expresses an immunomodulatory protein, such as a variant CD80 transmembrane immunomodulatory protein of the present disclosure. Thus, it refers to an alteration, such as an increase or decrease, of an immune response as compared to the immune response that occurs or is present in the absence of the administration of the immunomodulatory protein comprising the variant CD80 or cells expressing such an immunomodulatory polypeptide. Such modulation includes any induction, activation, suppression or alteration in degree or extent of immunological activity of an immune cell. Immune cells include B cells, T-cells, NK (natural killer) cells, NK T-cells, professional antigen-presenting cells (APCs), and non-professional antigen-presenting cells, and inflammatory cells (neutrophils, macrophages, monocytes, eosinophils, and basophils). Modulation includes any change imparted on an existing immune response, a developing immune response, a potential immune response, or the capacity to induce, regulate, influence, or respond to an immune response. Modulation includes any alteration in the expression and/or function of genes, proteins and/or other molecules in immune cells as part of an immune response. Modulation of an immune response or modulation of immunological activity includes, for example, the following: elimination, deletion, or sequestration of immune cells; induction or generation of immune cells that can modulate the functional capacity of other cells such as autoreactive lymphocytes, antigen presenting cells, or inflammatory cells; induction of an unresponsive state in immune cells (i.e., anergy); enhancing or suppressing the activity or function of immune cells, including but not limited to altering the pattern of proteins expressed by these cells. Examples include altered production and/or secretion of certain classes of molecules such as cytokines, chemokines, growth factors, transcription factors, kinases, costimulatory molecules, or other cell surface receptors or any combination of these modulatory events. Modulation can be assessed, for example, by an alteration of a binding affinity and/or avidity of a variant CD80 to counter structures CTLA-4, PD-L1 or CD28. Modulation can be assessed, for example, by an alteration in IL-2 expression or release in T-cells relative to the wild-type CD80 control. Modulation can be assessed, for example, by an alteration in IFN-gamma (interferon gamma) expression relative to the wild-type CD80 control in a primary T-cell assay (see, Zhao and Ji, Exp Cell Res. 2016 Jan. 1; 340(1) 132-138). Modulation can be assessed, for example, by an alteration of an immunological activity of engineered cells, such as an alteration in in cytotoxic activity of engineered cells or an alteration in cytokine secretion of engineered cells relative to cells engineered with a wild-type CD80 transmembrane protein.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. Unless specifically limited, the terms encompass nucleic acids containing known analogues of natural nucleotides and that have similar binding properties to it and are metabolized in a manner similar to naturally-occurring nucleotides. Unless otherwise indicated, a particular nucleic acid sequence also implicitly encompasses conservatively modified variants thereof (e.g., degenerate codon substitutions) and complementary nucleotide sequences as well as the sequence explicitly indicated (a "reference sequence"). Specifically, degenerate codon substitutions may be achieved by generating sequences in which the third position of one or more selected (or all) codons is substituted with mixed-base and/or deoxyinosine residues. The term nucleic acid or polynucleotide encompasses cDNA or mRNA encoded by a gene.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The terms include post-translational modifications of the polypeptide, for example, glycosylations, acetylations, sialylations, phosphorylations and the like. The terms also include molecules in which one or more amino acid analogs or non-canonical or unnatural amino acids are included as can be synthesized, or expressed recombinantly using known protein engineering techniques. In addition, proteins can be derivatized.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. For example, a "recombinant nucleic acid" is one that is made by recombining nucleic acids, e.g., during cloning, affinity modification, DNA shuffling or other well-known molecular biological procedures. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid or that is otherwise altered by genetic engineering, such as by introducing into the cell a nucleic acid molecule encoding a recombinant protein, such as a transmembrane immunomodulatory protein provided herein. For example, a genetically modified eukaryotic host cell is genetically modified by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell. Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. The terms "in operable combination," "in operable order" and "operably linked" as used herein refer to the linkage of nucleic acid sequences in such a manner or orientation that a nucleic acid molecule capable of directing the transcription of a given gene and/or the synthesis of a desired protein molecule is produced.

The terms "recombinant expression vector," or "DNA construct" are used interchangeably herein to refer to a DNA molecule comprising a vector and one insert. Recombinant expression vectors are usually generated for the purpose of expressing and/or propagating the insert(s) and/or the expression cassette, or for the construction of other recombinant nucleotide sequences. The recombinant expression vector refers to a DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the recombinant expression vector, operably linked to the coding sequence for the recombinant protein, such as a recombinant fusion protein, so that the expressed fusion protein can be secreted by the recombinant host cell, for easier isolation of the fusion protein from the cell, if desired. The term includes the vector as a self-replicating nucleic acid structure as well as the vector incorporated into the genome of a host cell into which it has been introduced. Among the vectors are viral vectors, such as lentiviral vectors.

"T-cell" includes all types of immune cells expressing CD3, including T-helper cells (CD4+ cells), cytotoxic T-cells (CD8+ cells), T-regulatory cells (Treg), and NK-T-cells.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy can desirably be administered during the symptomatic stage of the disease, and in some cases after the symptomatic stage of the disease. "Treating," "treatment," or "therapy" also means a decrease in the severity of symptoms in an acute or chronic disease or disorder or a decrease in the relapse rate as for example in the case of a relapsing or remitting autoimmune disease course or a decrease in inflammation in the case of an inflammatory aspect of an autoimmune disease. As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS). "Preventing," "prophylaxis," or "prevention" of a disease or disorder as used in the context of this disclosure refers to the administration of an immunomodulatory polypeptide or engineered cells of the disclosure, either alone or in combination with another compound, to prevent the occurrence or onset of a disease or disorder or some or all of the symptoms of a disease or disorder or to lessen the likelihood of the onset of a disease or disorder.

The term "variant" (also "mutant", "mutated" or "modified") as used in reference to a variant CD80 means a CD80, such as a mammalian (e.g., human or murine) CD80 created by human intervention. The variant CD80 is a polypeptide having an altered amino acid sequence, relative to an unmodified or wild-type CD80. The variant CD80 is a polypeptide which differs from a wild-type CD80 isoform sequence by one or more amino acid substitutions, deletions, additions, or combinations thereof. For purposes herein, the variant CD80 contains at least one affinity modified domain, whereby one or more of the amino acid differences occurs in an IgSF domain (e.g. IgC domain and/or IgV domain). A variant CD80 can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid differences, such as amino acid substitutions. The variant CD80 polypeptides generally exhibit at least 50%, 60%, 70%, 80%, 85%, 86%, 87%, 88%, 89%, 90%, 91%, 92%, 93%, 94%, 95%, 96%, 97%, 98%, 99% or more sequence identity to a wild-type or unmodified CD80 extracellular domain (SEQ ID NO: 1). Non-naturally occurring amino acids as well as naturally occurring amino acids are included within the scope of permissible substitutions or additions. A variant CD80 is not limited to any particular method of making and includes, for example, de novo chemical synthesis, de novo recombinant DNA techniques, or combinations thereof. A variant CD80 of the disclosure specifically binds to at least one or more of: CD28, PD-L1, or CTLA-4 of a mammalian species. In some embodiments, the altered amino acid sequence results in an altered (i.e., increased or decreased) binding affinity or avidity to CD28, PD-L1, or CTLA-4 compared to the wild-type CD80 protein. An increase or decrease in binding affinity or avidity can be determined using well known binding assays such as flow cytometry. Larsen et al., American Journal of Transplantation, Vol 5: 443-453 (2005). See also, Linsley et al., Immunity, 1: 7930801 (1994). An increase in variant CD80 binding affinity or avidity to CD28, PD-L1, or CTLA-4 is to a value at least 5% greater than that of the wild-type CD80 control value and in some embodiments, at least 10%, 15%, 20%, 30%, 40%, 50%, 100% greater than that of the wild-type CD80 control value. A decrease in CD80 binding affinity or avidity to CD28, PD-L1, or CTLA-4 is to a value no greater than 95% of the of the wild-type CD80 control value, and in some embodiments no greater than 80%, 70% 60%, 50%, 40%, 30%, 20%, 10%, 5%, or no detectable binding affinity or avidity of the wild-type CD80 control value. A variant CD80 is altered in primary amino acid sequence by substitution, addition, or deletion of amino acid residues. The term "variant" in the context of variant CD80 is not be construed as imposing any condition for any particular starting composition or method by which the variant CD80 is created. A variant CD80 can, for example, be generated starting from wild type mammalian CD80 sequence information, then modeled in silico for binding to CD28, PD-L1, or CTLA-4, and finally recombinantly or chemically synthesized to yield a variant CD80 of the present disclosure. In alternative embodiment, a variant CD80 can be created by site-directed mutagenesis of a wild-type CD80. Thus, variant CD80 denotes a composition and not necessarily a product produced by any given process. A variety of techniques including recombinant methods, chemical synthesis, or combinations thereof, may be employed.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a multimeric polypeptide" includes a plurality of such multimeric polypeptides and reference to "the modulatory domain" includes reference to one or more modulatory domains and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

II. Variant CD80 Polypeptides

The present disclosure provides variant CD80 polypeptides that exhibit altered (increased or decreased) binding activity or affinity for one or more of a CD80 cognate binding partner. In some embodiments, the CD80 cognate binding partner is CD28, PD-L1, or CTLA-4. In some embodiments, the variant CD80 polypeptide contains one or more amino acids modifications, such as one or more substitutions (alternatively, "mutations" or "replacements"), deletions or addition, in an immunoglobulin superfamily (IgSF) domain (IgD) relative to a wild-type or unmodified CD80 polypeptide or a portion of a wild-type or unmodified CD80 containing an immunoglobulin superfamily (IgSF) domain or a specific binding fragment thereof. Thus, a provided variant CD80 polypeptide is or comprises a variant IgD (hereinafter called "vIgD") in which the one or more amino acid modifications (e.g. substitutions) is in an IgD.

In some embodiments, the IgD comprises an IgC domain or an IgV domain or specific binding fragment of the IgC domain or the IgV domain, or combinations thereof. In some embodiments, the IgD can be an IgC only, the combination of the IgC and IgV, including the entire extracellular domain (ECD), or any combination of Ig domains of CD80. Table 1 provides exemplary residues that correspond to the IgC domain of CD80.

The IgC domain of CD80 does not directed interact with CD80's binding partners. The present inventors employed structural-based rational design to select positions within the IgC domain of CD80 for mutagenesis. These selected positions are located near the interdomain between the IgV and IgC and are in the vicinity of the flexible hinge region. Mutations in this region could potentially force changes in the IgC's tertiary structure and hence affect CD80 dimer configuration.

The present inventors choose to mutate amino-acid residues in the IgC domain which does not directly interacts with the target proteins upon binding. They rationally designed mutations in the IgC domain that would alter the conformation and/or the dynamics of the whole mutant protein, and then through which, to modulate its binding affinities towards the target proteins and/or its biological functions when interacting with the target proteins, for example, to modulate the function of the mutant protein towards CD28 activation. Through this approach, the present inventors achieved selectively changing the binding affinity or function of the CD80 protein with the selected target protein while leaving the interaction with one of another target protein or the other two target proteins minimally affected. For example, through rational design, the present inventors have obtained mutants that have a range of activity towards CD28 activation while maintaining similar binding affinity towards CTLA-4. For example, A165F had very low CD28 activation compared to wt CD80, yet its binding affinity towards CTLA-4 (binding assay by FACS, EC50=0.046 uM vs EC50=0.014 uM wt CD80) and PD-L1 (ELISA assay, EC50=0.38 uM vs EC50=0.98 uM wt CD80) were similar; S131I had similar CD28 activation (IL-2 release assay, EC50=1.13 uM vs EC50=0.94 uM wt CD80) and binding affinity towards CTLA-4 (binding assay by FACS, EC50=0.028 uM vs EC50=0.014 uM wt CD80) compared to wt CD80, yet its binding affinity towards PD-L1 was four-fold higher than the wt CD80 (ELISA assay, EC50=0.24 uM vs EC50=0.98 uM wt CD80).

In some embodiments, the variant is modified in one more IgSF domains relative to the sequence of an unmodified CD80 sequence. In some embodiments, the unmodified CD80 sequence is a wild-type CD80. In some embodiments, the unmodified or wild-type CD80 has the sequence of a native CD80 or an ortholog thereof. In some embodiments, the unmodified CD80 is or comprises the extracellular domain (ECD) of CD80 or a portion thereof containing one or more IgSF domain. In some embodiments, the extracellular domain of an unmodified or wild-type CD80 polypeptide comprises an IgC domain and/or an IgV domain. However, the variant CD80 polypeptide need not comprise both the IgC domain and the IgV domain. In some embodiments, the variant CD80 polypeptide comprises or consists essentially of the IgC domain or a specific binding fragment thereof. In some embodiments, the variant CD80 polypeptide comprises or consists essentially of the IgV domain or specific binding fragments thereof. In some embodiments, the variant CD80 is soluble and lacks a transmembrane domain. In some embodiments, the variant CD80 further comprises a transmembrane domain and, in some cases, also a cytoplasmic domain.

In some embodiments, the wild-type or unmodified CD80 sequence is a mammalian CD80 sequence. In some embodiments, the wild-type or unmodified CD80 sequence can be a mammalian CD80 that includes, but is not limited to, human, mouse, cynomolgus monkey, or rat. In some embodiments, the wild-type or unmodified CD80 sequence is human.

In some embodiments, variant CD80 polypeptides comprise an amino acid sequence having at least 80% amino acid sequence identity to SEQ ID NO: 1, wherein the variant CD80 polypeptide comprises one or more of the amino acid substitution modifications compared to SEQ ID NO: 1, wherein the one or more substitution modifications are at positions 131, 139, 155, 165, or 166 of SEQ ID NO: 1. In some embodiments, the amino acid substitution modification is any of the 20 amino acids other than the corresponding wild type amino acid in SEQ ID NO: 1.

The variant CD80 polypeptides generally exhibit at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified CD80, a mature sequence thereof or a portion thereof containing the extracellular domain or an IgSF domain thereof set forth in SEQ ID NO: 1. In some embodiments, the variant CD80 polypeptides exhibit at least 50%, 60%, 70%, 80%, 85%, 86%, 87%, 88%, 89%, 90%, 91%, 92%, 93%, 94%, 95%, 96%, 97%, 98%, 99% or more sequence identity to a corresponding wild-type or unmodified CD80 comprising the sequence set forth in SEQ ID NO: 1.

In some embodiments, the specific binding fragment of the IgC domain contains an amino acid sequence that has at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% sequence identity to of a corresponding wild-type or unmodified IgC domain.

In some embodiments, the specific binding fragment of the IgV domain contains an amino acid sequence that has at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9% sequence identity to of a corresponding wild-type or unmodified IgV domain.

In any of such embodiments, the one or more amino acid modifications (e.g. substitutions) of the variant CD80 polypeptides can be located in any one or more of the CD80 polypeptide domains. For example, in some embodiments, one or more amino acid substitutions are located in the extracellular domain of the variant CD80 polypeptide. In some embodiments, one or more amino acid substitutions are located in the IgC domain or specific binding fragment of the IgC domain. In some embodiments, one or more amino acid modifications (e.g. substitutions) are located in the IgV domain or specific binding fragment of the IgV domain.

In other embodiments, the variant CD80 polypeptide further comprises a second polypeptide that is capable of dimerizing. In some embodiments, the second polypeptide is an immunoglobulin Fc domain. In some embodiments, the immunoglobulin Fc domain is a human IgG1 Fc domain, a human IgG2 Fc domain, a human IgG3 Fc domain, or a human IgG4 Fc domain. In some embodiments, the immunoglobulin Fc domain is a mouse IgG1 Fc domain, a mouse IgG2a Fc domain, a mouse IgG2b Fc domain, or a mouse IgG3 Fc domain. In some embodiments, the variant CD80 polypeptide further comprises a therapeutically active moiety.

In some embodiments, provided herein is a polynucleotide encoding the variant CD80 polypeptide of the present disclosure. In some embodiments, the polynucleotide is a synthetic nucleic acid. In some embodiments, the polynucleotide is cDNA. In some embodiments, the polynucleotide is operably linked to a transcriptional control element. In some embodiments, the transcriptional control element is a promoter that is functional in a eukaryotic cell.

In other embodiments, provided herein is a vector comprising the polynucleotide of the present disclosure. In some embodiments, the vector is an expression vector. In some embodiments, the vector is a mammalian vector or a viral vector.

Generally, each of the various attributes of polypeptides are separately disclosed below (e.g., soluble, secretable and membrane bound polypeptides, affinity of CD80 for CD28, PD-L1, and CTLA-4, number of variations per polypeptide chain, number of linked polypeptide chains, the number and nature of amino acid alterations per variant CD80, etc.). However, as will be clear to the skilled artisan, any particular polypeptide can comprise a combination of these independent attributes. It is understood that reference to amino acids, including to a specific sequence set forth as a SEQ ID NO used to describe domain organization of an IgSF domain are for illustrative purposes and are not meant to limit the scope of the embodiments provided. It is understood that polypeptides and the description of domains thereof are theoretically derived based on homology analysis and alignments with similar molecules. Thus, the exact locus can vary, and is not necessarily the same for each protein. Hence, the specific IgSF domain, such as specific IgC domain or IgV domain, can be several amino acids (such as one, two, three or four) longer or shorter.

Further, various embodiments of the disclosure as discussed below are frequently provided within the meaning of a defined term as disclosed above. The embodiments described in a particular definition are therefore to be interpreted as being incorporated by reference when the defined term is utilized in discussing the various aspects and attributes described herein. Thus, the headings, the order of presentation of the various aspects and embodiments, and the separate disclosure of each independent attribute is not meant to be a limitation to the scope of the present disclosure.

Exemplary Modifications

In some embodiments, the amino acid substitution modification at position 131 of SEQ ID NO: 1 is S131A, S131V, S131I, S131F, S131R, S131E, S131D, or S131Q. In some embodiments, the amino acid substitution modification at position 139 of SEQ ID NO: 1 is L139V. In some embodiments, the amino acid substitution modification at position 155 of SEQ ID NO: 1 is V155A, V155I, or V155T. In some embodiments, the amino acid substitution modification at position 165 of SEQ ID NO: 1 is A165S, A165V, A165I, A165F, A165R, A165E, A165D, or A165Q. In some embodiments, the amino acid substitution modification at position 166 of SEQ ID NO: 1 is V166A, V166L, or V166T.

In some embodiments, the variant CD80 polypeptide comprises two or more of the amino acid substitution modifications compared to SEQ ID NO: 1, and wherein the two or more substitution modifications are at positions 130, 131, 139, 155, 156, 165, or 166 of SEQ ID NO: 1. In some embodiments, the variant CD80 polypeptide comprises two amino acid substitution modifications V166L and L139V. In some embodiments, the variant CD80 polypeptide comprises two amino acid substitution modifications S156A and V155A. In some embodiments, the variant CD80 polypeptide comprises two amino acid substitution modifications S156A and V155I. In some embodiments, the variant CD80 polypeptide comprises two amino acid substitution modifications S156A and V155T. In some embodiments, the variant CD80 polypeptide comprises two amino acid substitution modifications S156A and T130A. In some embodiments, the variant CD80 polypeptide comprises two amino acid substitution modifications S156A and V166A. In some embodiments, the variant CD80 polypeptide comprises two amino acid substitution modifications S156I and A165S. In some embodiments, the variant CD80 polypeptide comprises two amino acid substitution modifications S156I and S131A. In some embodiments, the variant CD80 polypeptide comprises two amino acid substitution modifications A165S and S131A.

In some embodiments, the variant CD80 polypeptide comprises three or more of the amino acid substitution modifications compared to SEQ ID NO: 1, and wherein the three or more substitution modifications are at positions 130, 131, 139, 155, 156, 165, or 166 of SEQ ID NO: 1. In some embodiments, the variant CD80 polypeptide comprises three amino acid substitution modifications S156A, V166L and L139V. In some embodiments, the variant CD80 polypeptide comprises three amino acid substitution modifications S156I, A165S and S131A.

In some embodiments, the variant CD80 polypeptide comprises four or more of the amino acid substitution modifications compared to SEQ ID NO: 1, and wherein the four or more substitution modifications are at positions 130, 131, 139, 155, 156, 165, or 166 of SEQ ID NO: 1. In some embodiments, the variant CD80 polypeptide comprises five or more of the amino acid substitution modifications compared to SEQ ID NO: 1, and wherein the five or more substitution modifications are at positions 130, 131, 139, 155, 156, 165, or 166 of SEQ ID NO: 1.

In some embodiments, the variant CD80 polypeptide has increased or decreased binding affinity for CTLA-4 compared to SEQ ID NO: 1. In some embodiments, the variant CD80 polypeptide has increased or decreased binding affinity for CD28 compared to SEQ ID NO: 1. In some embodiments, the variant CD80 polypeptide has increased or decreased binding affinity for PD-L1 compared to SEQ ID NO: 1.

In some embodiments, a variant CD80 polypeptide of the disclosure is sialylated.

Provided herein are variant CD80 polypeptides containing at least one affinity-modified IgSF domain (e.g. IgC or IgV) or a specific binding fragment thereof in an IgSF domain contained in a wild-type or unmodified CD80 polypeptide such that the variant CD80 polypeptide exhibits altered (increased or decreased) binding activity or affinity for one or more ligands CD28, PD-L1, or CTLA-4 compared to a wild-type or unmodified CD80 polypeptide. In some embodiments, the variant CD80 polypeptides have a binding affinity for CD28, PD-L1, and/or CTLA-4 that differs from that of a wild-type or unmodified CD80 polypeptide control sequence as determined by, for example, solid-phase ELISA immunoassays, flow cytometry or Biacore assays. In some embodiments, the variant CD80 polypeptide has an increased binding affinity for CD28, PD-L1, and/or CTLA-4. In some embodiments, the variant CD80 polypeptide has a decreased binding affinity for CD28, PD-L1, and/or CTLA-4, relative to a wild-type or unmodified CD80 polypeptide. The CD28, PD-L1, and/or the CTLA-4 can be a mammalian protein, such as a human protein or a murine protein.

Binding affinities for each of the cognate binding partners are generally independent; that is, in some embodiments, the variant CD80 polypeptide has an increased binding affinity for one, two or three of CD28, PD-L1, and/or CTLA-4, and a decreased binding affinity for one, two or three of CD28, PD-L1, and CTLA-4, relative to a wild-type or unmodified CD80 polypeptide.

In some embodiments, the variant CD80 polypeptide has an increased binding affinity for CD28, relative to a wild-type or unmodified CD80 polypeptide. In some embodiments, the variant CD80 polypeptide has an increased binding affinity for PD-L1, relative to a wild-type or unmodified CD80 polypeptide. In some embodiments, the variant CD80 polypeptide has an increased binding affinity for CTLA-4, relative to a wild-type or unmodified CD80 polypeptide. In some embodiments, the variant CD80 polypeptide has a decreased binding affinity for CD28, relative to a wild-type or unmodified CD80 polypeptide. In some embodiments, the variant CD80 polypeptide has a decreased binding affinity for PD-L1, relative to a wild-type or unmodified CD80 polypeptide. In some embodiments, the variant CD80 polypeptide has a decreased binding affinity for CTLA-4, relative to a wild-type or unmodified CD80 polypeptide.

In some embodiments, the variant CD80 polypeptide has an increased binding affinity for CD28 and PD-L1, relative to a wild-type or unmodified CD80 polypeptide. In some embodiments, the variant CD80 polypeptide has an increased binding affinity for CD28 and a decreased binding affinity for PD-L1, relative to a wild-type or unmodified CD80 polypeptide. In some embodiments, the variant CD80 polypeptide has a decreased binding affinity for CD28 and PD-L1, relative to a wild-type or unmodified CD80 polypeptide. In some embodiments, the variant CD80 polypeptide has a decreased binding affinity for CD28 and an increased binding affinity for PD-L1, relative to a wild-type or unmodified CD80 polypeptide.

In some embodiments, the variant CD80 polypeptide has an increased binding affinity for CD28 and CTLA-4, relative to a wild-type or unmodified CD80 polypeptide. In some embodiments, the variant CD80 polypeptide has an increased binding affinity for CD28 and a decreased binding affinity for CTLA-4, relative to a wild-type or unmodified CD80 polypeptide. In some embodiments, the variant CD80 polypeptide has a decreased binding affinity for CD28 and CTLA-4, relative to a wild-type or unmodified CD80 polypeptide. In some embodiments, the variant CD80 polypeptide has a decreased binding affinity for CD28 and an increased binding affinity for CTLA-4, relative to a wild-type or unmodified CD80 polypeptide.

In some embodiments, the variant CD80 polypeptide has an increased binding affinity for PD-L1 and CTLA-4, relative to a wild-type or unmodified CD80 polypeptide. In some embodiments, the variant CD80 polypeptide has an increased binding affinity for PD-L1 and a decreased binding affinity for CTLA-4, relative to a wild-type or unmodified CD80 polypeptide. In some embodiments, the variant CD80 polypeptide has a decreased binding affinity for PD-L1 and CTLA-4, relative to a wild-type or unmodified CD80 polypeptide. In some embodiments, the variant CD80 polypeptide has a decreased binding affinity for PD-L1 and an increased binding affinity for CTLA-4, relative to a wild-type or unmodified CD80 polypeptide.

In some embodiments, the variant CD80 polypeptide has an increased binding affinity for CD28, PD-L1, and CTLA-4, relative to a wild-type or unmodified CD80 polypeptide. In some embodiments, the variant CD80 polypeptide has a decreased binding affinity for CD28, PD-L1, and CTLA-4, relative to a wild-type or unmodified CD80 polypeptide.

In some embodiments, the variant CD80 polypeptide has an increased binding affinity for CD28 and PD-L1, and a decreased binding affinity for CTLA-4, relative to a wild-type or unmodified CD80 polypeptide. In some embodiments, the variant CD80 polypeptide has a decreased binding affinity for CD28 and PD-L1, and an increased binding affinity for CTLA-4, relative to a wild-type or unmodified CD80 polypeptide. In some embodiments, the variant CD80 polypeptide has an increased binding affinity for CD28 and CTLA-4, and a decreased binding affinity for PD-L1, relative to a wild-type or unmodified CD80 polypeptide. In some embodiments, the variant CD80 polypeptide has an decreased binding affinity for CD28 and CTLA-4, and an increased binding affinity for PD-L1, relative to a wild-type or unmodified CD80 polypeptide. In some embodiments, the variant CD80 polypeptide has an increased binding affinity for PD-L1 and CTLA-4, and a decreased binding affinity for CD28, relative to a wild-type or unmodified CD80 polypeptide. In some embodiments, the variant CD80 polypeptide has an decreased binding affinity for PD-L1 and CTLA-4, and an increased binding affinity for CD28, relative to a wild-type or unmodified CD80 polypeptide.

In some embodiments, variant CD80 polypeptides with increased or greater binding affinity to CD28, PD-L1, and/or CTLA-4 exhibit an increase in binding affinity relative to the wild-type or unmodified CD80 polypeptide control of at least about 5%, such as at least about 10%, 15%, 20%, 30%, 40%, 50%, 60%, 70%, 80%, 90% or more for the CD28, PD-L1, and/or CTLA-4. In some embodiments, the increase in binding affinity relative to the wild-type or unmodified CD80 polypeptide is more than 1.2-fold, 1.5-fold, 2-fold, 3-fold, 4-fold, 5-fold, 6-fold, 7-fold, 8-fold, 9-fold, 10-fold, 20-fold, 30-fold, 40-fold or 50-fold. In such examples, the wild-type or unmodified CD80 polypeptide has the same sequence as the variant CD80 polypeptide except that it does not contain the one or more amino acid modifications (e.g. substitutions).

In some embodiments, variant CD80 polypeptides with reduced or decreased binding affinity to CD28, PD-L1, and/or CTLA-4 have decrease in binding affinity relative to the wild-type or unmodified CD80 polypeptide control of at least 5%, such as at least about 10%, 15%, 20%, 30%, 40%, 50%, 60%, 70%, 80%, 90% or more for the CD28, PD-L1, and/or CTLA-4. In some embodiments, the decrease in binding affinity relative to the wild-type or unmodified CD80 polypeptide is more than 1.2-fold, 1.5-fold, 2-fold, 3-fold, 4-fold, 5-fold, 6-fold, 7-fold, 8-fold, 9-fold, 10-fold, 20-fold, 30-fold 40-fold or 50-fold. In such examples, the wild-type or unmodified CD80 polypeptide has the same sequence as the variant CD80 polypeptide except that it does not contain the one or more amino acid modifications, e.g. substitutions.

In some embodiments, the equilibrium dissociation constant (Kd) of any of the foregoing embodiments to CD28, PD-L1, and/or CTLA-4 can be less than $1 \times 10^{-5}$ M, $1 \times 10^{-6}$ M, $1 \times 10^{-7}$ M, $1 \times 10^{-8}$ M, $1 \times 10^{-9}$ M, $1 \times 10^{-10}$ M or $1 \times 10^{-11}$ M, or $1 \times 10^{-12}$ M.

In some embodiments, variant CD80 polypeptides have an increased or greater binding affinity to CD28. In some embodiments, variant CD80 polypeptides with increased or greater binding affinity to CD28 have an increase in binding affinity relative to the wild-type or unmodified CD80 polypeptide control of at least about 5%, such as at least about 10%, 15%, 20%, 30%, 40%, 50%, 60%, 70%, 80%, 90% or more for CD28. In some embodiments, variant CD80 polypeptides with increased or greater binding affinity to CD28 have an equilibrium dissociation constant (Kd) of less than 200 pM, 300 pM, 400 pM, 500 pM, or 600 pM for CD28. In some embodiments, the variant polypeptide specifically binds to the ectodomain of one of CD28 with increased selectivity compared to the unmodified CD80. In some embodiments, the increased selectivity is for CD28.

In some embodiments, variant CD80 polypeptides have an increased or greater binding affinity to PD-L1. In some embodiments, variant CD80 polypeptides with increased or greater binding affinity to PD-L1 have an increase in binding affinity relative to the wild-type or unmodified CD80 polypeptide control of at least about 5%, such as at least about 10%, 15%, 20%, 30%, 40%, 50%, 60%, 70%, 80%, 90% or more for PD-L1. In some embodiments, variant CD80 polypeptides with increased or greater binding affinity to PD-L1 have an equilibrium dissociation constant (Kd) of less than 200 pM, 300 pM, 400 pM, 500 pM, or 600 pM for PD-L1. In some embodiments, the variant polypeptide specifically binds to the ectodomain of one of PD-L1 with increased selectivity compared to the unmodified CD80. In some embodiments, the increased selectivity is for PD-L1.

In some embodiments, variant CD80 polypeptides have an increased or greater binding affinity to CTLA-4. In some embodiments, variant CD80 polypeptides with increased or greater binding affinity to CTLA-4 have an increase in binding affinity relative to the wild-type or unmodified CD80 polypeptide control of at least about 5%, such as at least about 10%, 15%, 20%, 30%, 40%, 50%, 60%, 70%, 80%, 90% or more for CTLA-4. In some embodiments, variant CD80 polypeptide with increased or greater binding affinity to CTLA-4 have an equilibrium dissociation constant (Kd) of less than 200 pM, 300 pM, 400 pM, 500 pM, or 600 pM for CTLA-4. In some embodiments, the variant polypeptide specifically binds to the ectodomain of one of CTLA-4 with increased selectivity compared to the unmodified CD80. In some embodiments, the increased selectivity is for CTLA-4.

In some embodiments, the increased selectivity comprises a greater ratio of binding of the variant CD80 polypeptide for one cognate binding partner selected from among PD-L1, CD28 and CTLA4 versus another of the cognate binding partner compared to the ratio of binding of the unmodified CD80 polypeptide for the one cognate binding partner versus the another of the cognate binding partner. In some embodiments, the ratio is greater by at least or at least about 1.5-fold, 2-fold, 3-fold, 4-fold, 5-fold, 10-fold, 15

The modification, e.g. substitution can be in the IgC domain or the IgV domain. In some embodiments, the variant CD80 polypeptide has up to 1, 2, 3, 4, 5, 6, 7, 8, 9, 10, 11, 12, 13, 14, 15, 16, 17, 18, 19, or 20 amino acid substitutions in the IgC domain or specific binding fragment thereof. In some embodiments, the variant CD80 polypeptide has up to 1, 2, 3, 4, 5, 6, 7, 8, 9, 10, 11, 12, 13, 14, 15, 16, 17, 18, 19, or 20 amino acid substitutions in the IgV domain or specific binding fragment thereof. In some embodiments, the variant CD80 polypeptide has at least about 80%, 81%, 82%, 83%, 84%, 85%, 86%, 86%, 88%, 89%, 90%, 91%, 92%, 93%, 94%, 95%, 96%, 97%, 98%, or 99% sequence identity with the wild-type or unmodified CD80 polypeptide or specific binding fragment thereof, such as with the amino acid sequence of SEQ ID NO: 1.

In some embodiments, the variant CD80 polypeptide has one or more amino acid modification, e.g. substitution in an unmodified CD80 or specific binding fragment there of corresponding to position(s) 130, 131, 139, 155, 156, 165 or 166 with reference to numbering of SEQ ID NO: 1. In some embodiments, such variant CD80 polypeptides exhibit altered binding affinity to one or more of CD28, PD-L1, and/or CTLA-4 compared to the wild-type or unmodified CD80 polypeptide. For example, in some embodiments, the variant CD80 polypeptide exhibits increased binding affinity to CD28, PD-L1, and/or CTLA-4 compared to a wild-type or unmodified CD80 polypeptide. In some embodiments, the variant CD80 polypeptide exhibits decreased binding affinity to CD28, PD-L1, or CTLA-4 compared to a wild-type or unmodified CD80 polypeptide.

In some embodiments, the variant CD80 polypeptide has one or more amino acid modification, e.g. substitution selected from T130A, S131A, S131V, S131I, S131F, S131R, S131E, S131D, S131Q, L139V, V155A, V155I, or V155T, A165S, A165V, A165I, A165F, A165R, A165E, A165D, or A165Q. V166A, V166L or V166T or a conservative amino acid modification, e.g. substitution thereof. A conservative amino acid modification, e.g. substitution is any amino acid that falls in the same class of amino acids as the substituted amino acids, other than the wild-type or unmodified amino acid. The classes of amino acids are aliphatic (glycine, alanine, valine, leucine, and isoleucine), hydroxyl or sulfur-containing (serine, cysteine, threonine, and methionine), cyclic (proline), aromatic (phenylalanine, tyrosine, tryptophan), basic (histidine, lysine, and arginine), and acidic/amide (aspartate, glutamate, asparagine, and glutamine).

In some embodiments, the variant CD80 polypeptide has one or more amino acid modification, e.g. substitution selected from T130A, S131A, S131V, S131I, S131F, S131R, S131E, S131D, S131Q, L139V, V155A, V155I, or V155T, A165S, A165V, A165I, A165F, A165R, A165E, A165D, or A165Q. V166A, V166L or V166T.

In some embodiments, the one or more amino acid modification, e.g. substitution is T130A, S131A, S131V, S131I, S131F, S131R, S131E, S131D, S131Q, L139V, V155A, V155I, or V155T, A165S, A165V, A165I, A165F, A165R, A165E, A165D, or A165Q. V166A, V166L, V166T, In some embodiments, the variant CD80 polypeptide comprises any of the mutations listed in Table 1. As indicated, the exact locus or residues corresponding to a given domain can vary, such as depending on the methods used to identify or classify the domain. Also, in some cases, adjacent N- and/or C-terminal amino acids of a given domain (e.g. IgV) also can be included in a sequence of a variant IgSF polypeptide, such as to ensure proper folding of the domain when expressed.

In some embodiments, the variant CD80 polypeptide comprises any of the mutations listed in Table 1, relative to the human CD80 protein, or at the corresponding position in the non-human protein version. In some embodiments, the variant CD80 polypeptide comprises mutations of the extracellular domain (ECD) or IgV sequences as provided for in Table 1.

TABLE 1

Exemplary variant CD80 polypeptides

| Position | Single Mutation | Double Mutations | Triple Mutations |
|---|---|---|---|
| T130 | T130A | T130A/S156A | |
| S131 | S131A, S131V, S131I, S131F, S131R, S131E, S131D, S131Q | S131A/S156I, S131A/A165S | S131A/S156I/A165S |
| L139 | | L139V/V166L | L139V/S156A/V166L |
| V155 | V155A, V155I, V155T | V155A/S156A, V155I/S156A, V155T/S156A | |
| S156 | S156V, S156L, S156I, S156F, S156R, S156E, S156D, S156Q | S156A/V155A, S156A/V155I, S156A/V155T, S156A/T130A, S156A/V166A, S156I/A165S, S156I/S131A | S156A/V166L/L139V, S156I/A165S/S131A |
| A165 | A165S, A165V, A165I, A165F, A165R, A165E, A165D, A165Q | A165S/S156I, A165S/S131A | A165S/S131A/S156I |
| V166 | V166A, V166T | V166L/L139V, V166A/S156A | V166L/L139V/S156A |

To provide a surrogate model for in vivo studies, the following mouse CD80 variant polypeptides can be made and tested based on wild type mouse CD80 sequence, T165E, T165Q, T165R, T165A, T165S, T165V, T165I, T165F, T165D, S131V, S131I, S131F, S131R, S131E, S131Q, S131A, and S131P. The wild type mouse sequence is provided in FIG. 14B, and is provided as SEQ ID NO: 15.

III. Pharmaceutical Compositions

The present disclosure provides a pharmaceutical composition comprises the variant CD80 polypeptide of the present disclosure. In some embodiments, the pharmaceutical composition further comprises a pharmaceutically acceptable excipient. In some embodiments, the pharmaceutical composition is sterile. In some embodiments, a kit comprises the pharmaceutical composition of the present disclosure, and instructions for use.

In other embodiments, an article of manufacture comprises the pharmaceutical composition of the present disclosure in a vial. In some embodiments, the vial is sealed. In some embodiments, a kit comprises the article of manufacture of the present disclosure, and instructions for use.

The pharmaceutical composition of the present disclosure can comprise, in addition to a multimeric polypeptide of the present disclosure, one or more of: a salt, e.g., NaCl, MgC12, KC1, MgSO4, etc.; a buffering agent, e.g., a Tris buffer, N-(2-Hydroxyethyl)piperazine-N'-(2-ethanesulfonic acid) (HEPES), 2-(N-Morpholino) ethanesulfonic acid (MES), 2-(N-Morpholino) ethanesulfonic acid sodium salt (MES), 3-(N-Morpholino) propanesulfonic acid (MOPS), N-tris [Hydroxymethyl]methyl-3-aminopropanesulfonic acid (TAPS), etc.; a solubilizing agent; a detergent, e.g., a non-ionic detergent such as Tween-20, etc.; a protease inhibitor; glycerol; and the like.

The pharmaceutical composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

A pharmaceutical composition can comprise a multimeric polypeptide of the present disclosure, and a pharmaceutically acceptable excipient. In some cases, a subject pharmaceutical composition is suitable for administration to a subject, e.g., is sterile. For example, in some embodiments, a subject pharmaceutical composition is suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a polypeptide or a multimeric or dimeric protein of the present disclosure is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a polypeptide or a multimeric or dimeric protein of the present disclosure in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

IV. Methods of Use

In some embodiments, provided herein is a method of modulating an immune response in a subject, comprising administering the pharmaceutical composition of the present disclosure to the subject. In some embodiments, modulating the immune response treats a disease or condition in the subject. In some embodiments, the immune response is increased. In some embodiments, the immune response is decreased.

In some embodiments, the disease or condition is a tumor or cancer. In some embodiments, the disease or condition is selected from melanoma, lung cancer, bladder cancer, a hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer. In some embodiments, the disease or condition is an inflammatory or autoimmune disease or condition. In some embodiments, the disease or condition is an antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease. In some embodiments, the disease or condition is selected from inflammatory bowel disease, transplant, Crohn's disease, ulcerative colitis, multiple sclerosis, asthma, rheumatoid arthritis, or psoriasis.

In some embodiments, provided herein is a method of treating a disease or condition in a subject, comprising administering the pharmaceutical composition of the present disclosure to the subject.

In some embodiments, the disease or condition is a tumor or cancer. In some embodiments, provided herein is a the disease or condition is selected from melanoma, lung cancer, bladder cancer, a hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, a musculoskeletal cancer, a head and neck cancer, a gastrointestinal cancer, a germ cell cancer, or an endocrine and neuroendocrine cancer.

In some embodiments, the disease or condition is an infection. In some embodiments, the disease or condition is an inflammatory or autoimmune disease or condition. In some embodiments, provided herein is a the disease or condition is an antineutrophil cytoplasmic antibodies (ANCA)-associated vasculitis, a vasculitis, an autoimmune skin disease, transplantation, a Rheumatic disease, an inflammatory gastrointestinal disease, an inflammatory eye disease, an inflammatory neurological disease, an inflammatory pulmonary disease, an inflammatory endocrine disease, or an autoimmune hematological disease. In some embodiments, provided herein is a the disease or condition is selected from inflammatory bowel disease, transplant, Crohn's disease, ulcerative colitis, multiple sclerosis, asthma, rheumatoid arthritis, or psoriasis.

In some embodiments, the patient is administered with a second therapeutic agent.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed.

Example 1

Construction of Expression Vectors for Production of Mutant CD80-Fc Fusion Proteins and Expression/Purification of Mutant CD80-Fc Fusion Proteins (CD80 Variants)

Wild-type human CD80-human IgG1 Fc expression cassette (hCD80-Fc, FIG. 13A was generated by de novo gene synthesis and was cloned into pcDNA3.4 vector (Thermo Fisher Scientific). Mutations to the CD80 IgC domain at positions S131, V155, A165 and V166 were introduced by either site-directed mutagenesis employing QuikChange Lightening Site-Directed Mutagenesis Kit (Agilent) or by direct DNA synthesis (GenScript) according to the Provider's manual/protocol. The primers for site-directed mutagenesis were listed in Tables 2 and 3, and used for single site-directed mutagenesis. QuikChange Lightening Multi Site-Directed Mutagenesis Kit was used for multiple site-directed mutagenesis.

Figure 15B:
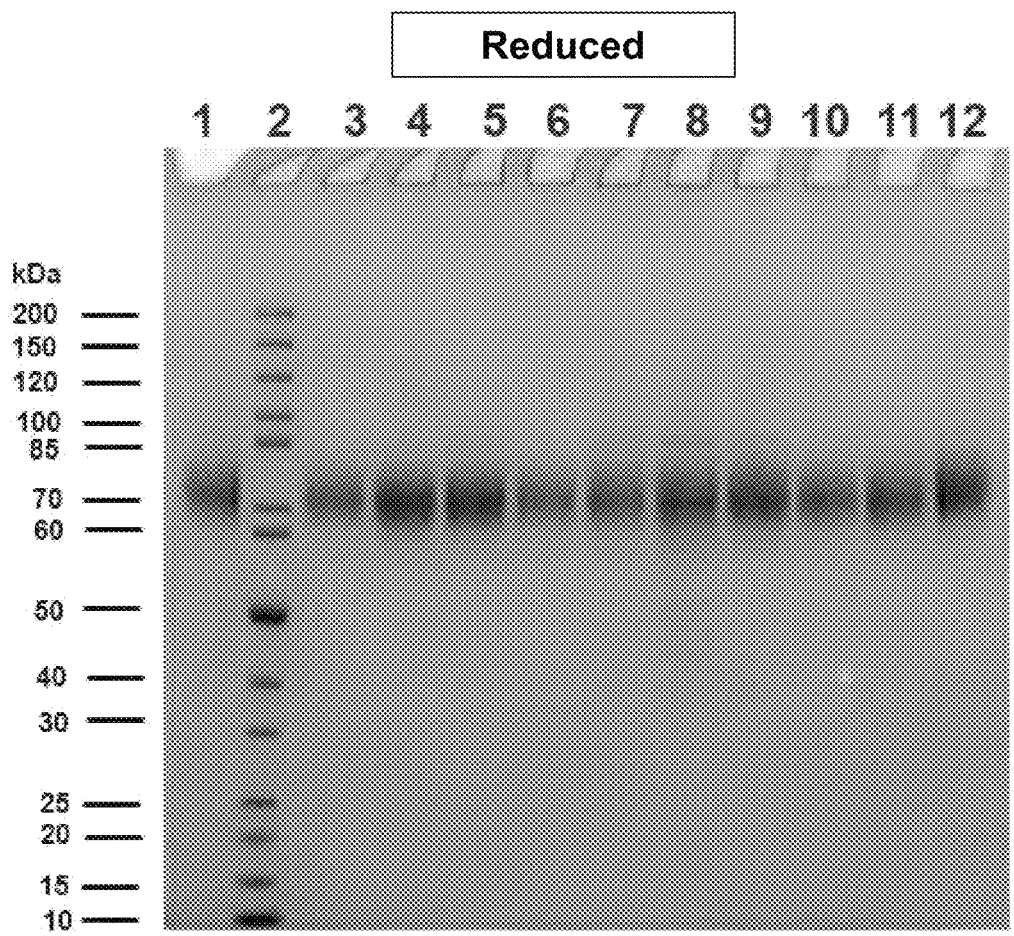
FIG. 15B depicts SDS-PAGE analysis results of selected and purified CD80-Fc fusion polypeptides in a reducing condition. Samples loaded with purified CD80-Fc Fusion Protein in FIGS. 15A-15B are as follows; Lane 1: Molecular Weight Marker; Lane 2: S131F, 1.5 ug/lane; Lane 3: S131R, 1.5 ug/lane; Lane 4: S131E, 2.0 ug/lane; Lane 5: S131D, 1.6 ug/lane; Lane 6: S131Q, 1.6 ug/lane; Lane 7: A165V, 1.2 ug/lane; Lane 8: A165I, 1.6 ug/lane; Lane 9: A165F, 1.6 ug/lane; Lane 10: A165R, 1.6 ug/lane; Lane 11: A165D, 1.6 ug/lane; Lane 12: A165Q, 1.6 ug/lane.
Figure 15C:
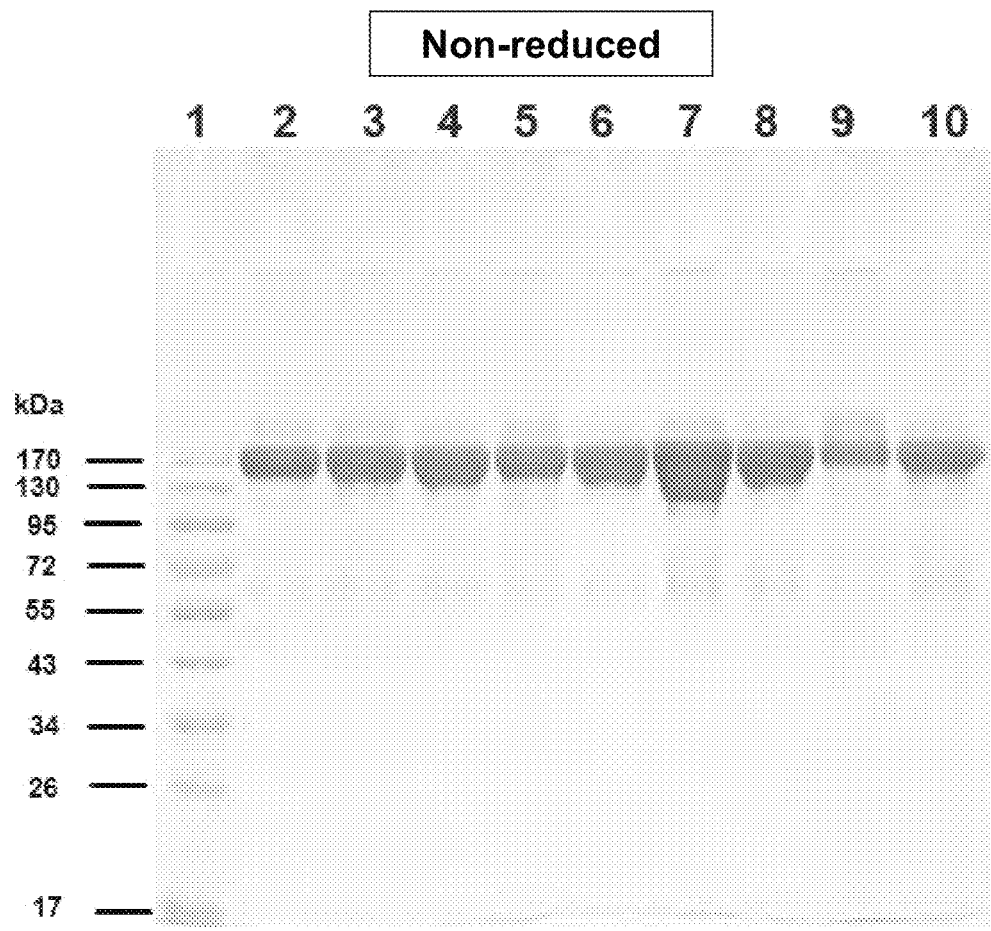
FIG. 15C depicts SDS-PAGE analysis results of selected and purified CD80-Fc Fusion Proteins in a non-reducing condition.
Figure 15D:
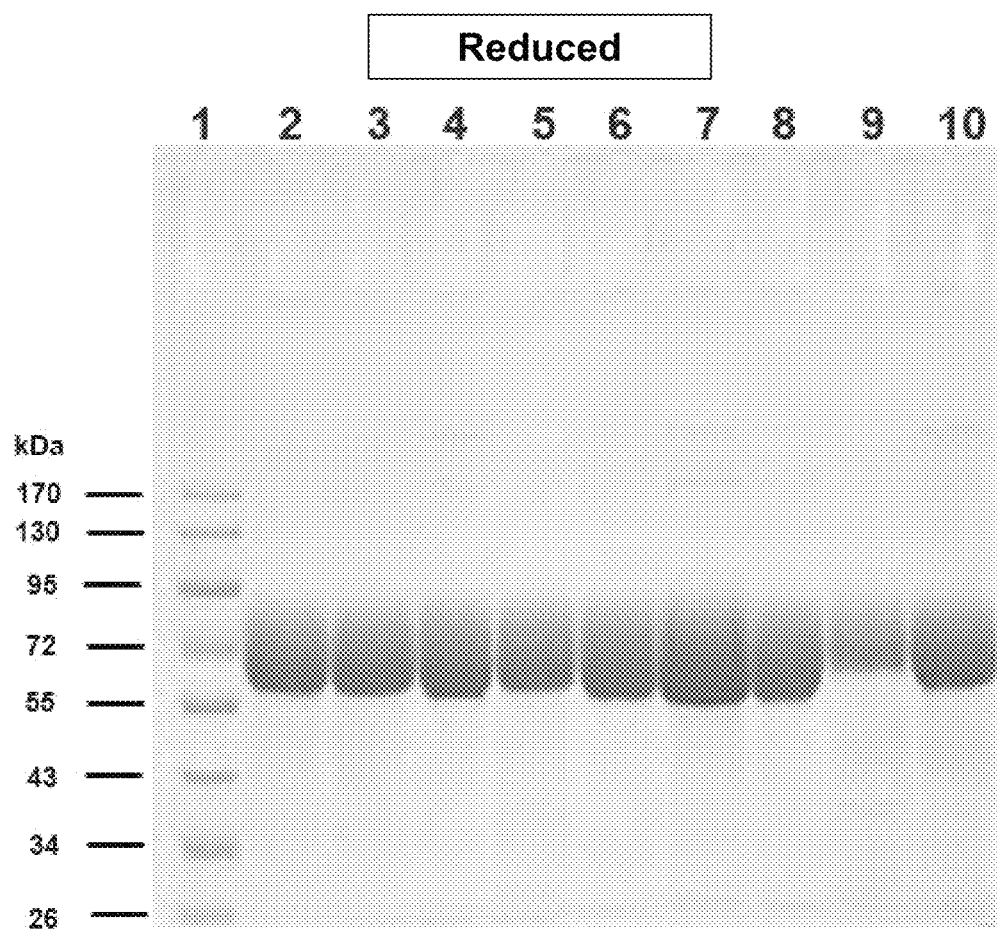
FIG. 15D depicts SDS-PAGE analysis results of selected and purified CD80-Fc fusion polypeptides in a reducing condition. Samples loaded with purified CD80-Fc fusion protein in FIGS. 15C-15D are as follows; Lane 1: Molecular Weight Marker; Lane 2: V166A, 10 ug/lane; Lane 3: V166T, 10 ug/lane; Lane 4: V166L/L139V, 10 ug/lane; Lane 5: S156A/V155A, 10 ug/lane; Lane 6: S156A/V155I, 10 ug/lane; Lane 7: S156A/V155T, 10 ug/lane; Lane 8: S156A/T130A, 10 ug/lane; Lane 9: S156A/V166A, 10 ug/lane; Lane 10: S156A/V166L/L139V, 10 ug/lane.
Figure 16A:
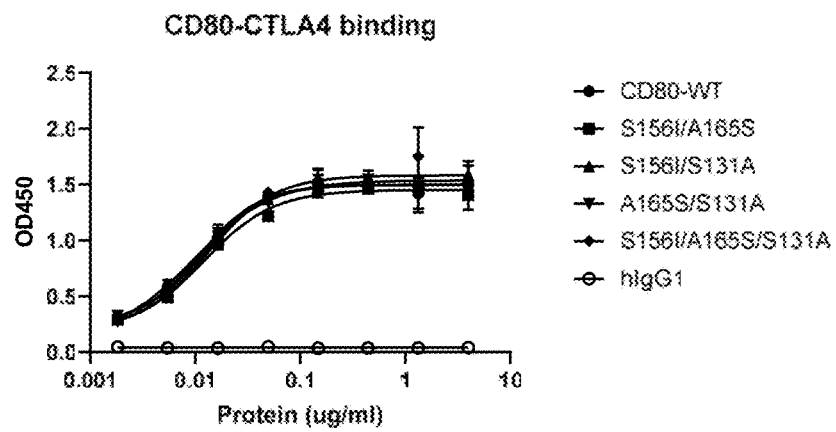
FIG. 16A depicts results of binding assays by ELISA to test binding affinity of variant CD80-Fc Fusion Proteins to immobilized binding partner CTLA-4. Types of variant CD80 polypeptides tested herein are as follows: amino acid substitutions/mutations at two positions (S156I/A165S, S156I/S131A, and A165S/S131A—double substitutions/mutations), and three positions (S156I/A165S/S131A—triple substitutions/mutations). CD80-WT protein is used as a positive control and human IgG1 protein is a negative control.
Figure 16B:
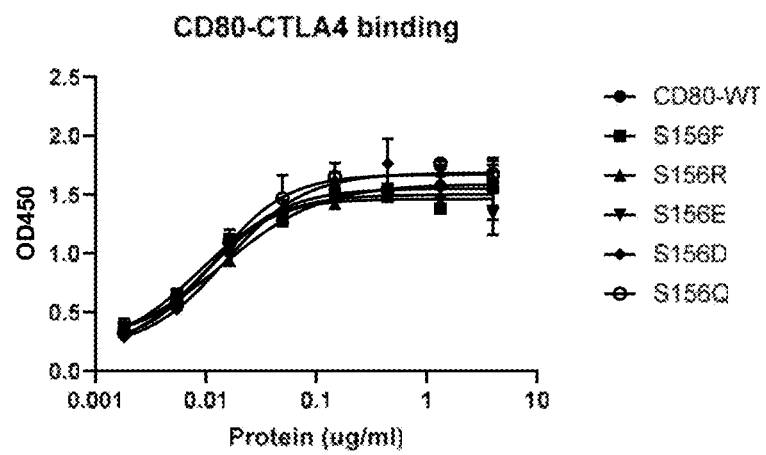
FIG. 16B depicts results of binding assays by ELISA to test binding affinity of variant CD80-Fc Fusion Proteins to immobilized binding partner CTLA-4. Types of variant CD80 polypeptides tested herein are as follows: a single amino acid substitution/mutation at position S156 (S156F, S156R, S156E, S156D, and S156Q). CD80-WT protein is used as a positive control.
Figure 16C:
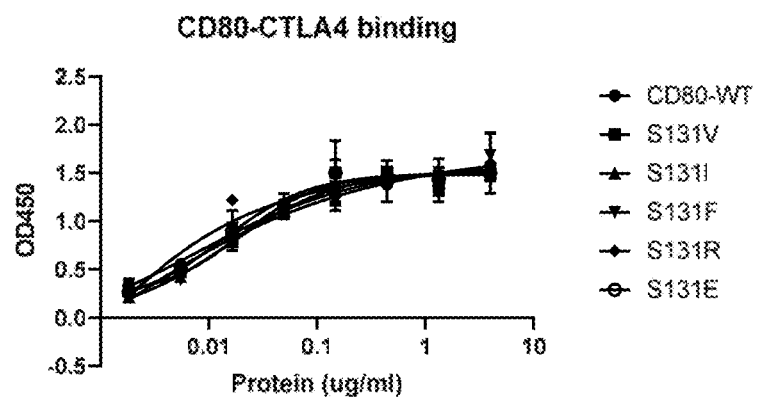
FIG. 16C depicts results of binding assays by ELISA to test binding affinity of variant CD80-Fc Fusion Proteins to immobilized binding partner CTLA-4. Types of variant CD80 polypeptides tested herein are as follows: a single amino acid substitution/mutation at position S131 (S131V, S131I, S131F, S131R, and S131E). CD80-WT protein is used as a positive control.
Figure 16D:
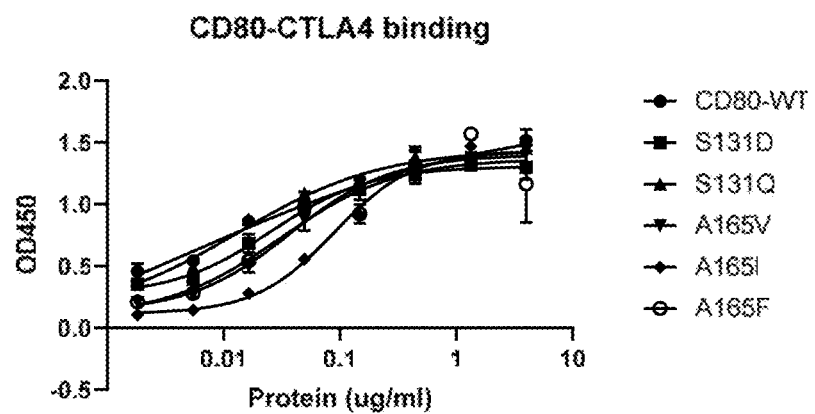
FIG. 16D depicts results of binding assays by ELISA to test binding affinity of variant CD80-Fc Fusion Proteins to immobilized binding partner CTLA-4. Types of variant CD80 polypeptides tested herein are as follows: a single amino acid substitution/mutation at position S131 or A165 (S131D, S131Q, A165V, A165I, and A165F). CD80-WT protein is used as a positive control.
Figure 16E:
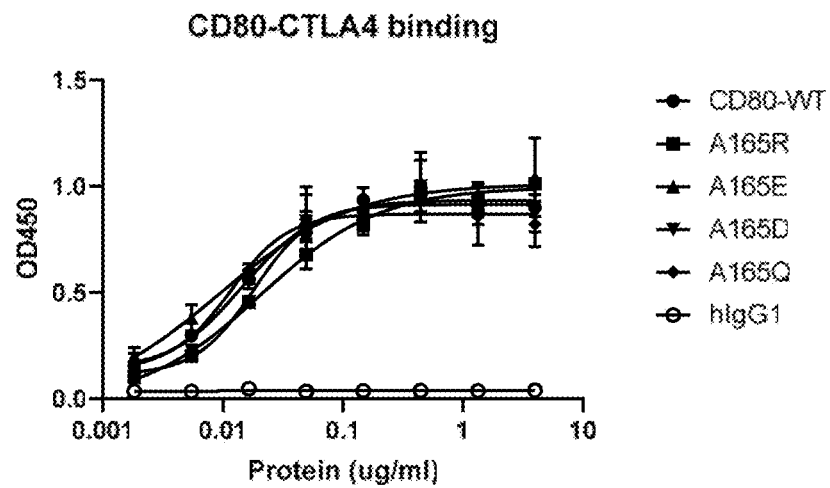
FIG. 16E depicts results of binding assays by ELISA to test binding affinity of variant CD80-Fc Fusion Proteins to immobilized binding partner CTLA-4. Types of variant CD80 polypeptides tested herein are as follows: a single amino acid substitution/mutation at position A165 (A165R, A165E, A165D, and A165Q). CD80-WT protein is used as a positive control and human IgG1 protein is a negative control.
Figure 16F:
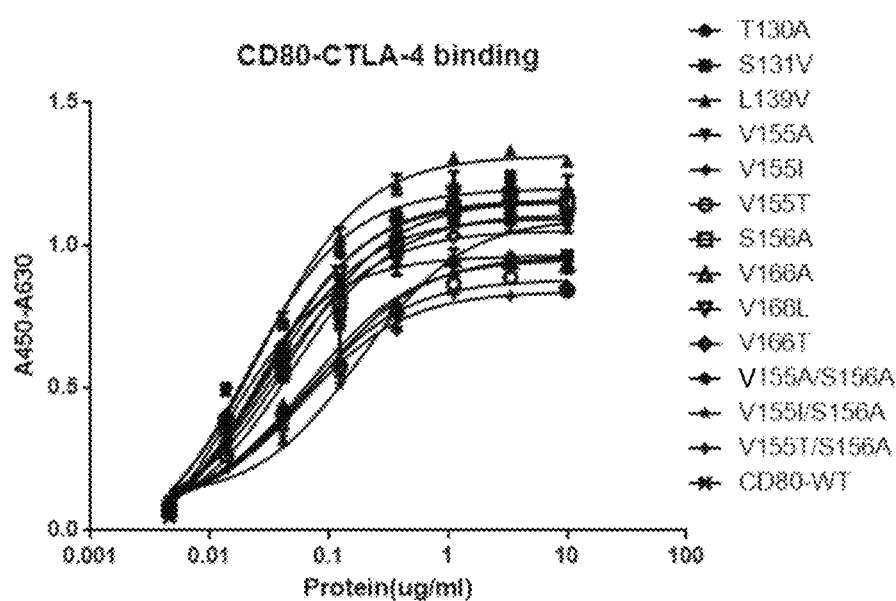
FIG. 16F depicts results of binding assays by ELISA to test binding affinity of variant CD80-Fc Fusion Proteins to immobilized binding partner CTLA-4. Types of variant CD80 polypeptides tested herein are as follows: a single amino acid substitution/mutation (T130A, S131V, L139V, V155A, V155I, V155T, S156A, V166A, V166L, V166T, V155A/S156A, V155I/S156A, and V155T/S156A). CD80-WT protein is used as a positive control.
Figure 17A:
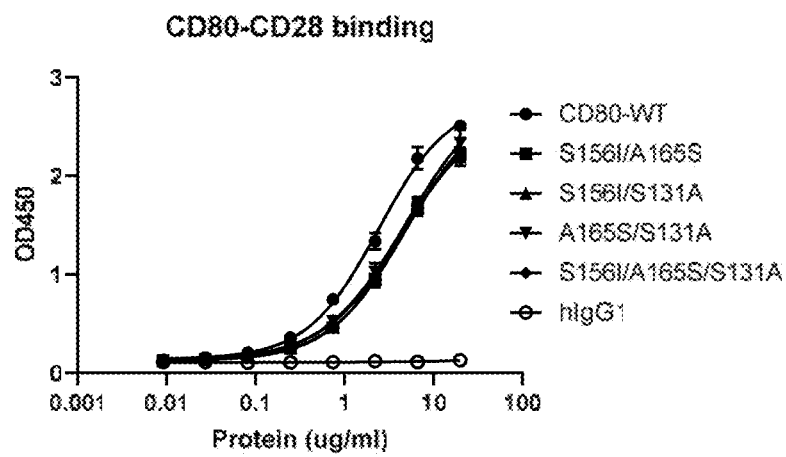
FIG. 17A depicts results of binding assays by ELISA to test binding affinity of variant CD80-Fc Fusion Proteins to immobilized binding partner CD28. Types of variant CD80 polypeptides tested herein are as follows: amino acid substitutions/mutations at two positions (S156I/A165S, S156I/S131A, and A165S/S131A—double substitutions/mutations), and three positions (S156I/A165S/S131A—triple substitutions/mutations). CD80-WT protein is used as a positive control and human IgG1 protein is a negative control.
Figure 17B:
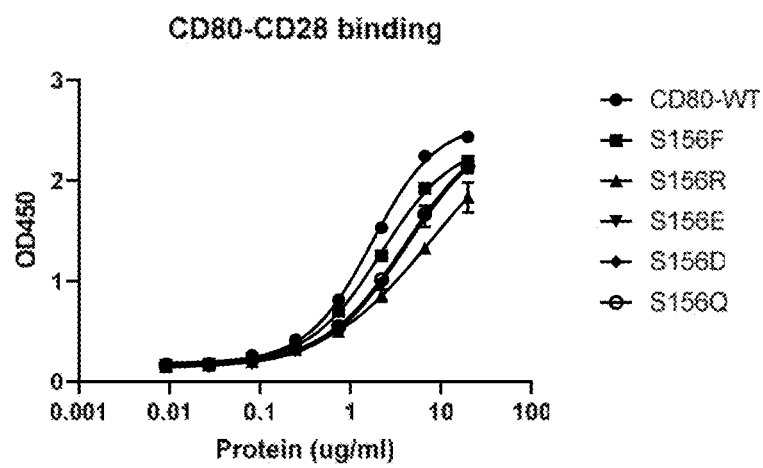
FIG. 17B depicts results of binding assays by ELISA to test binding affinity of variant CD80-Fc Fusion Proteins to immobilized binding partner CD28. Types of variant CD80 polypeptides tested herein are as follows: a single amino acid substitution/mutation at position S156 (S156F, S156R, S156E, S156D, and S156Q). CD80-WT protein is used as a positive control.
Figure 17C:
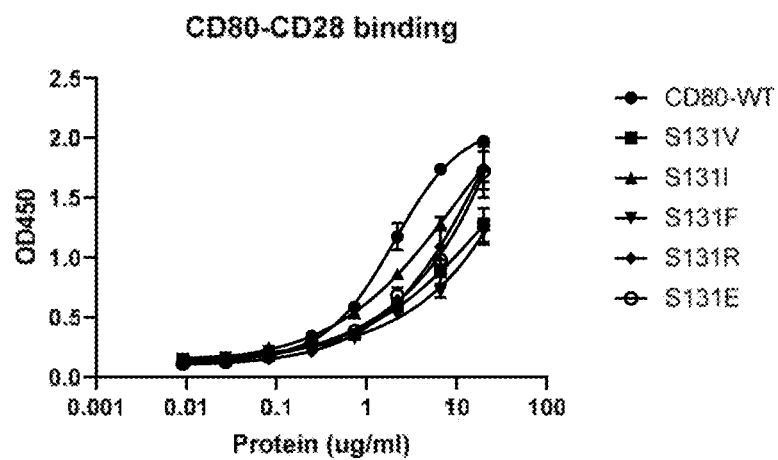
FIG. 17C depicts results of binding assays by ELISA to test binding affinity of variant CD80-Fc Fusion Proteins to immobilized binding partner CD28. Types of variant CD80 polypeptides tested herein are as follows: a single amino acid substitution/mutation at position S131 (S131V, S131I, S131F, S131R, and S131E). CD80-WT protein is used as a positive control.
Figure 17D:
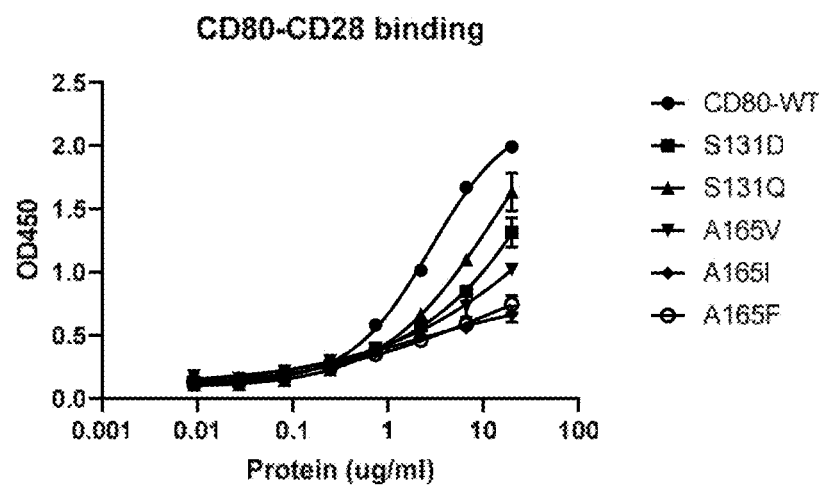
FIG. 17D depicts results of binding assays by ELISA to test binding affinity of variant CD80-Fc Fusion Proteins to immobilized binding partner CD28. Types of variant CD80 polypeptides tested herein are as follows: a single amino acid substitution/mutation at position S131 or A165 (S131D, S131Q, A165V, A165I, and A165F). CD80-WT protein is used as a positive control and human IgG1 protein is a negative control.
Figure 17E:
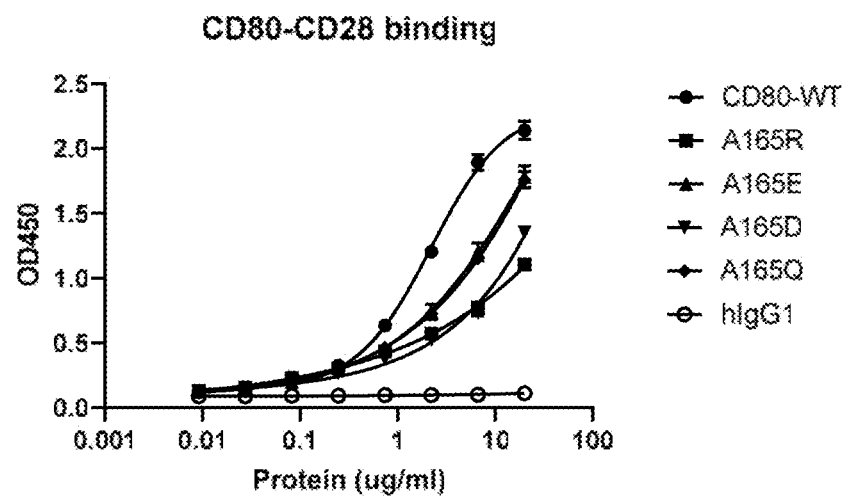
FIG. 17E depicts results of binding assays by ELISA to test binding affinity of variant CD80-Fc Fusion Proteins to immobilized binding partner CD28. Types of variant CD80 polypeptides tested herein are as follows: a single amino acid substitution/mutation at position A165 (A165R, A165E, A165D, and A165Q). CD80-WT protein is used as a positive control.
Figure 18A:
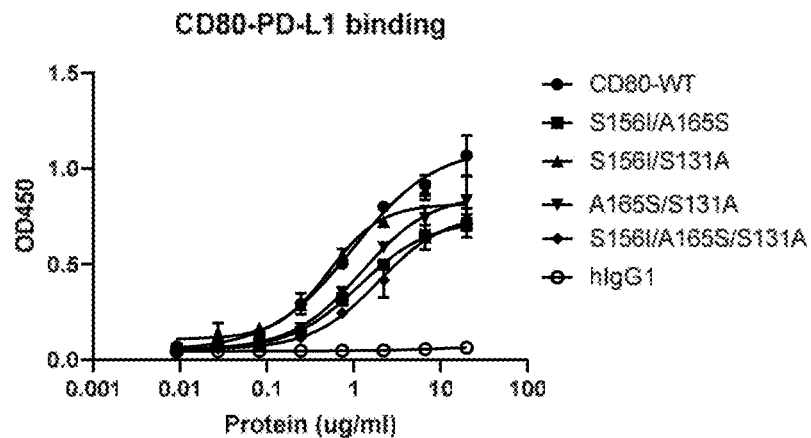
FIG. 18A depicts results of binding assays by ELISA to test binding affinity of variant CD80-Fc Fusion Proteins to immobilized binding partner PD-L1. Types of variant CD80 polypeptides tested herein are as follows: amino acid substitutions/mutations at two positions (S156I/A165S, S156I/S131A, and A165S/S131A—double substitutions/mutations), and three positions (S156I/A165S/S131A—triple substitutions/mutations). CD80-WT protein is used as a positive control and human IgG1 protein is a negative control.
Figure 18B:
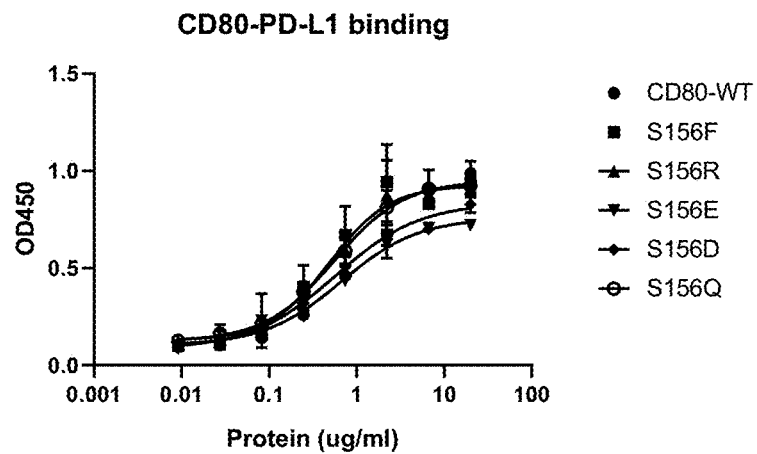
FIG. 18B depicts results of binding assays by ELISA to test binding affinity of variant CD80-Fc Fusion Proteins to immobilized binding partner PD-L1. Types of variant CD80 polypeptides tested herein are as follows: a single amino acid substitution/mutation at position S156 (S156F, S156R, S156E, S156D, and S156Q). CD80-WT protein is used as a positive control.
Figure 18C:
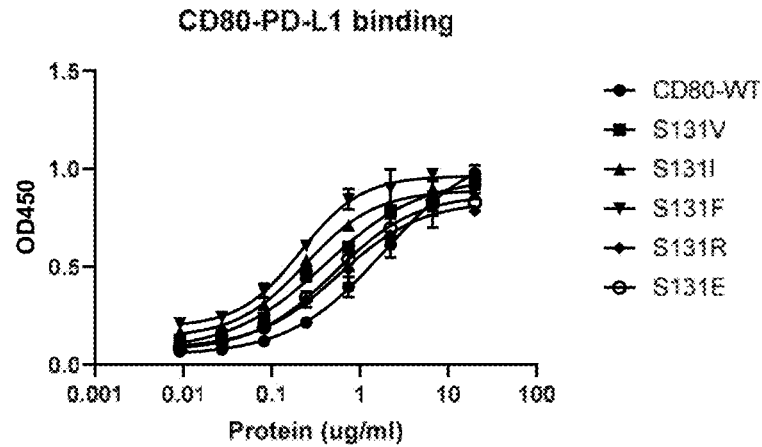
FIG. 18C depicts results of binding assays by ELISA to test binding affinity of variant CD80-Fc Fusion Proteins to immobilized binding partner PD-L1. Types of variant CD80 polypeptides tested herein are as follows: a single amino acid substitution/mutation at position S131 (S131V, S131I, S131F, S131R, and S131E). CD80-WT protein is used as a positive control.
Figure 18D:
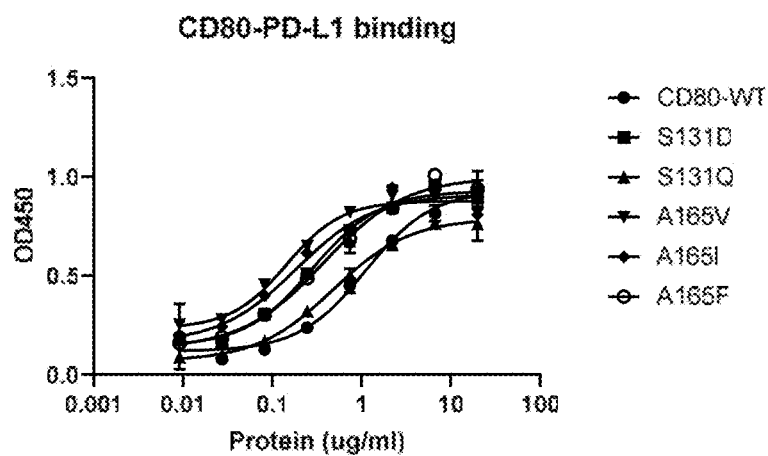
FIG. 18D depicts results of binding assays by ELISA to test binding affinity of variant CD80-Fc Fusion Proteins to immobilized binding partner PD-L1. Types of variant CD80 polypeptides tested herein are as follows: a single amino acid substitution/mutation at position S131 or A165 (S131D, S131Q, A165V, A165I, and A165F). CD80-WT protein is used as a positive control.
Figure 18E:
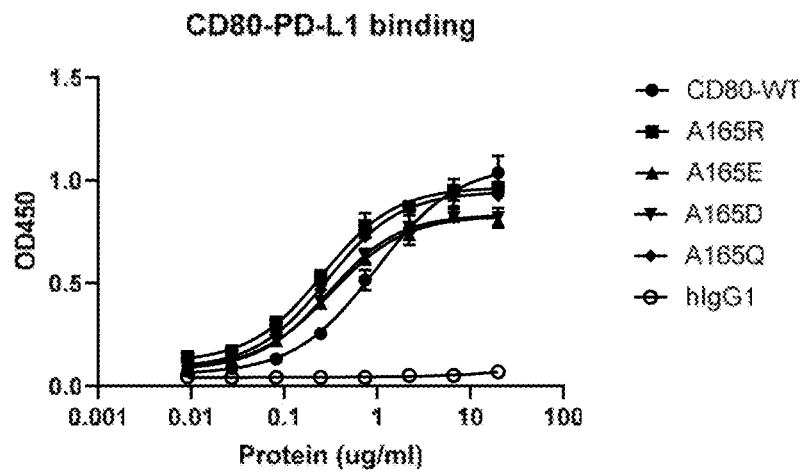
FIG. 18E depicts results of binding assays by ELISA to test binding affinity of variant CD80-Fc Fusion Proteins to immobilized binding partner PD-L1. Types of variant CD80 polypeptides tested herein are as follows: a single amino acid substitution/mutation at position A165 (A165R, A165E, A165D, and A165Q). CD80-WT protein is used as a positive control and human IgG1 protein is a negative control.
Figure 24:
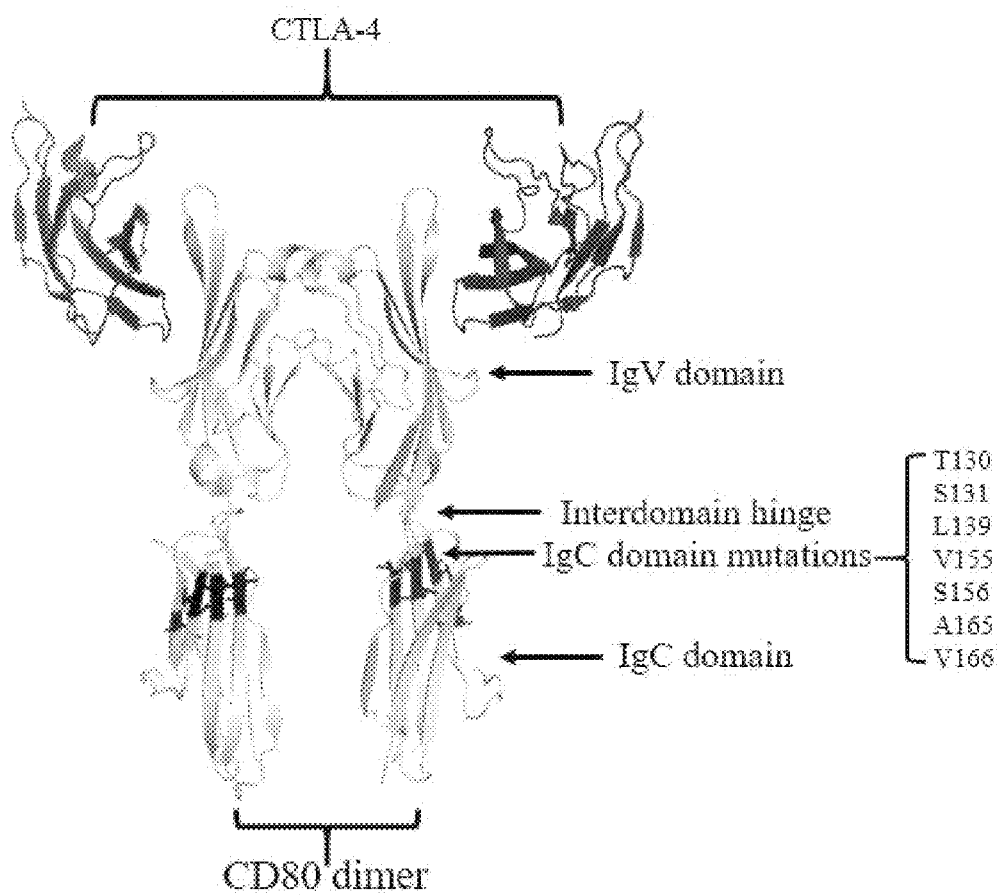
FIG. 24 illustrates crystal structure of CD80 dimer (composed of IgC domain, interdomain hinge, and IgV domain) complexed with CTLA-4. Mutation positions in IgC domain are presented as follows: T130, S131, L139, V155, S156, A165, and V166.
Figure 25A:
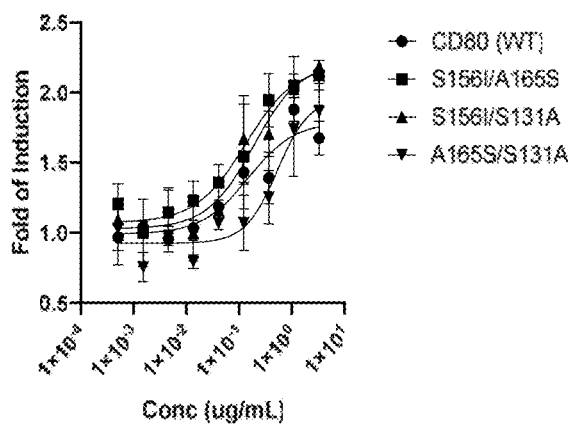
FIG. 25A depicts results of CTLA-4 blockade assay to evaluate the ability of variant CD80-Fc Fusion Proteins blocking CTLA-4/CD28 interaction function. Types of variant CD80 polypeptides tested herein are as follows: amino acid substitutions/mutations at two positions (S156I/A165S, S156I/S131A, and A165 S/S131A—double substitutions/mutations), CD80-WT protein is used as a positive control.
Figure 25B:
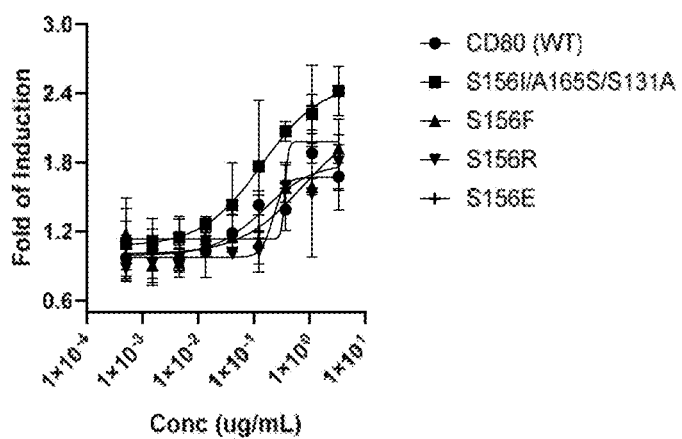
FIG. 25B depicts results of CTLA-4 blockade assay to evaluate the ability of variant CD80-Fc Fusion Proteins blocking CTLA-4/CD28 interaction function. Types of variant CD80 polypeptides tested herein are as follows: amino acid substitutions/mutations at three positions (S156I/A165S/S131A—triple substitutions/mutations) and one position at S156 (S156F, S156R, and S156E). CD80-WT protein is used as a positive control.
Figure 25C:
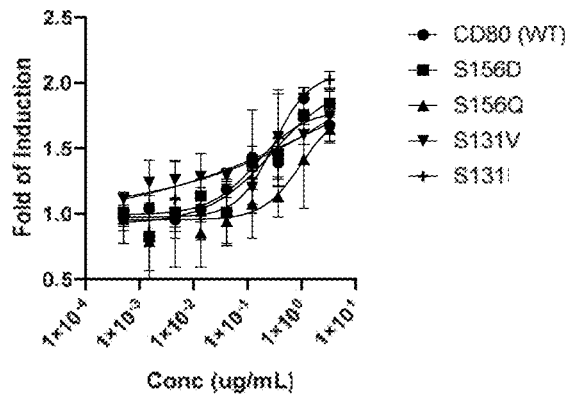
FIG. 25C depicts results of CTLA-4 blockade assay to evaluate the ability of variant CD80-Fc Fusion Proteins blocking CTLA-4/CD28 interaction function. Types of variant CD80 polypeptides tested herein are as follows: a single amino acid substitution/mutation at position S156 or S131 (S156D, S156Q, S131V, and S131O. CD80-WT protein is used as a positive control.
Figure 25D:
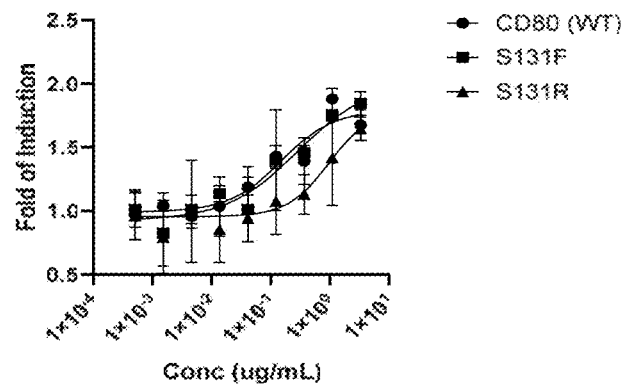
FIG. 25D depicts results of CTLA-4 blockade assay to evaluate the ability of variant CD80-Fc Fusion Proteins blocking CTLA-4/CD28 interaction function. Types of variant CD80 polypeptides tested herein are as follows: a single amino acid substitution/mutation at position S131 (S131F, and S131R). CD80-WT protein is used as a positive control.
Figure 25E:
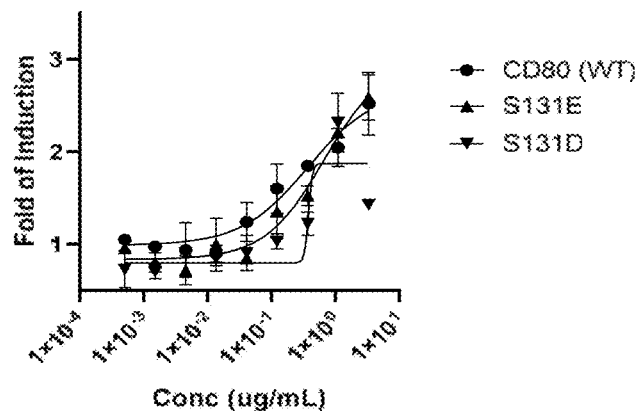
FIG. 25E depicts results of CTLA-4 blockade assay to evaluate the ability of variant CD80-Fc Fusion Proteins blocking CTLA-4/CD28 interaction function. Types of variant CD80 polypeptides tested herein are as follows: a single amino acid substitution/mutation at position S131 (S131E, and S131D). CD80-WT protein is used as a positive control.
Figure 25F:
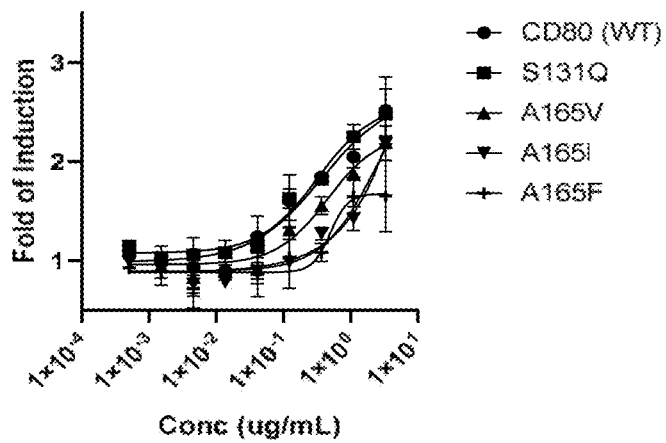
FIG. 25F depicts results of CTLA-4 blockade assay to evaluate the ability of variant CD80-Fc Fusion Proteins blocking CTLA-4/CD28 interaction function. Types of variant CD80 polypeptides tested herein are as follows: a single amino acid substitution/mutation at position S131 or A165 (S131Q, A165V, A165I, and A165F). CD80-WT protein is used as a positive control.
Figure 25G:
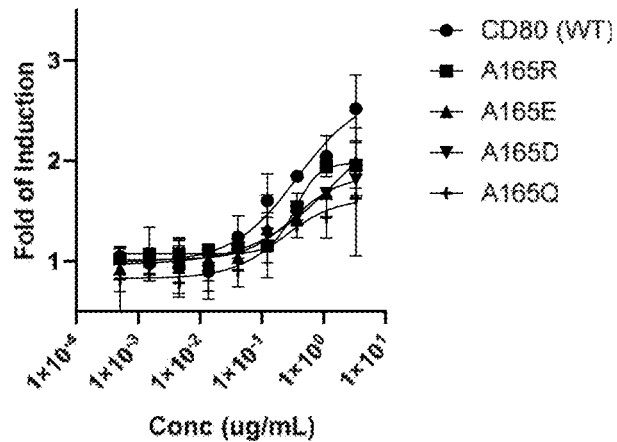
FIG. 25G depicts results of CTLA-4 blockade assay to evaluate the ability of variant CD80-Fc Fusion Proteins blocking CTLA-4/CD28 interaction function. Types of variant CD80 polypeptides tested herein are as follows: a single amino acid substitution/mutation at position A165 (A165R, A165E, A165D, and A165Q). CD80-WT protein is used as a positive control.
Figure 25H:
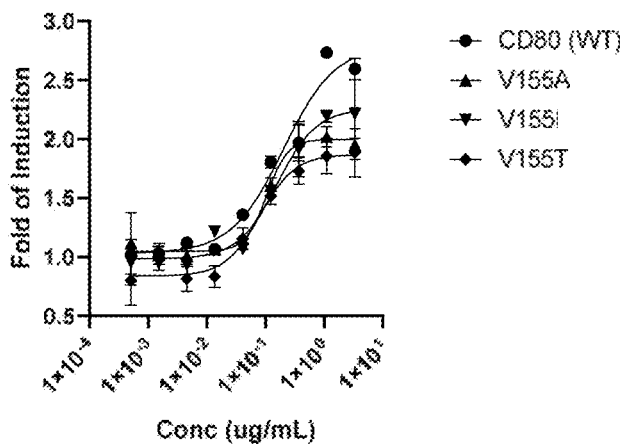
FIG. 25H depicts results of CTLA-4 blockade assay to evaluate the ability of variant CD80-Fc Fusion Proteins blocking CTLA-4/CD28 interaction function. Types of variant CD80 polypeptides tested herein are as follows: a single amino acid substitution/mutation at position V155 (V155A, V155I, and V155T). CD80-WT protein is used as a positive control.
Figure 25I:
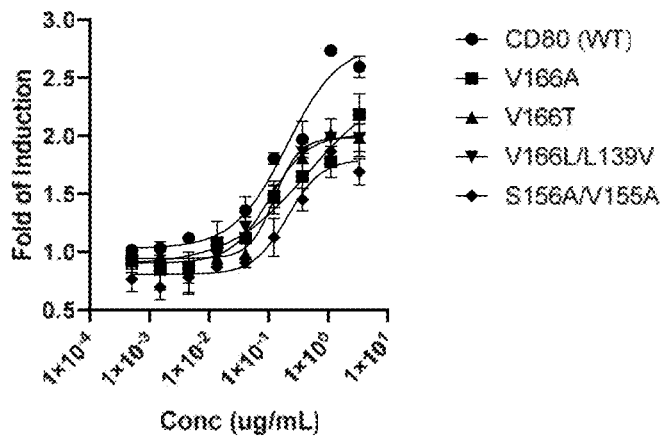
FIG. 25I depicts results of CTLA-4 blockade assay to evaluate the ability of variant CD80-Fc Fusion Proteins blocking CTLA-4/CD28 interaction function. Types of variant CD80 polypeptides t S131 (S131I, S131F, S131R, S131E, and S131Q). Mouse CD80-WT protein is used as a positive control.
Figure 25J:
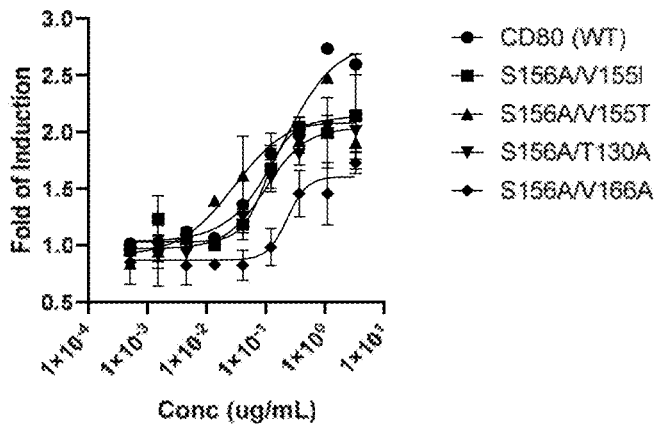
Figure 25K:
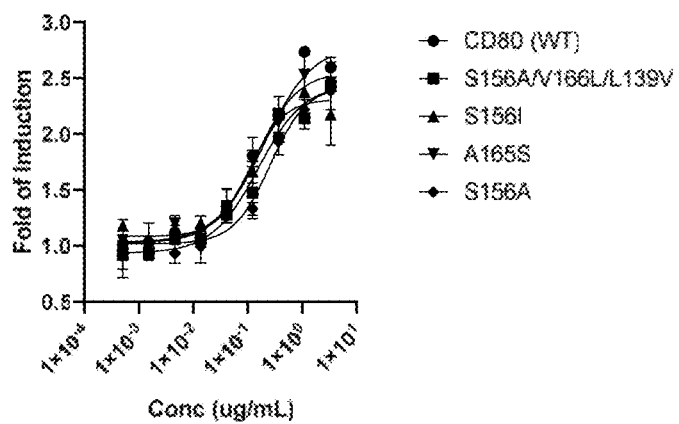
Figure 25L:
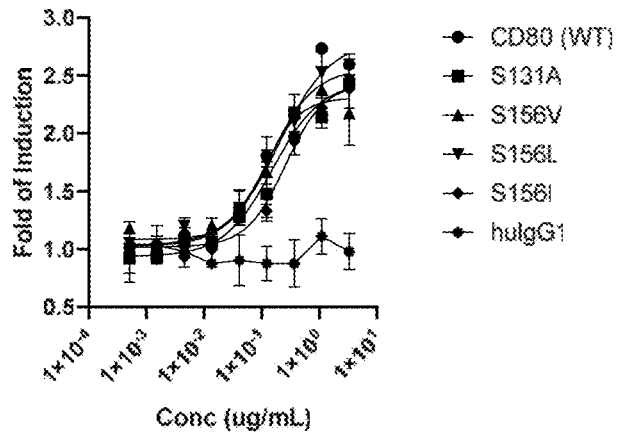
Figure 26A:
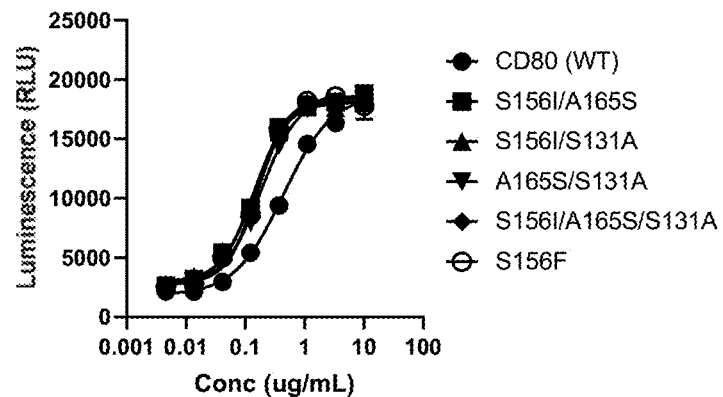
Figure 26B:
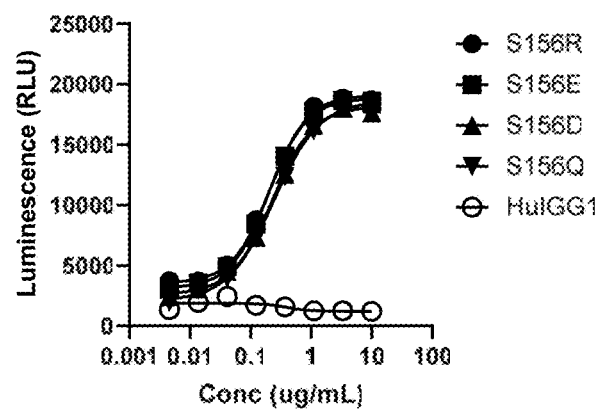
Figure 26C:
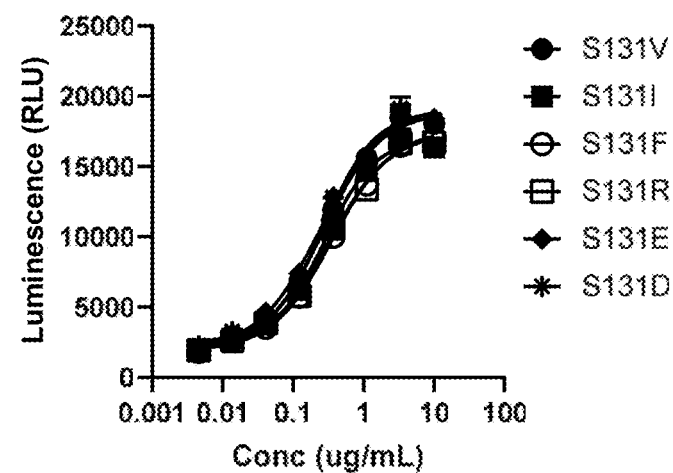
Figure 26D:
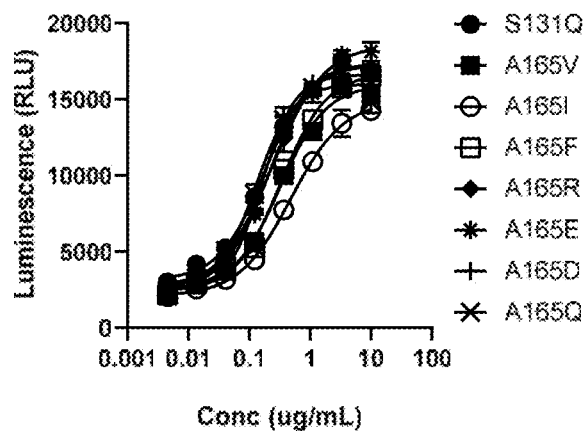
Figure 26E:
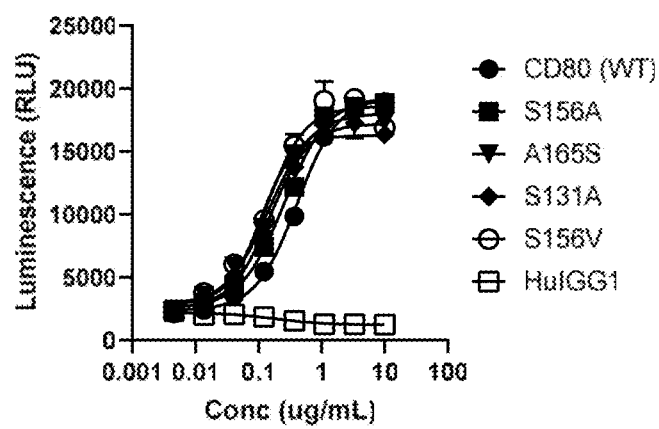
Figure 26F:
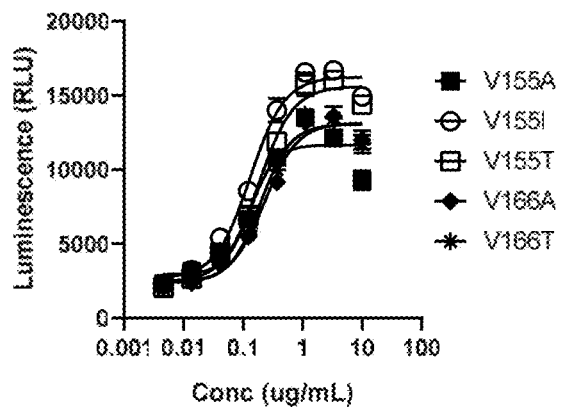
Figure 26G:
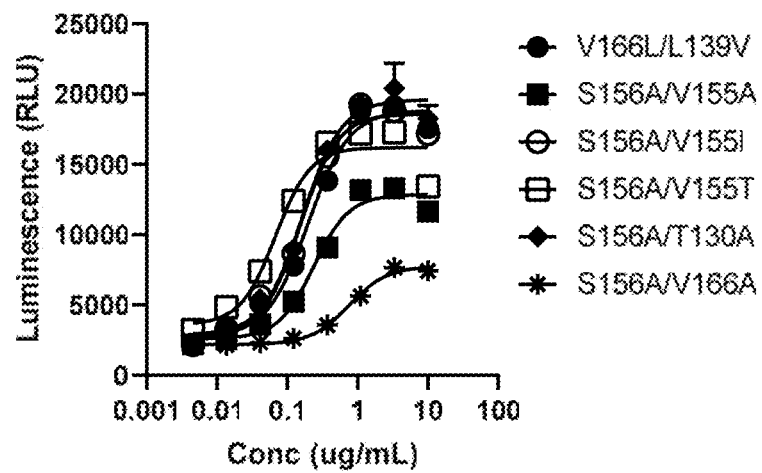
Figure 26H:
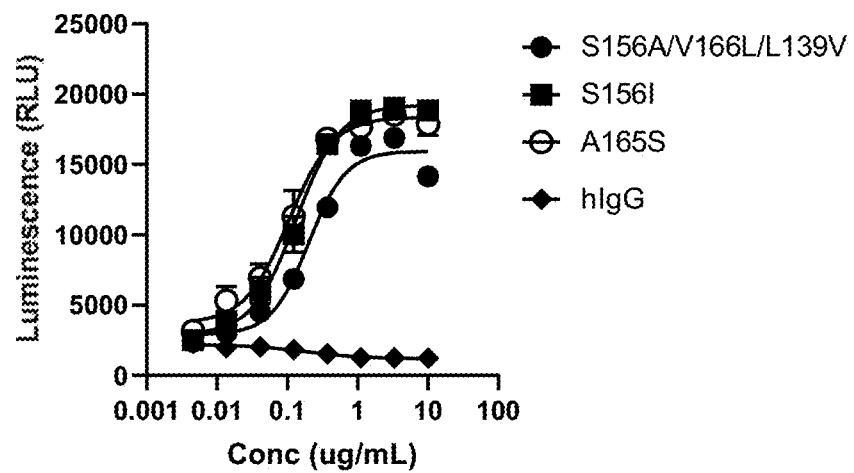

The constructed pcDNA3.4 expression vectors containing polynucleotides encoding either wild-type CD80 or mutated CD80 variants described in Table 1 and FIGS. 13A and 24 were transfected into Expi293F cells using ExpiFectamine 293 transfection reagent (Thermo Fisher Scientific). ExpiFectamine 293 Transfection Enhancer 1 and Enhancer 2 were added to the well 20 hours after transfection. The cultures were incubated at 37° C. in humidified incubator at 75% humidity supplied with 5% $CO_2$. The transfected culture was harvested 6 days post transfection. The CD80-Fc Fusion Proteins expressed from the transfected Expi293F cells were purified using GE Healthcare Protein A HP SpinTrap column by incubating the supernatants and the resin at room temperature for 4 minutes. The column was washed with sodium phosphate buffer, pH7.2 and eluted with 100 mM glycine-HCl, pH 3.0. The eluents were neutralized using 1.0 M Tris-HCl, pH 9.0. The purified proteins were dialyzed into PBS buffer at pH7.2 and sterile filtered through 0.2 μm membrane. The SDS-PAGE analyses were performed and the results of mutant CD80-Fc Fusion Proteins from the analyses were summarized in FIGS. 15A-15F. All the CD80-Fc Fusion Proteins were purified to near 95% purity. The purified proteins were tested on SDS-PAGE gels in two conditions; (i) a non-reducing condition, which does not break disulfide bonds in a target fusion protein, and (ii) a reducing condition, which breaks disulfide bonds in a target fusion protein. Non-reduced (FIG. 15A) and reduced (FIG. 15B) samples loaded with each purified variant CD80-Fc Fusion protein are as follows; Lane 1: Molecular Weight Marker; Lane 2: S131F, 1.5 ug/lane; Lane 3: S131R, 1.5 ug/lane; Lane 4: S131E, 2.0 ug/lane; Lane 5: S131D, 1.6 ug/lane; Lane 6: S131Q, 1.6 ug/lane; Lane 7: A165V, 1.2 ug/lane; Lane 8: A165I, 1.6 ug/lane; Lane 9: A165F, 1.6 ug/lane; Lane 10: A165R, 1.6 ug/lane; Lane 11: A165D, 1.6 ug/lane; Lane 12: A165Q, 1.6 ug/lane. Non-reduced (FIG. 15C) and reduced (FIG. 15D) samples loaded with each purified variant CD80-Fc Fusion protein are as follows; Lane 1: Molecular Weight Marker; Lane 2: V166A, 10/lane; Lane 3: V166T, 10 ug/lane; Lane 4: V166L/L139V, 10 ug/lane; Lane 5: S156A/V155A, 10 ug/lane; Lane 6: S156A/V155I, 10 ug/lane; Lane 7: S156A/V155T, 10 ug/lane; Lane 8: S156A/T130A, 10 ug/lane; Lane 9: S156A/V166A, 10 ug/lane; Lane 10: S156A/V166L/L139V, 10 ug/lane. Non-reduced (FIG. 15E) and reduced (FIG. 15F) samples loaded with each purified variant CD80-Fc Fusion protein are as follows; Lane 1: Molecular Weight Marker; Lane 2: S131V, 10 ug/lane; Lane 3: V155A, 10 ug/lane; Lane 4: V155I, 10 ug/lane; Lane 5: V155T, 10 ug/lane.

TABLE 2

| | Primers for Site-directed Mutagenesis |
|---|---|
| S156I-f | CCATCAACACAACCGTGATCCAAGACCCCGAAACAG (SEQ ID NO: 16) |
| S156I-r | CTGTTTCGGGGTCTTGGATCACGGTTGTGTTGATGG (SEQ ID NO: 17) |
| A165S-f | CCGAAACAGAGCTCTACAGCGTGAGTAGTAAGCTGG (SEQ ID NO: 18) |
| A165S-r | CCAGCTTACTACTCACGCTGTAGAGCTCTGTTTCGG (SEQ ID NO: 19) |
| S131A-f | ATCATCTGCAGTACCGCTGGTGGGTTCCCTG (SEQ ID NO: 20) |
| S131A-r | CAGGGAACCCACCAGCGGTACTGCAGATGAT (SEQ ID NO: 21) |

TABLE 2-continued

Primers for Site-directed Mutagenesis

| | |
|---|---|
| S156F-f | CATCAACACAACCGTGTTCCAAGACCCCGAAACAGAGCTCTAC (SEQ ID NO: 22) |
| S156F-r | GTTTCGGGGTCTTGGAACACGGTTGTGTTGATGGCGTTGAG (SEQ ID NO: 23) |
| S156R-f | CATCAACACAACCGTGAGGCAAGACCCCGAAACAGAGCTCTAC (SEQ ID NO: 24) |
| S156R-r | GTTTCGGGGTCTTGCCTCACGGTTGTGTTGATGGCGTTGAG (SEQ ID NO: 25) |
| S156E-f | CATCAACACAACCGTGGAGCAAGACCCCGAAACAGAGCTCTAC (SEQ ID NO: 26) |
| S156E-r | GTTTCGGGGTCTTGCTCCACGGTTGTGTTGATGGCGTTGAG (SEQ ID NO: 27) |
| S156D-f | CATCAACACAACCGTGGACCAAGACCCCGAAACAGAGCTCTAC (SEQ ID NO: 28) |
| S156D-r | GTTTCGGGGTCTTGGTCCACGGTTGTGTTGATGGCGTTGAG (SEQ ID NO: 29) |
| S156Q-f | CATCAACACAACCGTGCAGCAAGACCCCGAAACAGAGCTCTAC (SEQ ID NO: 30) |
| S156Q-r | GTTTCGGGGTCTTGCTGCACGGTTGTGTTGATGGCGTTGAG (SEQ ID NO: 31) |
| S131V-f | CATCTGCAGTACCGTGGGTGGGTTCCCTGAGCCCCATCTC (SEQ ID NO: 32) |
| S131V-r | CAGGGAACCCACCCACGGTACTGCAGATGATTCTCCTG (SEQ ID NO: 33) |
| S131I-f | CATCTGCAGTACCATCGGTGGGTTCCCTGAGCCCCATCTC (SEQ ID NO: 34) |
| S131I-r | CAGGGAACCCACCGATGGTACTGCAGATGATTCTCCTG (SEQ ID NO: 35) |
| S131F-f | CATCTGCAGTACCTTCGGTGGGTTCCCTGAGCCCCATCTC (SEQ ID NO: 36) |
| S131F-r | CAGGGAACCCACCGAAGGTACTGCAGATGATTCTCCTG (SEQ ID NO: 37) |
| S131R-f | CATCTGCAGTACCAGGGGTGGGTTCCCTGAGCCCCATCTC (SEQ ID NO: 38) |
| S131R-r | CAGGGAACCCACCCCTGGTACTGCAGATGATTCTCCTG (SEQ ID NO: 39) |
| S131E-f | CATCTGCAGTACCGAGGGTGGGTTCCCTGAGCCCCATCTC (SEQ ID NO: 40) |
| S131E-r | CAGGGAACCCACCCTCGGTACTGCAGATGATTCTCCTG (SEQ ID NO: 41) |
| S131D-f | CATCTGCAGTACCGACGGTGGGTTCCCTGAGCCCCATCTC (SEQ ID NO: 42) |
| S131D-r | CAGGGAACCCACCGTCGGTACTGCAGATGATTCTCCTG (SEQ ID NO: 43) |
| S131Q-f | CATCTGCAGTACCCAGGGTGGGTTCCCTGAGCCCCATCTC (SEQ ID NO: 44) |
| S131Q-r | CAGGGAACCCACCCTGGGTACTGCAGATGATTCTCCTG (SEQ ID NO: 45) |

TABLE 2-continued

Primers for Site-directed Mutagenesis

| | |
|---|---|
| A165V-f | GAAACAGAGCTCTACGTGGTGAGTAGTAAGCTGGACTTTAAC (SEQ ID NO: 46) |
| A165V-r | CTTACTACTCACCACGTAGAGCTCTGTTTCGGGGTCTTG (SEQ ID NO: 47) |
| A165I-f | GAAACAGAGCTCTACATCGTGAGTAGTAAGCTGGACTTTAAC (SEQ ID NO: 48) |
| A165I-r | CTTACTACTCACGATGTAGAGCTCTGTTTCGGGGTCTTG (SEQ ID NO: 49) |
| A165F-f | GAAACAGAGCTCTACTTCGTGAGTAGTAAGCTGGACTTTAAC (SEQ ID NO: 50) |
| A165F-r | CTTACTACTCACGAAGTAGAGCTCTGTTTCGGGGTCTTG (SEQ ID NO: 51) |
| A165R-f | GAAACAGAGCTCTACAGGGTGAGTAGTAAGCTGGACTTTAAC (SEQ ID NO: 52) |
| A165R-r | CTTACTACTCACCCTGTAGAGCTCTGTTTCGGGGTCTTG (SEQ ID NO: 53) |
| A165E-f | GAAACAGAGCTCTACGAGGTGAGTAGTAAGCTGGACTTTAAC (SEQ ID NO: 54) |
| A165E-r | CTTACTACTCACCTCGTAGAGCTCTGTTTCGGGGTCTTG (SEQ ID NO: 55) |
| A165D-f | GAAACAGAGCTCTACGACGTGAGTAGTAAGCTGGACTTTAAC (SEQ ID NO: 56) |
| A165D-r | CTTACTACTCACGTCGTAGAGCTCTGTTTCGGGGTCTTG (SEQ ID NO: 57) |
| A165Q-f | GAAACAGAGCTCTACCAGGTGAGTAGTAAGCTGGACTTTAAC (SEQ ID NO: 58) |
| A165Q-r | CTTACTACTCACCTGGTAGAGCTCTGTTTCGGGGTCTTG (SEQ ID NO: 59) |

TABLE 3

Primers for Site-directed Mutagenesis

| Primer ID | primer sequence |
|---|---|
| T130A-f | CAGGAGAATCATCTGCAGTGCATCTGGTGGGTTCCCTGAG (SEQ ID NO: 60) |
| T130A-r | CTCAGGGAACCCACCAGATGCACTGCAGATGATTCTCCTG (SEQ ID NO: 61) |
| S131V-f | GAGAATCATCTGCAGTACCGTTGGTGGGTTCCCTGAGCC (SEQ ID NO: 62) |
| S131V-r | GGCTCAGGGAACCCACCAACGGTACTGCAGATGATTCTC (SEQ ID NO: 63) |
| L139V-f | GTTCCCTGAGCCCCATGTTAGCTGGCTGGAGAACG (SEQ ID NO: 64) |
| L139V-r | CGTTCTCCAGCCAGCTAACATGGGGCTCAGGGAAC (SEQ ID NO: 65) |
| V155A-f | CAACGCCATCAACACAACCGCATCCCAAGACCCCGAAACAG (SEQ ID NO: 66) |
| V155A-r | CTGTTTCGGGGTCTTGGGATGCGGTTGTGTTGATGGCGTTG (SEQ ID NO: 67) |
| V155I-f | CAACGCCATCAACACAACCATCTCCCAAGACCCCGAAACAG (SEQ ID NO: 68) |

TABLE 3-continued

Primers for Site-directed Mutagenesis

| Primer ID | primer sequence |
|---|---|
| V155I-r | CTGTTTCGGGGTCTTGGGAGATGGTTGTGTTGATGGCGTTG (SEQ ID NO: 69) |
| V155T-f | CAACGCCATCAACACAACCACCTCCCAAGACCCCGAAACAG (SEQ ID NO: 70) |
| V155T-r | CTGTTTCGGGGTCTTGGGAGGTGGTTGTGTTGATGGCGTTG (SEQ ID NO: 71) |
| S156A-f | GCCATCAACACAACCGTGGCACAAGACCCCGAAACAGAG (SEQ ID NO: 72) |
| S156A-r | CTCTGTTTCGGGGTCTTGTGCCACGGTTGTGTTGATGGC (SEQ ID NO: 73) |
| V166A-f | CGAAACAGAGCTCTACGCCGCAAGTAGTAAGCTGGACTTTAAC (SEQ ID NO: 74) |
| V166A-r | GTTAAAGTCCAGCTTACTACTTGCGGCGTAGAGCTCTGTTTCG (SEQ ID NO: 75) |
| V166L-f | CCGAAACAGAGCTCTACGCCCTCAGTAGTAAGCTGGACTTTAAC (SEQ ID NO: 76) |
| V166L-r | GTTAAAGTCCAGCTTACTACTGAGGGCGTAGAGCTCTGTTTCGG (SEQ ID NO: 77) |
| V166T-f | CCGAAACAGAGCTCTACGCCACCAGTAGTAAGCTGGACTTTAAC (SEQ ID NO: 78) |
| V166T-r | GTTAAAGTCCAGCTTACTACTGGTGGCGTAGAGCTCTGTTTCGG (SEQ ID NO: 79) |
| S155A/S156A-f | CAACGCCATCAACACAACCGCAGCACAAGACCCCGAAACAGAGC (SEQ ID NO: 80) |
| S155A/S156A-r | GCTCTGTTTCGGGGTCTTGTGCTGCGGTTGTGTTGATGGCGTTG (SEQ ID NO: 81) |
| V155I/S156A-f | CAACGCCATCAACACAACCATCGCCCAAGACCCCGAAACAGAGC (SEQ ID NO: 82) |
| V155I/S156A-r | GCTCTGTTTCGGGGTCTTGGGCGATGGTTGTGTTGATGGCGTTG (SEQ ID NO: 83) |
| V155T/S156A-f | CAACGCCATCAACACAACCACCGCCCAAGACCCCGAAACAGAG (SEQ ID NO: 84) |
| V155T/S156A-r | CTCTGTTTCGGGGTCTTGGGCGGTGGTTGTGTTGATGGCGTTG (SEQ ID NO: 85) |

Example 2

Assessment of Binding Affinities of CD80 Variants to CTLA-4, PD-L1 and CD28 by ELISA and Biacore (1) CD80 Mutant Binding Affinity by ELISA:

For testing binding affinity by ELISA, at first ELISA plates were coated with 1 ug/mL hCTLA-4 (recombinant His Tag from Sino Biological) at 4° C. overnight. The next day, the hCTLA-4 solution was removed and the plates were blocked with 1% BSA at room temperature for 1 hour. After removing the 1% BSA solution, the plates were washed with PBST (phosphate buffered saline with 0.05% of Tween-20) three times. The samples of the purified CD80 variants for this binding assay were added at 100 uL/well in duplicate with 1:3 serial dilutions starting at the concentration of 4 ug/mL and incubated at room temperature for 2 hours with agitation. After washing with PBST three times, a secondary antibody, 100 uL/well of 1:10,000 dilution of HRP-anti-hIgG, was added and incubated at room temperature for 1 hour with agitation. The plates were wash three times with PBST, and a 100 uL/well of TMB substrate was added. The plates were incubated until the color was developed. The stop-solution was added to stop the reaction. The plates were read at OD450.

The similar ELISA experiments were performed for CD28 and PD-L1 recombinant proteins, respectively except the plates were coated with 2 ug/mL of recombinant CD28 and PD-L1 proteins (recombinant His Tag from Sino Biological) and the dilutions of CD80 variants were started at 20 ug/mL.

The $EC_{50}$ values of CD80 variants binding to CTLA-4, CD28 or PD-L1 were determined by comparing to $EC_{50}$ of wild-type CD80 on each plate.

The results of binding affinity assays by ELISA were presented in FIGS. 16A-16F (binding affinity of CD80 variants to CTLA-4). Table 4 summarizes results of binding assays presented in FIGS. 16A-16E with top OD450 values of each tested CD80-Fc Fusion protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay. Table 5 summarizes results of binding assays presented in FIG. 16F with top OD450 values of each tested CD80-Fc Fusion protein (e.g. T130A, S131V, L139V, V155A, V155I, V155T, S156A, V166A, V166L, V166T, V155A/S156A, V155I/S156A, V155T/S156A, and CD80-WT), along with $EC_{50}$ (ug/ml) values. The $EC_{50}$ (ug/ml) is the concentration or value of a protein that gives half maximal response in the binding assay.

The results of binding affinity assays by ELISA were presented in FIGS. 17A-17E (binding affinity of CD80 variants to CD28). Table 6 summarizes results of binding assays presented in FIGS. 17A-17E with top OD450 values of each tested CD80-Fc Fusion protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay.

The results of binding affinity assays by ELISA were presented in FIGS. 18A-18E (binding affinity of CD80 variants to PD-L1). Table 7 summarizes results of binding assays presented in FIGS. 18A-18E with top OD450 values of each tested CD80-Fc Fusion Protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay.

TABLE 4

| CTLA4-CD80 | Top OD | EC50(ug/ml) |
|---|---|---|
| CD80-WT | 1.50 | 0.0110 |
| S156I/A165S | 1.41 | 0.0120 |
| S156I/S131A | 1.59 | 0.0100 |
| A165S/S131A | 1.47 | 0.0120 |
| S156I/A165S/S131A | 1.50 | 0.0130 |
| S156F | 1.58 | 0.0090 |
| S156R | 1.57 | 0.0140 |
| S156E | 1.34 | 0.0110 |
| S156D | 1.55 | 0.0150 |
| S156Q | 1.68 | 0.0120 |
| S131V | 1.48 | 0.0200 |
| S131I | 1.60 | 0.0150 |
| S131F | 1.68 | 0.0141 |
| S131R | 1.60 | 0.0058 |
| S131E | 1.50 | 0.0130 |
| S131D | 1.30 | 0.0260 |
| S131Q | 1.46 | 0.0130 |
| A165V | 1.44 | 0.0370 |
| A165I | 1.32 | 0.0890 |
| A165F | 0.90 | 0.0310 |
| A165R | 1.01 | 0.0210 |
| A165E | 1.04 | 0.0090 |
| A165D | 0.87 | 0.0180 |
| A165Q | 0.82 | 0.0120 |

TABLE 5

|  | Top | EC50 |
|---|---|---|
| CD80-WT | 1.11 | 0.04846 |
| T130A | 1.198 | 0.01983 |
| S131V | 1.053 | 0.0321 |
| L139V | 1.314 | 0.0268 |
| V155A | 1.095 | 0.02888 |
| V155I | 0.9623 | 0.08108 |
| V155T | 0.8803 | 0.06053 |
| S156A | 1.159 | 0.04707 |
| V166A | 0.9512 | 0.06625 |
| V166L | 1.162 | 0.02897 |
| V166T | 0.9639 | 0.01365 |
| V155A/S156A | 1.151 | 0.02742 |
| V155I/S156A | 1.095 | 0.1835 |
| V155T/S156A | 0.8386 | 0.05937 |

TABLE 6

| CD28-CD80 | Top OD | EC50(ug/ml) |
|---|---|---|
| CD80-WT | 2.51 | 2.42 |
| S156I/A165S | 2.22 | 2.42 |
| S156I/S131A | 2.20 | 4.36 |
| A165S/S131A | 2.33 | 5.02 |
| S156I/A165S/S131A | 2.26 | 4.85 |
| S156F | 2.19 | 2.20 |
| S156R | 1.83 | 7.66 |
| S156E | 2.12 | 4.18 |
| S156D | 2.12 | 4.29 |
| S156Q | 2.14 | 4.05 |
| S131V | 1.27 | 32.46 |
| S131I | 1.76 | 10.75 |
| S131F | 1.22 | . . . |
| S131R | 1.75 | 23.26 |
| S131E | 1.72 | . . . |
| S131D | 1.31 | . . . |
| S131Q | 1.63 | 13.60 |
| A165V | 1.02 | 135.30 |
| A165I | 0.67 | 2.10 |
| A165F | 0.74 | 14.86 |
| A165R | 1.10 | . . . |
| A165E | 1.78 | 34.07 |
| A165D | 1.36 | . . . |
| A165Q | 1.76 | 157.10 |

TABLE 7

| PD-L1-CD80 | Top OD | EC50(ug/ml) |
|---|---|---|
| CD80-WT | 1.07 | 0.98 |
| S156I/A165S | 0.70 | 1.17 |
| S156I/S131A | 0.74 | 0.52 |
| A165S/S131A | 0.83 | 1.23 |
| S156I/A165S/S131A | 0.71 | 1.96 |
| S156F | 0.94 | 0.37 |
| S156R | 0.91 | 0.49 |
| S156E | 0.72 | 0.67 |
| S156D | 0.83 | 0.57 |
| S156Q | 0.92 | 0.55 |
| S131V | 0.94 | 0.40 |
| S131I | 0.87 | 0.24 |
| S131F | 0.96 | 0.21 |
| S131R | 0.79 | 0.58 |
| S131E | 0.83 | 0.51 |
| S131D | 0.89 | 0.28 |
| S131Q | 0.76 | 0.48 |
| A165V | 0.81 | 0.14 |
| A165I | 0.81 | 0.19 |

TABLE 7-continued

| PD-L1-CD80 | Top OD | EC50(ug/ml) |
|---|---|---|
| A165F | 0.94 | 0.38 |
| A165R | 0.97 | 0.26 |
| A165E | 0.80 | 0.32 |
| A165D | 0.82 | 0.30 |
| A165Q | 0.92 | 0.29 |

Figure 19:
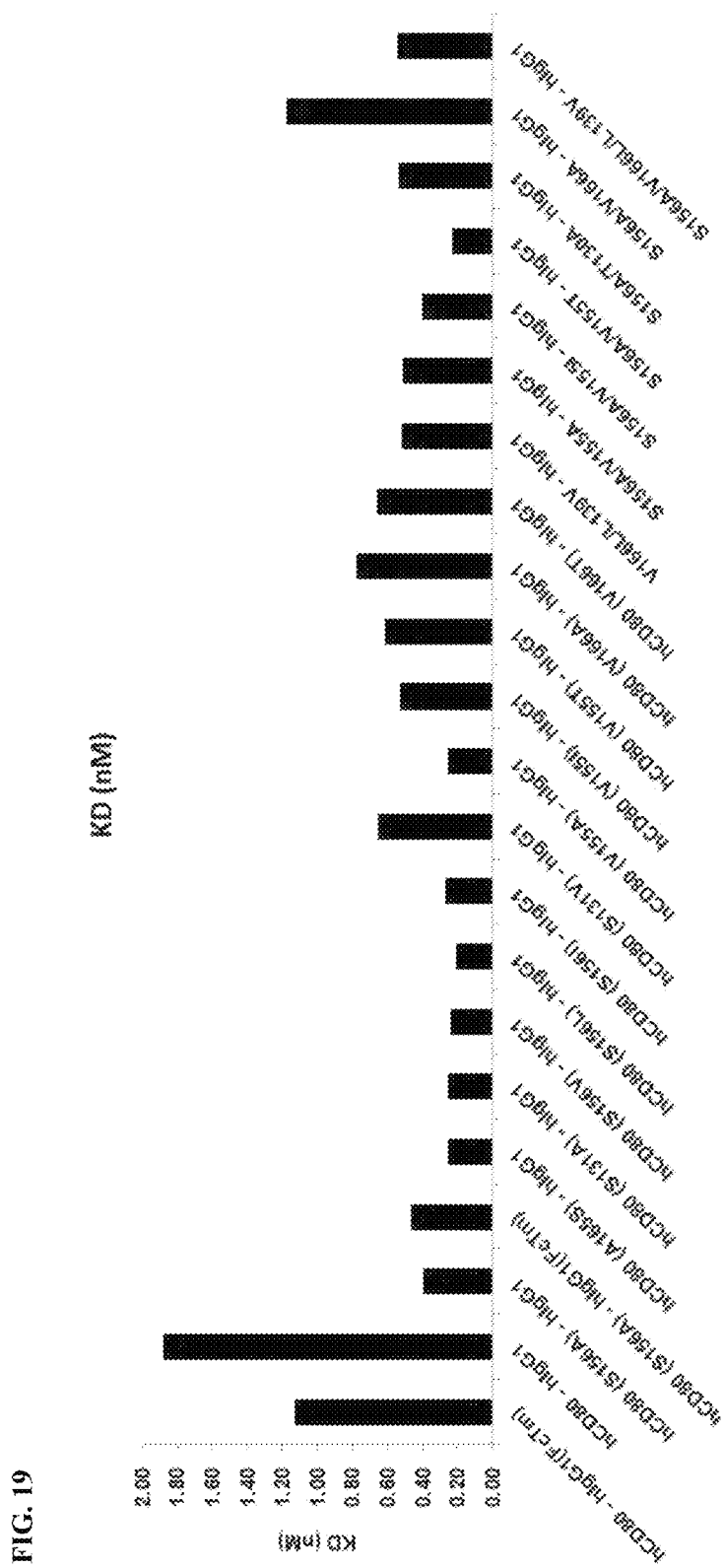
FIG. 19 depicts results of binding assays of each variant CD80-Fc Fusion protein including single, double and triple mutations, to a binding partner human CTLA-4, using BIAcore model X100.

(2) CD80 Mutant Binding Affinity Measured by BIAcore:

For measuring binding affinity by BlAcore, affinity measurements were carried out on BIAcore model X100 (Biacore/GE Healthcare, Piscataway, NJ) at 25° C. using PBST buffer (20 mM PB+150 mM NaCl+0.05% Tween20, pH 7.4) as a running buffer. NTA sensor chip (catalogue BR-1000-07; GE Healthcare) was chelated with nickel ion (0.5 mM NiC12) in one flow cell at a flow rate of 10 ul/min for 1 minute to capture hCTLA-4 containing a poly-histidine tag at the C-terminus (catalogue 11159-H08H; Sino Biological). The hCTLA-4 solution was injected at a flow rate of 10 ul/min for 2 minutes, then followed by a stabilization time of 3 minutes. hCD80-Fc fusion mutants was then injected in a 2-fold dilution series from sub nM to several hundred nM at a flow rate of 30 ul/min for 3 minutes, and dissociation was monitored for 12 minutes. The regeneration procedure was performed by injecting 350 mM EDTA buffer at a flow rate of 30 ul/min for 3 minutes to remove nickel and any chelated protein. Kinetic analysis was done by simultaneously fitting the association and dissociation phases of the sensorgram using the 1:1 Langmuir binding model in BlAevaluation software (Biacore) as supplied by the manufacturer. Double referencing was applied in each analysis to eliminate background responses from the reference surface and buffer only control. FIG. 19 depicts results of binding assays of each variant human CD80-IgG1 Fc Fusion protein including single, double and triple mutations (e.g. hCD80 (S156A)-hIgG1, hCD80(S156A)-hIgG1 (FcTm), hCD80 (A165S)-hIgG1, hCD80(S131A)-hIgG1, hCD80(S156V)-hIgG1, hCD80(S156L)-hIgG1, hCD80(S156Q-hIgG1, hCD80(S131V)-hIgG1, hCD80(V155A)-hIgG1, hCD80 (V155I-hIgG1, hCD80(V155T)-hIgG1, hCD80(V166A)-hIgG1, hCD80(V166T)-hIgG1, hCD80(V166L/L139V)-hIgG1, hCD80(S156A/V155A)-hIgG1, hCD80(S156A/V155I-hIgG1, hCD80(S156A/V166T)-hIgG1, hCD80 (S156A/T130A)-hIgG1, hCD80(S156A/V166A)-hIgG1, hCD80(S156A/V166L/L139V)-hIgG1) to a binding partner human CTLA-4, compared to a wild-type and unmodified CD80-Fc fusion protein as a control (e.g. hCD80-hLgG1 (FcTm, Fc triple mutations for effectorless Fc) and hCD80-hIgG1)), using BIAcore model X100.

As shown in FIG. 19, all CD80 variants (mutant hCD80-Fc Fusion Proteins) have higher binding affinity to CTLA-4 than wild-type CD80-Fc fusion protein.

(3) CD80 Mutant Binding Affinity Measured by Bio-Layer Interferometry (BLI) Biosensor The kinetic affinities of CD80 variants to PD-L1 or CD28 were analyzed by ForteBio's Octet RED384 system. hPD-L1-His or hCD28-His was immobilized on the surface of the biosensor by capture-based method (sensor type: HIS1K-Anti-Penta-HIS). After the baseline step, biosensors are dipped into a solution containing different concentration of CD80 variants. Experimental temperature was 30° C. and the rotation rate was 1000 rpm/min. Running buffer was 20 mM PB, 150 mM NaCl, 0.05% Tween20, pH7.4, while the regeneration solution was 10 mM Glycine-HCl, pH1.5. Table 8 summarizes results of kinetic affinities of CD80 variants to hPD-L1. Table 9 summarizes results of kinetic affinities of CD80 variants to CD28.

TABLE 8

Kinetic affinities of CD80 variants to hPD-L1

| Sample ID | Ligand | Kd (M) | Kon(1/Ms) | Kdis(1/s) |
|---|---|---|---|---|
| WT | hPD-L1-His | 2.59E-08 | 5.28E+04 | 2.68E-03 |
| S131V | hPD-L1-His | 1.75E-07 | 2.01E+05 | 3.15E-02 |
| V155A | hPD-L1-His | 3.61E-07 | 2.23E+05 | 8.04E-02 |
| V155I | hPD-L1-His | 7.85E-08 | 3.03E+05 | 2.38E-02 |
| V155T | hPD-L1-His | 4.96E-08 | 4.03E+05 | 2.00E-02 |
| V166A | hPD-L1-His | 6.62E-08 | 3.69E+06 | 2.44E-02 |
| V166T | hPD-L1-His | 2.34E-08 | 3.61E+06 | 8.45E-03 |
| V166L/L139V | hPD-L1-His | 1.23E-07 | 2.16E+06 | 2.65E-02 |
| S156A/V155A | hPD-L1-His | 6.87E-05 | 1.39E+03 | 9.57E-02 |
| S156A/V155I | hPD-L1-His | 2.65E-07 | 1.95E+05 | 5.18E-02 |
| S156A/V155T | hPD-L1-His | 3.74E-07 | 2.31E+05 | 8.66E-02 |
| S156A/T130A | hPD-L1-His | 3.91E-07 | 1.82E+05 | 7.12E-02 |
| S156A/V166A | hPD-L1-His | low | low | low |
| S156A/V166L/L139V | hPD-L1-His | 2.28E-06 | 1.70E+05 | 3.88E-02 |
| S156I | hPD-L1-His | 2.15E-08 | 3.34E+05 | 7.17E-03 |
| A165S | hPD-L1-His | 1.99E-08 | 2.87E+05 | 5.71E-03 |
| S131A | hPD-L1-His | low | low | low |
| S156I/A165S | hPD-L1-His | 2.07E-08 | 2.67E+05 | 5.53E-03 |
| S156I/S131A | hPD-L1-His | 1.39E-08 | 2.32E+05 | 3.23E-03 |
| A165S/S131A | hPD-L1-His | 4.00E-08 | 2.42E+05 | 9.70E-03 |
| S156I/A165S/S131A | hPD-L1-His | 3.20E+08 | 2.49E+05 | 7.98E-03 |
| S156F | hPD-L1-His | 2.56E-08 | 2.54E+05 | 6.52E-03 |
| S156R | hPD-L1-His | 4.61E-08 | 2.51E+05 | 1.16E-02 |
| S156E | hPD-L1-His | 3.16E-08 | 2.76E+05 | 8.74E-03 |
| S156D | hPD-L1-His | 2.60E-08 | 2.46E+05 | 6.41E-03 |
| S156Q | hPD-L1-His | low | low | low |
| S131V | hPD-L1-His | 8.95E-08 | 1.62E+05 | 1.45E-02 |
| S131I | hPD-L1-His | 2.53E-08 | 2.61E+05 | 6.59E-03 |
| S131F | hPD-L1-His | 3.38E-08 | 3.42E+05 | 1.16E-02 |
| S131R | hPD-L1-His | 3.40E-08 | 2.54E+05 | 8.62E-03 |
| S131E | hPD-L1-His | 2.87E-08 | 2.86E+05 | 8.20E-03 |
| S131D | hPD-L1-His | 4.67E-08 | 2.39E+05 | 1.11E-02 |
| S131Q | hPD-L1-His | 4.00E-08 | 2.42E+05 | 9.67E-03 |
| A165V | hPD-L1-His | 1.07E-07 | 2.73E+05 | 2.93E-02 |
| A165I | hPD-L1-His | 2.47E-08 | 4.79E+05 | 1.18E-02 |
| A165F | hPD-L1-His | 4.18E-08 | 3.91E+05 | 1.63E-02 |
| A165R | hPD-L1-His | 3.48E-08 | 3.29E+05 | 1.14E-02 |
| A165E | hPD-L1-His | 3.70E-08 | 4.44E+06 | 1.64E-02 |
| A165D | hPD-L1-His | 4.37E-08 | 3.33E+06 | 1.45E-02 |
| A165Q | hPD-L1-His | 8.26E-08 | 2.99E+06 | 2.47E-02 |

TABLE 9

Kinetic affinities of CD80 variants to CD28

| Sample ID | Ligand | Kd (M) | Kon(1/Ms) | Kdis(1/s) |
|---|---|---|---|---|
| WT | hCD28-His | 1.81E-08 | 6.07E+05 | 0.011 |
| S131V | hCD28-His | 1.90E-08 | 1.79E+06 | 3.41E-02 |
| V155A | hCD28-His | 4.29E-08 | 1.33E+06 | 5.72E-02 |
| V155I | hCD28-His | 8.63E-09 | 3.04E+06 | 2.62E-02 |
| V155T | hCD28-His | 9.61E-09 | 2.41E+06 | 2.32E-02 |
| V166A | hCD28-His | 2.58E-08 | 1.71E+06 | 4.42E-02 |
| V166T | hCD28-His | 2.58E-08 | 1.58E+06 | 4.06E-02 |
| V166L/L139V | hCD28-His | 1.36E-08 | 2.24E+06 | 3.06E-02 |
| S156A/V155A | hCD28-His | 1.68E-07 | 4.74E+05 | 7.97E-02 |
| S156A/V155I | hCD28-His | 2.77E-08 | 1.45E+06 | 4.00E-02 |
| S156A/V155T | hCD28-His | 8.26E-09 | 4.40E+06 | 3.64E-02 |
| S156A/T130A | hCD28-His | 5.39E-09 | 3.30E+06 | 1.78E-02 |
| S156A/V166A | hCD28-His | 2.32E-07 | 1.81E+05 | 4.21E-02 |
| S156A/V166L/L139V | hCD28-His | 2.10E-08 | 1.95E+06 | 4.10E-02 |
| S156I | hCD28-His | 1.50E-08 | 1.85E+06 | 2.78E-02 |
| A165S | hCD29-His | 1.14E-08 | 2.32E+06 | 2.65E-02 |
| S131A | hCD28-His | 4.40E-06 | 2.98E+04 | 1.31E-01 |
| S156I/A165S | hCD28-His | 2.57E-09 | 3.53E+06 | 9.07E-03 |
| S156I/S131A | hCD28-His | 3.67E-09 | 3.27E+06 | 1.20E-02 |
| A165S/S131A | hCD28-His | 8.79E-09 | 2.45E+06 | 2.15E-02 |
| S156I/A165S/S131A | hCD28-His | 3.45E-09 | 3.02E+06 | 1.04E-02 |
| S156F | hCD28-His | 1.74E-08 | 2.00E+06 | 3.48E-02 |
| S156R | hCD28-His | 1.11E-08 | 2.62E+06 | 2.90E-02 |

TABLE 9-continued

Kinetic affinities of CD80 variants to CD28

| Sample ID | Ligand | Kd (M) | Kon(1/Ms) | Kdis(1/s) |
|---|---|---|---|---|
| S156E | hCD28-His | 5.94E−09 | 3.45E+06 | 2.05E−02 |
| S156D | hCD28-His | 4.64E−09 | 3.74E+06 | 1.73E−02 |
| S156Q | hCD28-His | low | low | low |
| S131V | hCD28-His | 5.32E−09 | 2.03E+06 | 1.08E−02 |
| S131I | hCD28-His | 6.60E−09 | 1.78E+06 | 1.18E−02 |
| S131F | hCD28-His | 2.06E−08 | 1.56E+06 | 3.20E−02 |
| S131R | hCD28-His | 1.17E−08 | 2.47E+06 | 2.90E−02 |
| S131E | hCD28-His | 7.69E−09 | 3.44E+06 | 2.65E−02 |
| S131D | hCD28-His | 6.95E−09 | 3.16E+06 | 2.20E−02 |
| S131Q | hCD28-His | 1.01E−08 | 2.96E+06 | 3.00E−02 |
| A165V | hCD28-His | 2.04E−08 | 1.87E+06 | 3.82E−02 |
| A165I | hCD28-His | 1.96E−07 | 5.28E+05 | 1.03E−01 |
| A165F | hCD28-His | 2.04E−08 | 1.50E+06 | 3.06E−02 |
| A165R | hCD28-His | 4.03E−08 | 1.80E+06 | 7.27E−02 |
| A165E | hCD28-His | 2.06E−08 | 3.01E+06 | 6.19E−02 |
| A165D | hCD28-His | 1.13E−08 | 3.46E+06 | 3.91E−02 |
| A165Q | hCD28-His | 1.79E−08 | 3.02E+06 | 5.41E−02 |

Example 3

Assessment of Cell Surface Binding Affinities of CD80 Variants by FACS (1) Generation of Stable Cells Overexpressing Target of Interest (hCTLA-4, hCD28, and hPD-L1) using Flp-In™ Cell Line for FACS Assay The Expression Vector containing polynucleotide encoding hCD28, hCTLA-4, or hPD-L1 was co-transfected with a 9:1 ratio of pOG44: pcDNA™5/FRT plasmid into mammalian Flp-In™ 293 host cells (Invitrogen). Twenty-four hours after transfection, the cells were washed and fresh medium were added to the cells. Hygromycin B (at 200 ug/mL final concentration) was added to the transfected cells 48 hours after transfection. The medium containing 200 ug/mL hygromycin B was changed every 5 days until single clone was selected. All the single clones were analyzed by FACS binding assays. The best expressing single clones for hCD28, hCTLA-4 and hPD-L1, respectively were expanded, and preserved in the freezing medium containing D-MEM (high glucose), 10% FBS, 2 mM L-glutamine, and 1% Pen-Strep in liquid nitrogen. The three stable cell lines were characterized by FACS binding assay as described below.

(2) Cell Surface Binding Assay by FACS

The binding affinity (EC50) of CD80 variants to Flp-in 293 cells overexpressing CD28, Flp-in 293 cells overexpressing CTLA4 and Flp-in 293 cells overexpressing PD-L1, respectively were determined by FACS. The FACS binding assays were performed as follows: Flp-in 293 cells overexpressing CD28, Flp-in 293 cells overexpressing CTLA4 and Flp-in 293 cells overexpressing PD-L1 were stained with a serial diluted mutant CD80-Fc fusion protein on ice for 1 hour, (i) with concentrations of 100 μg/ml, 30 μg/ml, 10 μg/ml, 3 μg/ml, 1 μg/ml, 0.3 μg/ml, 0.1 μg/ml, and 0.03 μg/ml for either Flp-in 293 cells overexpressing CD28 or Flp-in 293 cells overexpressing PD-L1, and (ii) with concentrations of 3 μg/ml, 1 μg/ml, 0.3 μg/ml, 0.1 μg/ml, 0.03 μg/ml, 0.01 μg/ml, 0.03 μg/ml, and 0.001 μg/ml for Flp-in 293 cells overexpressing CTLA4. The cells were washed with staining buffer (PBS+2% fetal bovine serum) to remove free CD80-Fc Fusion Proteins, and then stained with AlexFluor 488-conjugated anti-human IgG antibody for 30 min on ice. The cells were washed and analyzed by FACS.

Figure 20A:
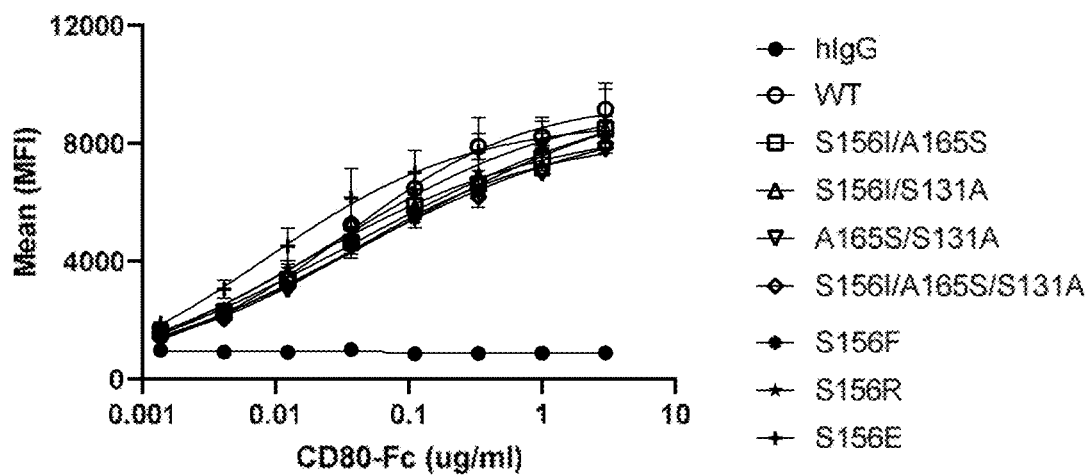
FIG. 20A depicts results of cell surface binding assays by FACS to test binding affinity of variant CD80-Fc Fusion Proteins to Flp-in 293 cells expressing CTLA-4. Types of variant CD80 polypeptides tested herein are as follows: amino acid substitutions/mutations at two positions (S156I/A165S, S156I/S131A, and A165S/S131A—double substitutions/mutations), three positions (S156I/A165S/S131A—triple substitutions/mutations) and one position at S156 (S156F, S156R, and S156E). CD80-WT protein is used as a positive control and human IgG1 protein is a negative control.
Figure 20B:
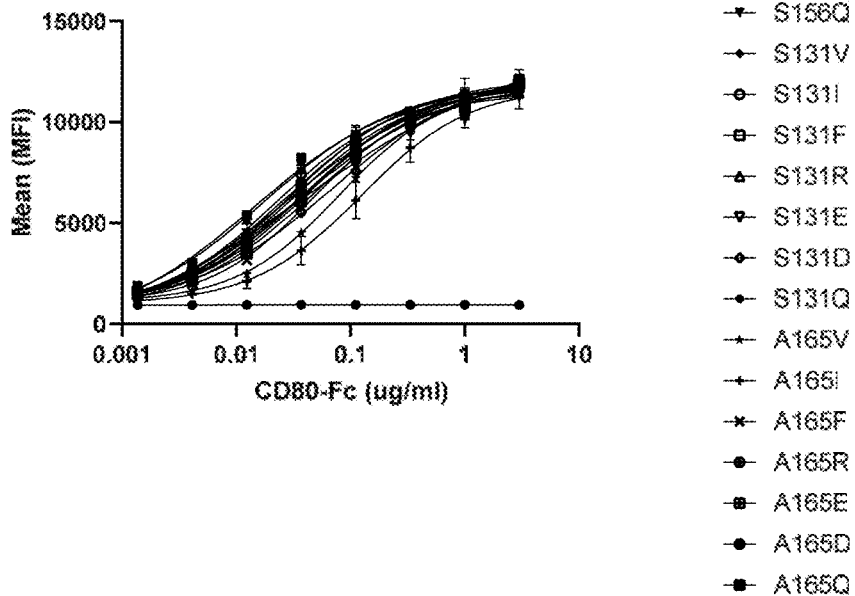
FIG. 20B depicts results of cell surface binding assays by FACS to test binding affinity of variant CD80-Fc Fusion Proteins to Flp-in 293 cells expressing CTLA-4. Types of variant CD80 polypeptides tested herein are as follows: a single amino acid substitution/mutation at position at S156, S131, or A165 (S156D, S156Q, S131V, S131I, S131F, S131R, S131E, S131D, S131Q, A165V, A165I, A165F, A165R, A165E, A165D, and A165Q). CD80-WT protein is used as a positive control and human IgG1 protein is a negative control.

The results of cell surface binding affinity assays by FACS were presented in FIGS. 20A-20B (binding affinity of CD80 variants to CTLA-4-overexpressing Flp-in 293 cells). Tables 10 and 11 summarize results of cell surface binding affinity assays presented in FIGS. 20A-20B with top MFI (Mean Fluorescence Intensity) values of each tested CD80-Fc Fusion protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay.

Figure 21A:
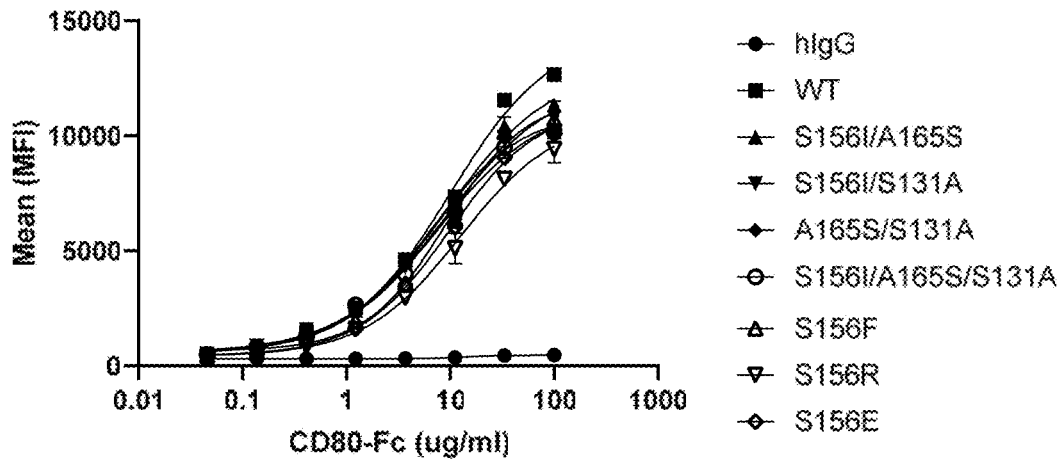
FIG. 21A depicts results of cell surface binding assays by FACS to test binding affinity of variant CD80-Fc Fusion Proteins to Flp-in 293 cells expressing CD28. Types of variant CD80 polypeptides tested herein are as follows: amino acid substitutions/mutations at two positions (S156I/A165S, S156I/S131A, and A165S/S131A—double substitutions/mutations), three positions (S156I/A165S/S131A—triple substitutions/mutations) and one position at S156 (S156F, S156R, and S156E). CD80-WT protein is used as a positive control and human IgG1 protein is a negative control.
Figure 21B:
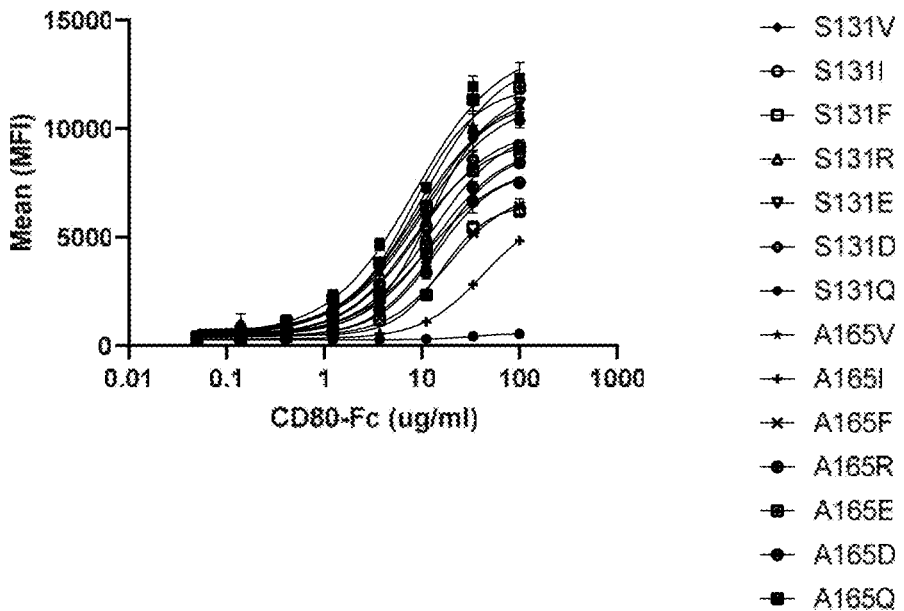
FIG. 21B depicts results of cell surface binding assays by FACS to test binding affinity of variant CD80-Fc Fusion Proteins to Flp-in 293 cells expressing CD28. Types of variant CD80 polypeptides tested herein are as follows: a single amino acid substitution/mutation at position at S156, S131, or A165 (S156D, S156Q, S131V, S131I, S131F, S131R, S131E, S131D, S131Q, A165V, A165I, A165F, A165R, A165E, A165D, and A165Q). CD80-WT protein is used as a positive control and human IgG1 protein is a negative control.

The results of cell surface binding affinity assays by FACS were presented in FIGS. 21A-21B (binding affinity of CD80 variants to CD28-overexpressing Flp-in 293 cells). Tables 12 and 13 summarize results of cell surface binding affinity assays presented in FIGS. 21A-21B with top MFI (Mean Fluorescence Intensity) values of each tested CD80-Fc Fusion protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay.

TABLE 10

| | Top (MFI) | EC50 (ug/ml) |
|---|---|---|
| WT | 8526 | 0.034 |
| S156I/A165S | 8379 | 0.040 |
| S156I/S131A | 7955 | 0.013 |
| A165S/S131A | 7821 | 0.036 |
| S156I/A165S/S131A | 8071 | 0.031 |
| S156F | 8432 | 0.068 |
| S156R | 8478 | 0.027 |
| S156E | 8794 | 0.008 |

TABLE 11

| | Top (MFI) | EC50 (ug/ml) |
|---|---|---|
| WT | 11890 | 0.014 |
| S156D | 11950 | 0.017 |
| S156Q | 11958 | 0.023 |
| S131V | 11719 | 0.038 |
| S131I | 11772 | 0.028 |
| S131F | 11911 | 0.046 |
| S131R | 11766 | 0.034 |
| S131E | 12056 | 0.042 |
| S131D | 11728 | 0.069 |
| S131Q | 11827 | 0.029 |
| A165V | 11769 | 0.081 |
| A165I | 10839 | 0.124 |
| A165F | 11308 | 0.046 |
| A165R | 11821 | 0.032 |
| A165E | 11931 | 0.040 |
| A165D | 12118 | 0.030 |
| A165Q | 11980 | 0.043 |

Figure 22A:
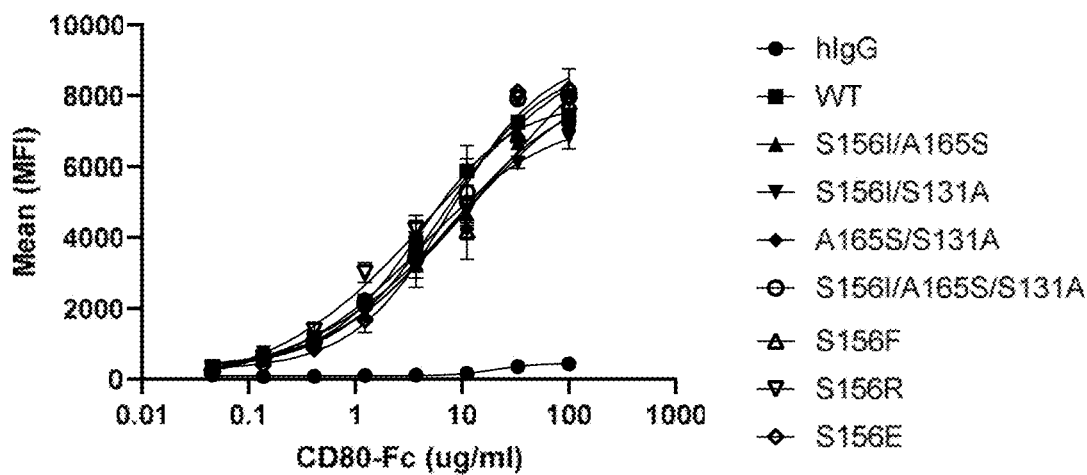
FIG. 22A depicts results of cell surface binding assays by FACS to test binding affinity of variant CD80-Fc Fusion Proteins to Flp-in 293 cells expressing PD-L1. Types of variant CD80 polypeptides tested herein are as follows: amino acid substitutions/mutations at two positions (S156I/A165S, S156I/S131A, and A165S/S131A—double substitutions/mutations), three positions (S156I/A165S/S131A—triple substitutions/mutations) and one position at S156 (S156F, S156R, and S156E). CD80-WT protein is used as a positive control and human IgG1 protein is a negative control.
Figure 22B:
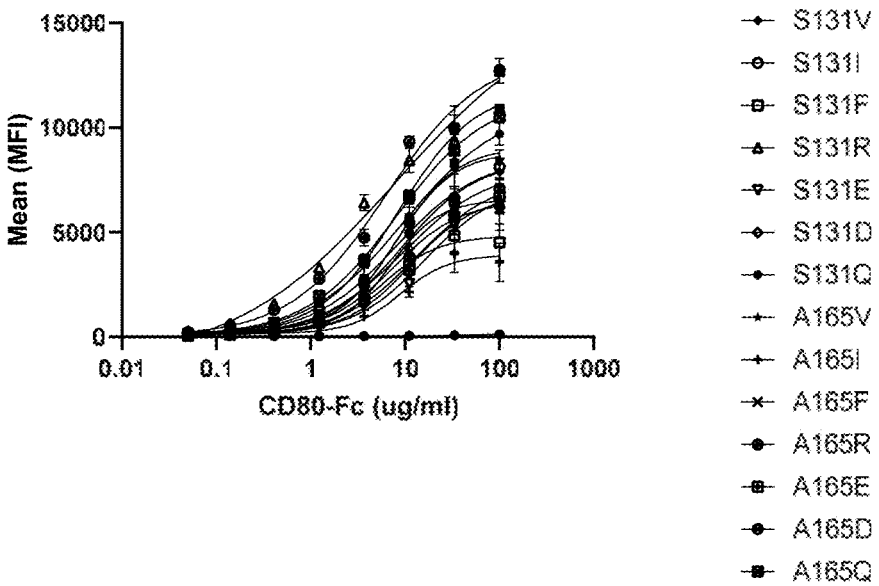
FIG. 22B depicts results of cell surface binding assays by FACS to test binding affinity of variant CD80-Fc Fusion Proteins to Flp-in 293 cells expressing PD-L1. Types of variant CD80 polypeptides tested herein are as follows: a single amino acid substitution/mutation at position at S156, S131, or A165 (S156D, S156Q, S131V, S131I, S131F, S131R, S131E, S131D, S131Q, A165V, A165I, A165F, A165R, A165E, A165D, and A165Q). CD80-WT protein is used as a positive control and human IgG1 protein is a negative control.
Figure 23A:
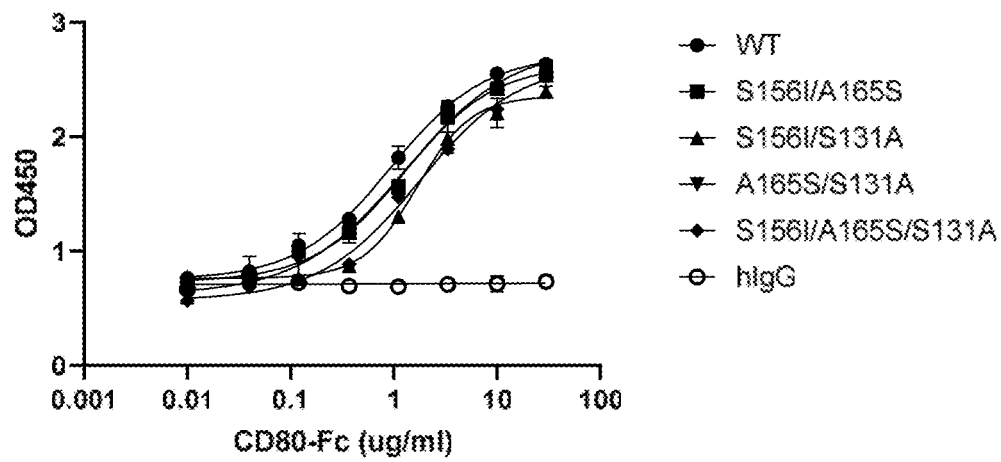
FIG. 23A depicts results of functional assays for IL-2 release to test ability of variant CD80-Fc Fusion Proteins for T-cell activation. Types of variant CD80 polypeptides tested herein are as follows: amino acid substitutions/mutations at two positions (S156I/A165S, S156I/S131A, and A165S/S131A—double substitutions/mutations), and three positions (S156I/A165S/S131A —triple substitutions/mutations). CD80-WT protein is used as a positive control and human IgG1 protein is a negative control.
Figure 23B:
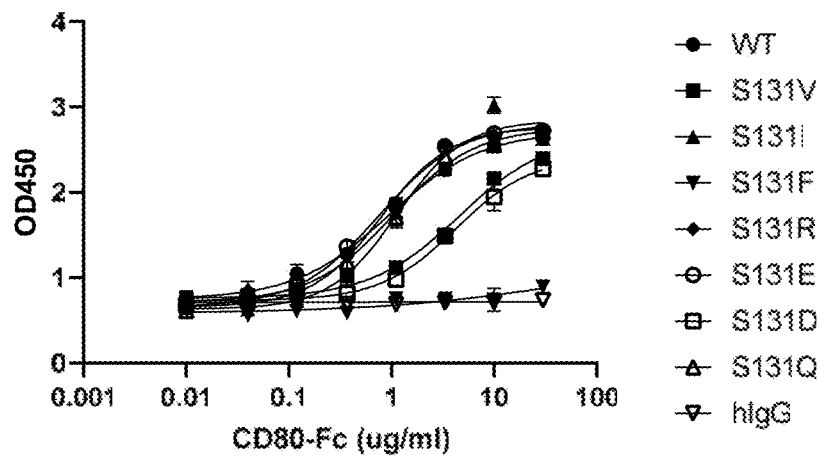
FIG. 23B depicts results of functional assays for IL-2 release to test ability of variant CD80-Fc Fusion Proteins for T-cell activation. Types of variant CD80 polypeptides tested herein are as follows: a single amino acid substitution/mutation at position S131 (S131V, S131I, S131F, S131R, S131E, S131D, and S131Q). CD80-WT protein is used as a positive control and human IgG1 protein is a negative control.
Figure 23C:
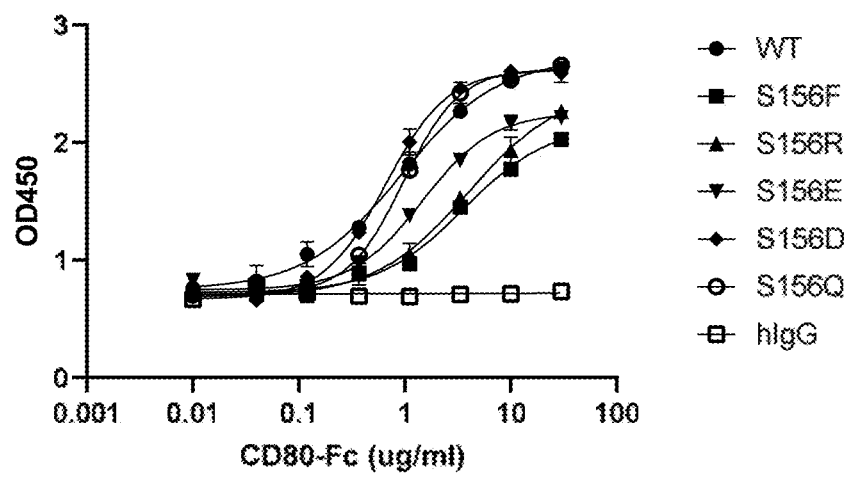
FIG. 23C depicts results of functional assays for IL-2 release to test ability of variant CD80-Fc Fusion Proteins for T-cell activation. Types of variant CD80 polypeptides tested herein are as follows: a single amino acid substitution/mutation at position S156 (S156F, S156R, S156E, S156D, and S156Q). CD80-WT protein is used as a positive control and human IgG1 protein is a negative control.
Figure 23D:
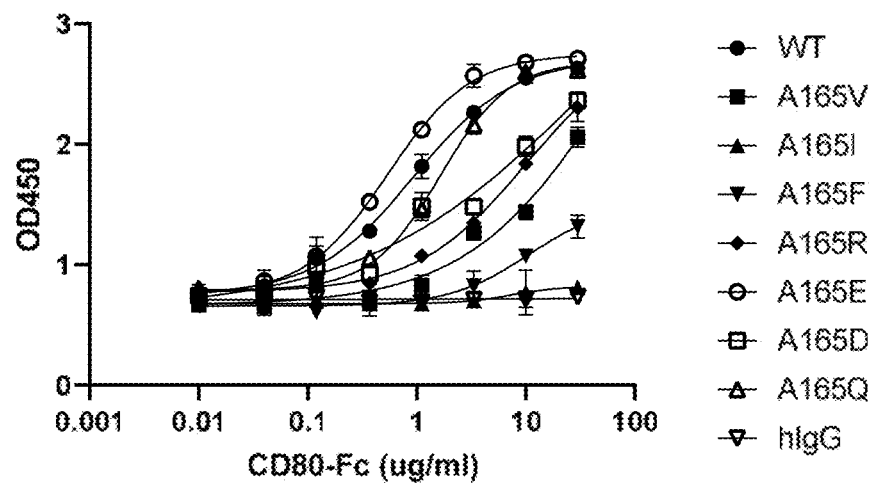
FIG. 23D depicts results of functional assays for IL-2 release to test ability of variant CD80-Fc Fusion Proteins for T-cell activation. Types of variant CD80 polypeptides tested herein are as follows: a single amino acid substitution/mutation at position A165 (A165V, A165I, A165F, A165R, A165E, A165D, and A165Q). CD80-WT protein is used as a positive control and human IgG1 protein is a negative control.

The results of cell surface binding affinity assays by FACS were presented in FIGS. 22A-22B (binding affinity of CD80 variants to PD-L1-overexpressing Flp-in 293 cells). Tables 14 and 15 summarize results of cell surface binding affinity assays presented in FIGS. 22A-22B with top MFI (Mean Fluorescence Intensity) values of each tested CD80-Fc Fusion protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay.

Figure 27:
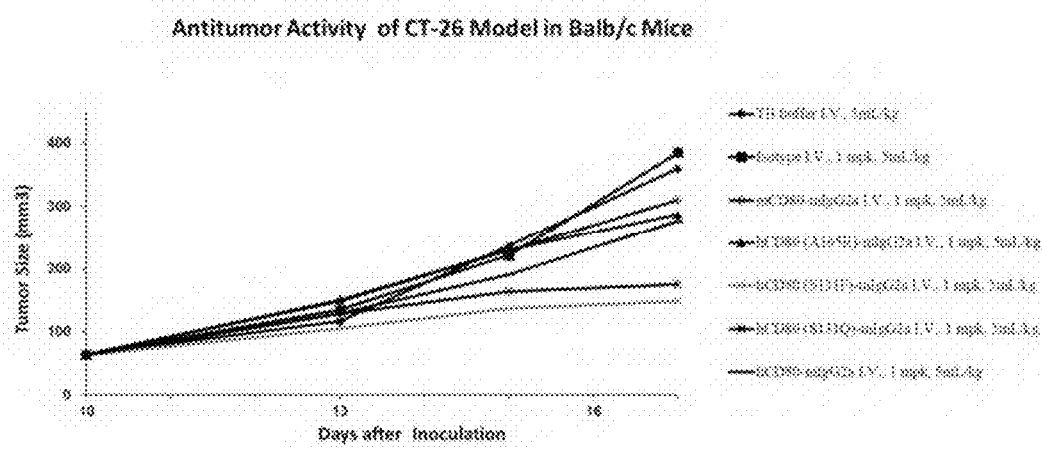

As seen in FIGS. 25-27, the FACS binding $EC_{50}$ of mutant CD80-Fc Fusion Proteins showed differentiation of binding affinity to CTLA-4, CD28 and PD-L1.

TABLE 12

|  | Top (MFI) | EC50 (ug/ml) |
| --- | --- | --- |
| WT | 12650 | 10 |
| S156I/A165S | 11348 | 9.2 |
| S156I/S131A | 10810 | 9.2 |
| A165S/S131A | 10150 | 6.3 |
| S156I/A165S/S131A | 10155 | 7.7 |
| S156F | 10700 | 9.2 |
| S156R | 9437 | 12.5 |
| S156E | 10252 | 9.8 |

TABLE 13

|  | Top (MFI) | EC50 (ug/ml) |
| --- | --- | --- |
| WT | 11800 | 8.5 |
| S156D | 11050 | 10.8 |
| S156Q | 10562 | 8.6 |
| S131V | 7493 | 11.4 |
| S131I | 8861 | 8.4 |
| S131F | 6007 | 15.9 |
| S131R | 10824 | 12.2 |
| S131E | 11296 | 7.9 |
| S131D | 9064 | 9.5 |
| S131Q | 10113 | 9.9 |
| A165V | 8281 | 15.2 |
| A165I | 4820 | 41.8 |
| A165F | 6674 | 18.7 |
| A165R | 7566 | 13.9 |
| A165E | 12093 | 10.7 |
| A165D | 8417 | 13.2 |
| A165Q | 8894 | 12.7 |

TABLE 15

|  | Top (MFI) | EC50 (ug/ml) |
| --- | --- | --- |
| WT | 11020 | 8.5 |
| S156D | 8379 | 8.3 |
| S156Q | 8323 | 8 |
| S131V | 7634 | 9.2 |
| S131I | 8699 | 8.1 |
| S131F | 3902 | 5.6 |
| S131R | 12302 | 8.1 |
| S131E | 6275 | 16.5 |
| S131D | 5994 | 11.5 |
| S131Q | 9317 | 9.9 |
| A165V | 6136 | 6.9 |
| A165I | 3622 | 8.9 |
| A165F | 6053 | 7.6 |
| A165R | 12635 | 6.3 |
| A165E | 6633 | 13.4 |
| A165D | 7152 | 9.4 |
| A165Q | 10717 | 8.3 |

TABLE 14

|  | Top (MFI) | EC50 (ug/ml) |
| --- | --- | --- |
| WT | 7361 | 3.9 |
| S156I/A165S | 7238 | 7.8 |
| S156I/S131A | 6830 | 4.3 |
| A165S/S131A | 7193 | 9.3 |
| S156I/A165S/S131A | 7981 | 6.7 |
| S156F | 7817 | 19.8 |
| S156R | 7921 | 5.8 |
| S156E | 8184 | 7.7 |

Example 4

Functional Study of CD80 Variants for T-Cell Activation
(1) IL-2 Release Assay

To test CD80-induced IL-2 production in Jurkat T-cells, IL-2 release assay was performed as follows: $3.2 \times 10^5$/well JurkaT-cells were seeded in a 96-well plate. Serial dilutions of each CD80 mutant protein were added to a final concentrations of 30 μg/ml, 10 μg/ml, 3 μg/ml, 1 μg/ml, 0.3 μg/ml, 0.1 μg/ml, 0.03 μg/ml and 0.01 μg/ml. PHA (phytohemagglutinin) was added to each well with final a concentration of 10 μg/ml. The cells were incubated at 37° C. for 24 hours and the supernatant were harvested for ELISA assay. The Human IL-2 Uncoated ELISA kit (Invitrogen #88-7025) was used to quantitate IL-2 in the supernatant. ELISA plate was coated with 50 μL/well of capture antibody overnight at 4° C. The plate was washed and blocked at room temperature for 1 hour. After washing, 50 μL/well of the above supernatant was added to the appropriate wells and incubated at room temperature for 2 hours. The plate was then washed and 50 μL/well of detection antibody was added and incubated at room temperature for 1 hour. After washing, 50 μL/well of Avidin-HRP was added and incubated at room temperature for 30 minutes. The plate was washed seven times and 50 μl of TMB Substrate was added to each well, and the reactions were stopped by addition of 25 μl of stop solution. $OD_{450}$ was measured using a microplate reader.

FIGS. 23A-23D presents results of functional assays for IL-2 release to test ability of variant CD80-Fc Fusion Proteins for T-cell activation. Table 16 summarizes results of T-cell activation assays measured by IL2 release presented in FIGS. 23A-23D with top OD450 values of each tested CD80-Fc Fusion protein including single, double and triple mutations (e.g. S156I/A165S, S156I/S131A, A165S/S131A, S156I/A165S/S131A, S156F, S156R, S156E, S156D, S156Q, S131V, S131I, S131F, S131R, S131E, S131D, S131Q, A165V, A165I, A165F, A165R, A165E, A165D, and A165Q), along with $EC_{50}$ (ug/ml) values. The $EC_{50}$ (ug/ml) is the concentration or value of a protein that gives half maximal response in the binding assay.

The results from JurkaT-cell IL-2 release assay as shown in FIGS. 23A-23D and presented in Table 16 indicate mutations in IgC domain can influence the ability of CD80 to activate T-cell.

TABLE 16

|  | Top (OD450) | EC50 (ug/ml) |
| --- | --- | --- |
| WT | 2.64 | 0.94 |
| S156I/A165S | 2.52 | 1.26 |
| S156I/S131A | 2.43 | 1.68 |
| A165S/S131A | 2.60 | 1.29 |

TABLE 16-continued

|  | Top (OD450) | EC50 (ug/ml) |
|---|---|---|
| S156I/A165S/S131A | 2.47 | 1.78 |
| S156F | 2.03 | 3.63 |
| S156R | 2.29 | 3.99 |
| S156E | 2.23 | 1.46 |
| S156D | 2.56 | 0.66 |
| S156Q | 2.66 | 0.97 |
| S131V | 2.40 | 4.59 |
| S131I | 2.61 | 1.13 |
| S131F | 0.90 | 66.84 |
| S131R | 2.71 | 0.79 |
| S131E | 2.72 | 0.76 |
| S131D | 2.26 | 4.27 |
| S131Q | 2.70 | 1.04 |
| A165V | 2.11 | 61.46 |
| A165I | 0.80 | 7.43 |
| A165F | 1.30 | 10.65 |
| A165R | 2.34 | 9.85 |
| A165E | 2.71 | 0.54 |
| A165D | 2.32 | 38.12 |
| A165Q | 2.61 | 1.65 |
| hIgG | 0.71 | — |

(2) Checkpoint Blockade Reporter Assays:

The CD80 variants were evaluated by checkpoint blockade reporter assay using Promega's assay kits. For CTLA-4 blockade assay, the CTLA-4/Jurkat Effector Cells and aAPC/Raji Cells were thawed at room temperature. Equilibrated the Bio-Glo™ Luciferase Assay Buffer to ambient temperature, protected from light. and then transferred all of the Bio-Glo™ Luciferase Assay Buffer into the amber bottle containing the Bio-Glo™ Luciferase Assay Substrate and mixed by inversion until the Substrate was thoroughly dissolved. Preparing and Plating CTLA-4 Effector Cells should be performed using aseptic technique in a sterile cell culture hood if setting up a 16-hour assay. For a 6-hour assay, the setup may be performed on the bench.

3.2 ml of prewarmed (37° C.) assay buffer was added to a 15 ml conical tube. One vial of CTLA-4 Effector Cells was removed from storage and transferred to the bench on dry ice. The cells were warmed in a 37° C. water bath until being just thawed (about 2-3 minutes). The cell suspension was gently mixed and the cells (0.8 ml) were transferred to the 15 ml conical tube containing 3.2 ml of assay buffer. After mixing well by gently inverting or pipetting 1-2 times, the cell suspension was transferred to a sterile reagent reservoir. Using a multichannel pipette, 25 μl of the cell suspension was immediately dispensed to each of the inner 60 wells of two 96-well, solid, white, flat-bottom assay plates. 75 μl of assay buffer was added to each of the outside wells of the assay plates. The assay plates were covered with a lid and keep at ambient temperature (22-25° C.).

Using a multichannel pipette, 25 μl of the appropriate antibody dilution was added to the plated CTLA-4 Effector Cells according to the plate. The assay plates were covered with a lid and are kept at ambient temperature (22°-25° C.) while preparing the aAPC/Raji Cells.

Preparing and Plating aAPC/Raji Cells

The thaw-and-use aAPC/Raji Cells included in this kit are sensitive, and care should be taken to follow the cell thawing and plating procedures exactly as described. The cell reagents should not be overmixed or overwarmed. 7.2 ml of prewarmed (37° C.) assay buffer was added to a 15 ml conical tube. One vial of aAPC/Raji Cells was removed from storage at −140° C. and transferred to the bench on dry ice. The cells were thawed in a 37° C. water bath until just thawed (about 2-3 minutes). The cells (0.8 ml) was transferred to the 15 ml conical tube containing 7.2 ml assay buffer. After mixing well by gently inverting or pipetting 1-2 times, the cell suspension was transferred to a sterile reagent reservoir. Using a multichannel pipette, 25 μl of the cell suspension was immediately dispensed to the pre-plated CTLA-4 Effector Cells and Anti-CTLA-4 Control Antibody. The final assay volume was 750 The assay plates were covered with a lid and incubate for 6 hours in a 37° C., 5% $CO_2$ incubator.

Note: The 6-hour assay time was optimized for maximum luminescence signal. Optimizing the assay time (6-16 hours) is recommended for optimal assay response. Plating CTLA-4 Effector Cells and aAPC/Raji Cells as indicated will result in a 2:1 ratio of Effector:Target cells. If higher luminescence signals are desired, the dilution volume of the aAPC/Raji Cells may be halved to attain a 1:1 ratio of Effector:Target cells.

Adding Bio-Glo™ Reagent

Bio-Glo™ Reagent should be at ambient temperature (22-25° C.) when added to assay plates. The assay plates were removed from the incubator and were equilibrated to ambient temperature for 10-15 minutes. Using a manual multichannel pipette, 75 μl of Bio-Glo™ Reagent was added to the inner 60 wells of the assay plates, taking care not to create bubbles. 75 μl of Bio-Glo™ Reagent was added to wells B1, C1 and D1 of each assay plate to measure the background signal and was incubated at ambient temperature for 5-15 minutes. Luminescence was measured using a luminometer luminescence plate reader.

FIGS. 25A-25L presents results of CTLA-4 blockade assay to evaluate the ability of variant CD80-Fc Fusion Proteins blocking CTLA-4/CD28 interaction function. Table 17 summarizes results of CTLA-4 blockade assay presented in FIGS. 25A-25L with $EC_{50}$ (ug/ml) values. The $EC_{50}$ (ug/ml) is the concentration or value of a protein that gives half maximal response in the binding assay.

TABLE 17

|  | EC50 (ug/mL) |
|---|---|
| WT | 0.243 |
| S156I/A165S | 0.217 |
| S156I/S131A | 0.309 |
| A165S/S131A | 0.868 |
| S156I/A165S/S131A | 0.227 |
| S156F | 1.187 |
| S156R | 0.361 |
| S156E | 0.363 |
| S156D | 0.474 |
| S156Q | 1.578 |
| S131V | 4.311 |
| S131I | 0.485 |
| S131F | 0.474 |
| S131R | 0.283 |
| S131E | 0.431 |
| S131D | 0.382 |
| S131Q | 0.209 |
| A165V | 0.296 |
| A165I | 2.432 |
| A165F | 0.323 |
| A165R | 0.227 |
| A165E | 1.039 |
| A165D | 0.210 |
| A165Q | 0.136 |
| S131V | 0.106 |
| V155A | 0.126 |
| V155I | 0.191 |
| V155T | 0.097 |
| V166A | 0.541 |
| V166T | 0.151 |
| V166L/L139V | 0.124 |

TABLE 17-continued

| | EC50 (ug/mL) |
|---|---|
| S156A/V155A | 0.250 |
| S156A/V155I | 0.118 |
| S156A/V155T | 0.036 |
| S156A/T130A | 0.121 |
| S156A/V166A | 0.281 |
| S156A/V166L/L139V | 0.187 |
| S156I | 0.134 |
| A165S | 0.168 |
| S156A | 0.311 |
| S131A | 0.187 |
| S156V | 0.134 |
| S156L | 0.168 |
| S156I | 0.311 |

Example 5

Co-Stimulation Activity of CD80 Variants

TCR/CD3 Effector (IL-2) cells (Promega) were used to evaluate co-stimulation activity of CD80 variants.

Briefly, TCR/CD3 effector (IL-2) cells were expanded freshly before the assay setup. TCR/CD3 effector (IL-2) cells were prepared at 2×10⁶ cells/mL in RPMI-1640 with 10% FBS. For one 96-well plate, 5 mL of cell suspension were added with 1 ug/mL of mouse anti-human CD3 antibody (OKT3, BioLeged Cat #317326) and 150 uL of goat anti-huIgG beads (AbraMag: Cat #PN544060). The mixture of cell, antibody and beads was distributed on an opaque 96-well plate at 50 uL/well. To prepare testing compounds, CD80-Fc wild-type (WT) and CD80-Fc variants, were prepared at 30 ug/mL and their duplicate 1:3 serial dilutions. 25 µl testing compounds were transferred to each well, with final volume of 75 µl/well on the plate. Blank wells were added with 75 µl of medium for measuring background readings. The plates were incubated at 37° C., 5% $CO_2$ incubator for 6 hours. After incubation, 75 µl of Bio-Glo™ Reagent (Promega) were added into each well of the assay plates, incubated at ambient temperature for 3 minutes. The Relative Luminescence Unit (RLU) readings were measured using a luminescence plate reader (CLARIOstar, BMG LABTECH).

The Relative Luminescence Unit (RLU) readings were plotted with GraphPad Prism® software and analyzed with program of [Agonist] vs. response—Variable slope (four parameters)—Least squares fit to determine the EC50 values.

FIGS. 26A-26H presents results of co-stimulation activity of variant CD80-Fc Fusion Proteins. Table 18 summarizes results presented in FIGS. 26A-26H with $EC_{50}$ (ug/ml) values. The $EC_{50}$ (ug/ml) is the concentration or value of a protein that gives half maximal response in the binding assay.

TABLE 18

| | EC50 (ug/ml) |
|---|---|
| CD80 (WT) | 0.4371 |
| S156I/A165S | 0.1501 |
| S156I/S131A | 0.1439 |
| A165S/S131A | 0.1876 |
| S156I/A165S/S131A | 0.1631 |
| S156F | 0.1596 |
| S156R | 0.2163 |
| S156E | 0.2038 |
| S156D | 0.2357 |
| S156Q | 0.2469 |
| S131V | 0.2515 |
| S131I | 0.2631 |
| S131F | 0.3372 |
| S131R | 0.3081 |
| S131E | 0.2341 |
| S131D | 0.2581 |
| S131Q | 0.1705 |
| A165V | 0.3016 |
| A165I | 0.4600 |
| A165F | 0.3154 |
| A165R | 0.1973 |
| A165E | 0.2215 |
| A165D | 0.1658 |
| A165Q | 0.1259 |
| S156A | 0.2442 |
| A165S | 0.1369 |
| S131A | 0.1450 |
| S156V | 0.1298 |
| S156L | 0.1023 |
| S131V | 0.1216 |
| V155A | 0.1239 |
| V155I | 0.1241 |
| V155T | 0.1718 |
| V166A | 0.2139 |
| V166T | 0.1839 |
| V166L/L139V | 0.1861 |
| S156A/V155A | 0.2243 |
| S156A/V155I | 0.1467 |
| S156A/V155T | 0.0643 |
| S156A/T130A | 0.1541 |
| S156A/V166A | 0.7127 |
| S156A/V166L/L139V | 0.1900 |
| S156I | 0.1259 |
| A165S | 0.0993 |

Example 6

In Vivo Efficacy Evaluation of Mutant CD80 in Tumor Growth (1) Inhibition in CT26 Syngeneic Mouse Model Efficacy evaluation of CD80 variants in tumor growth inhibition was tested in CT26 syngeneic mouse model. CT26 cells were inoculated subcutaneously into seven Balb/c mice at 1.0×10⁶ cells/mouse. Mice were monitored for tumor growth three times per week.

Mice were randomly assigned to different groups (n=7 mice per experimental group) when the mean tumor volume reached about 60-100 mm³. These tumor bearing mice were treated with CD80 variant at 1 mg/kg at day 0, day 3 and day 7 by intravenous injection. Tumors and body weights were measured three times per week to monitor the efficacy and toxicity.

FIG. 27 presents results of the antitumor activity of CD80 variants in CT26 syngeneic mouse model.

(2) Inhibition in MC-38 Syngeneic Mouse Model

Efficacy evaluation of CD80 variants in tumor growth inhibition was tested in MC-38 syngeneic mouse model. MC-38 cells were inoculated subcutaneously into seven C57BL/6 mice at 1.0×10⁶ cells/mouse. Mice were monitored for tumor growth twice per week.

Mice were randomly assigned to different groups (n=7 mice per experimental group) when the mean tumor volume reached about 90 mm³. These tumor bearing mice were treated with CD80 variant at 150 µg/mouse at day 1, day 4 and day 8 by intravenous injection. Tumors and body weights were measured twice per week to monitor the efficacy and toxicity.

Figure 28:
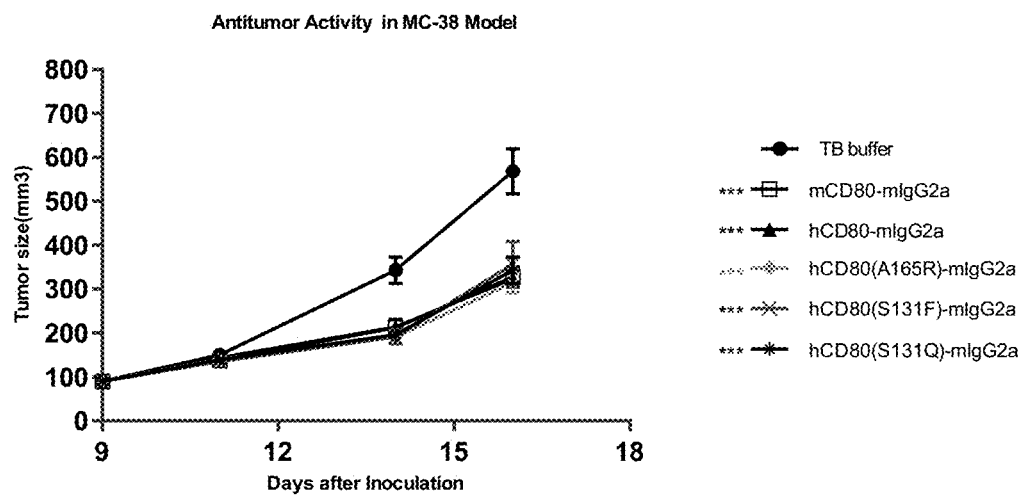
Figures 29A, 29B, 29C, 29D:
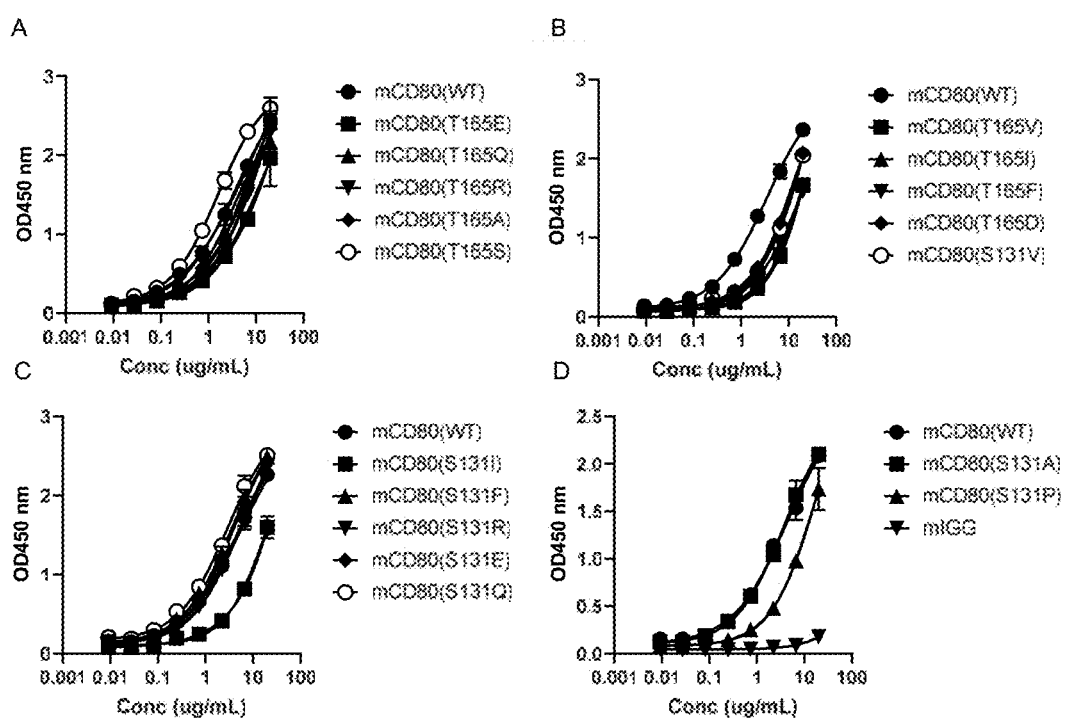
Figures 30A, 30B, 30C, 30D:
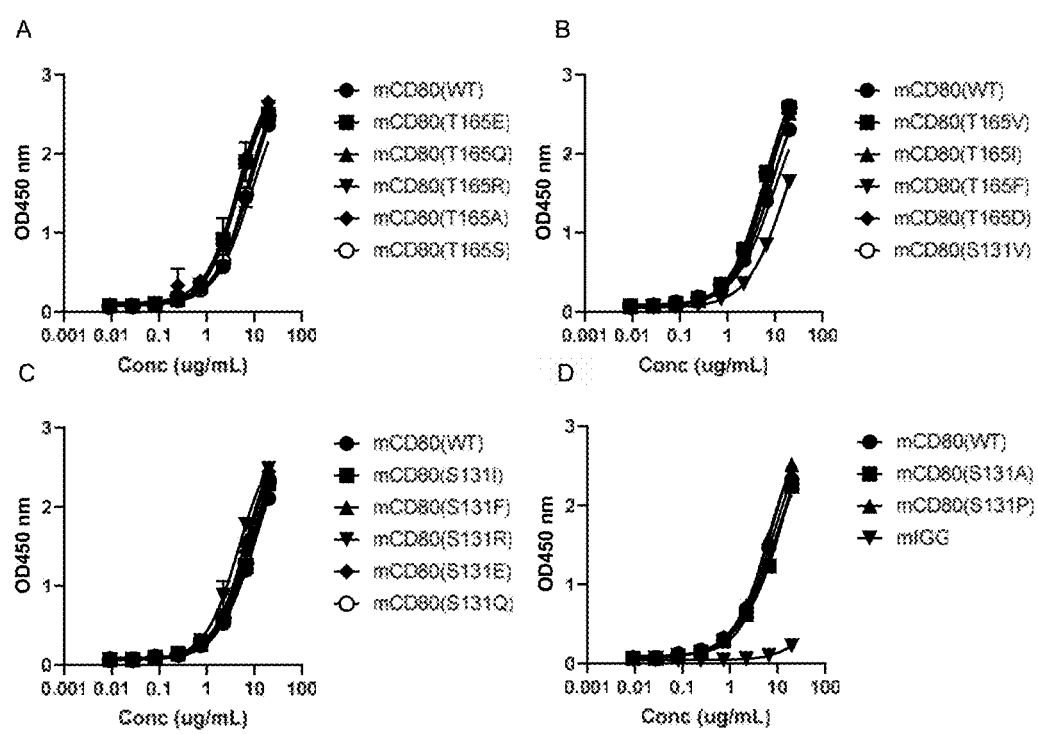
FIG. 30D depicts the binding assays by ELISA to test binding affinity of variant mouse CD80-Fc Fusion Proteins to immobilized binding partner mouse PD-L1. Types of variant mouse CD80 polypeptides tested herein are as follows: a single amino acid substitution/mutation at position S131 (S131A, and S131P). Mouse CD80-WT protein is used as a positive control.
Figures 31A, 31B, 31C, 31D:
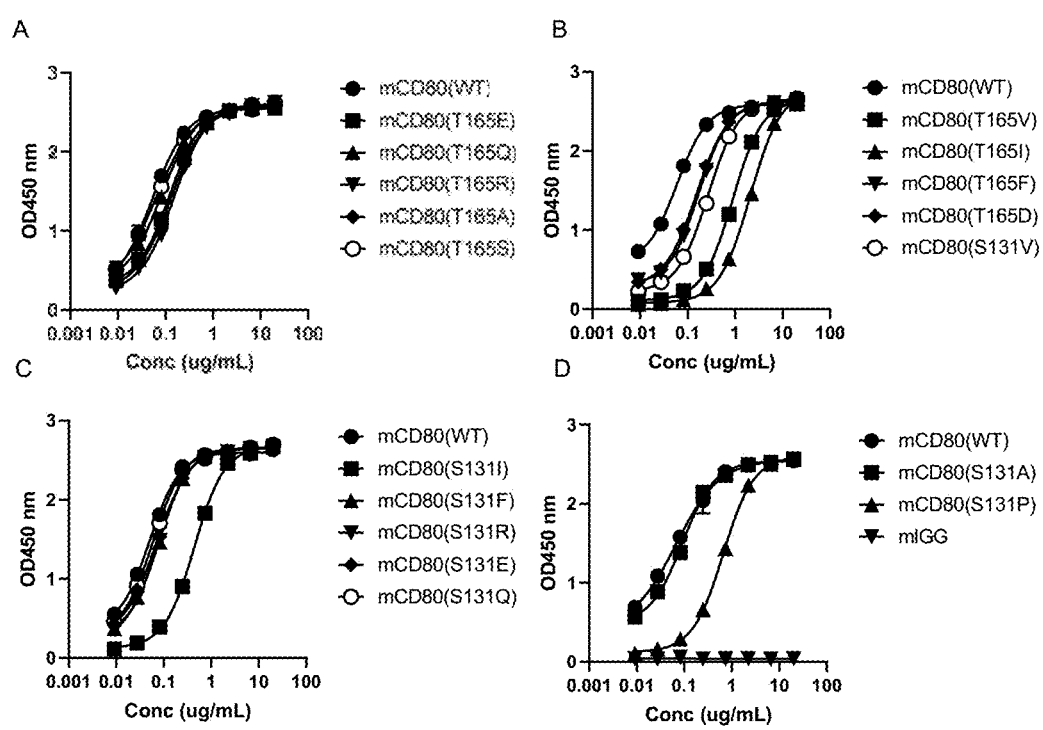
FIG. 31A depicts the binding assays by ELISA to test binding affinity of variant mouse CD80-Fc Fusion Proteins to immobilized binding partner mouse CTLA4. Types of variant mouse CD80 polypeptides tested herein are as follows: a single amino acid substitution/mutation at position T165 (T165E, T165Q, T165R, T165A, and T165S). Mouse CD80-WT protein is used as a positive control.
FIG. 31B depicts the binding assays by ELISA to test binding affinity of variant mouse CD80-Fc Fusion Proteins to immobilized binding partner mouse CTLA4. Types of variant mouse CD80 polypeptides tested herein are as follows: a single amino acid substitution/mutation at position T165 or S131 (T165V, T165I, T165F, T165D, and S131V). Mouse CD80-WT protein is used as a positive control.
FIG. 31C depicts the binding assays by ELISA to test binding affinity of variant mouse CD80-Fc Fusion Proteins to immobilized binding partner mouse CTLA4. Types of variant mouse CD80 polypeptides tested herein are as follows: a single amino acid substitution/mutation at position 5131 (S131I, S131F, S131R, S131E, and S131Q). Mouse CD80-WT protein is used as a positive control.
FIG. 31D depicts the binding assays by ELISA to test binding affinity of variant mouse CD80-Fc Fusion Proteins to immobilized binding partner mouse CTLA4. Types of variant mouse CD80 polypeptides tested herein are as follows: a single amino acid substitution/mutation at position S131 (S131A, and S131P). Mouse CD80-WT protein is used as a positive control.

FIGS. 28 presents results of the antitumor activity of CD80 variants in MC-38 syngeneic mouse model.

Example 7

Assessment of Binding Affinities of Mouse CD80 Variants to Mouse CD28, Mouse PD-L1, and Mouse CTLA-4 by ELISA The binding of mouse CD80 variants to mouse CD28, mouse PD-L1 and mouse CTLA-4, respectively, was ranked with wild-type mCD80 as reference sample tested on the same ELISA plate. This study is a surrogate for a human study. Variants of mouse CD80 are made, the wild type mouse CD80 is presented in FIG. 14B.

The results of binding affinity assays by ELISA were presented in FIGS. 29A-29D (binding affinity of mouse CD80 variants to mouse CD28). Table 19 summarizes results of binding assays presented in FIGS. 29A-29D with $EC_{50}$ (ug/ml) values of each tested mouse CD80-Fc Fusion protein including T165E, T165Q, T165R, T165A, T165S, T165V, T165I, T165F, T165D, S131V, S131I, S131F, S131R, S131E, S131Q, S131A, and S131P. The $EC_{50}$ (ug/ml) is the concentration or value of a protein that gives half maximal response in the binding assay.

The results of binding affinity assays by ELISA were presented in FIGS. 30A-30D (binding affinity of mouse CD80 variants to mouse PD-L1). Table 20 summarizes results of binding assays presented in FIGS. 30A-30D with $EC_{50}$ (ug/ml) values of each tested mouse CD80-Fc Fusion protein including T165E, T165Q, T165R, T165A, T165S, T165V, T165I, T165F, T165D, S131V, S131I, S131F, S131R, S131E, S131Q, S131A, and S131P. The $EC_{50}$ (ug/ml) is the concentration or value of a protein that gives half maximal response in the binding assay.

The results of binding affinity assays by ELISA were presented in FIGS. 31A-31D (binding affinity of mouse CD80 variants to mouse CTLA4). Table 21 summarizes results of binding assays presented in FIGS. 31A-31D with $EC_{50}$ (ug/ml) values of each tested mouse CD80-Fc Fusion protein including T165E, T165Q, T165R, T165A, T165S, T165V, T165I, T165F, T165D, S131V, S131I, S131F, S131R, S131E, S131Q, S131A, and S131P. The $EC_{50}$ (ug/ml) is the concentration or value of a protein that gives half maximal response in the binding assay.

TABLE 19

| | EC50 |
|---|---|
| A. mCD80(WT) | 3.606 |
| mCD80(T165E) | 10.59 |
| mCD80(T165Q) | 3.462 |
| mCD80(T165R) | 6.914 |
| mCD80(T165A) | 5.705 |
| mCD80(T165S) | 1.603 |
| B. mCD80(WT) | 3.499 |
| mCD80(T165V) | 17.56 |
| mCD80(T165I) | 17.69 |
| mCD80(T165F) | 18.27 |
| mCD80(T165D) | 10.37 |
| mCD80(S131V) | 11.19 |
| C. mCD80(WT) | 5.467 |
| mCD80(S131I) | 19.25 |
| mCD80(S131F) | 3.485 |
| mCD80(S131R) | 5.127 |
| mCD80(S131E) | 3.755 |
| mCD80(S131Q) | 2.879 |
| D. mCD80(WT) | 4.343 |
| mCD80(S131A) | 3.709 |
| mCD80(S131P) | 15.3 |

TABLE 20

| | EC50 |
|---|---|
| A. mCD80(WT) | 8.987 |
| mCD80(T165E) | 3.865 |
| mCD80(T165Q) | 4.261 |
| mCD80(T165R) | 4.97 |
| mCD80(T165A) | 4.795 |
| mCD80(T165S) | 6.856 |
| B. mCD80(WT) | 9.688 |
| mCD80(T165V) | 5.873 |
| mCD80(T165I) | 7.567 |
| mCD80(T165F) | 17.13 |
| mCD80(T165D) | 5.879 |
| mCD80(S131V) | 6.079 |
| C. mCD80(WT) | 9.914 |
| mCD80(S131I) | 8.58 |
| mCD80(S131F) | 7.044 |
| mCD80(S131R) | 4.661 |
| mCD80(S131E) | 9.23 |
| mCD80(S131Q) | 8.217 |
| D. mCD80(WT) | 8.698 |
| mCD80(S131A) | 8.801 |
| mCD80(S131P) | 6.098 |

TABLE 21

| | EC50 |
|---|---|
| A. mCD80(WT) | 0.0535 |
| mCD80(T165E) | 0.1206 |
| mCD80(T165Q) | 0.0827 |
| mCD80(T165R) | 0.1502 |
| mCD80(T165A) | 0.1313 |
| mCD80(T165S) | 0.0633 |
| B. mCD80(WT) | 0.0598 |
| mCD80(T165V) | 0.8854 |
| mCD80(T165I) | 2.079 |
| mCD80(T165F) | 0.172 |
| mCD80(T165D) | 0.1538 |
| mCD80(S131V) | 0.2691 |
| C. mCD80(WT) | 0.0508 |
| mCD80(S131I) | 0.4419 |
| mCD80(S131F) | 0.0782 |
| mCD80(S131R) | 0.0748 |
| mCD80(S131E) | 0.0713 |
| mCD80(S131Q) | 0.0596 |
| D. mCD80(WT) | 0.0673 |
| mCD80(S131A) | 0.0924 |
| mCD80(S131P) | 0.6586 |

Example 8

In Vivo Efficacy Evaluation of Mouse CD80 Variants in Tumor Growth

Efficacy evaluation of CD80 variants on tumor growth inhibition can be tested in a CT26 or MC-38 syngeneic mouse model. To test, a mouse CD80 protein is used, as a surrogate for the human protein. To test, CT26 or MC-38 cells are inoculated subcutaneously into mice at $1.0 \times 10^6$ cells/mouse. Mice are monitored for tumor growth three times per week.

Mice are randomly assigned to different groups (e.g. n=7 mice per experimental group) when the mean tumor volume reaches about 100 mm³. These tumor bearing mice are treated with a mouse CD80 variant at 1 mg/kg at day 0, day 3 and day 7 by intravenous injection. Tumors and body weights are measured three times per week to monitor the efficacy and toxicity.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

What is claimed is:

1. A variant CD80 polypeptide comprising amino acid substitution mutations in SEQ ID NO:1, wherein the amino acid substitution mutations are:
   1) S131A, S156I and A165S;
   2) S131A and S156I; or
   3) S131A and A165S;
   wherein the variant CD80 polypeptide further comprises a second polypeptide capable of dimerizing; and wherein the second polypeptide is an immunoglobulin Fc domain.

2. The variant CD80 polypeptide according to claim 1, wherein the immunoglobulin Fc domain is:
   (1) a human IgG1 Fc domain, a human IgG2 Fc domain, a human IgG3 Fc domain, or a human IgG4 Fc domain; or (2) a mouse IgG1 Fc domain, a mouse IgG2a Fc domain, a mouse IgG2b Fc domain, or a mouse IgG3 Fc domain.

3. The variant CD80 polypeptide according to claim 1, wherein the immunoglobulin Fc domain is a human IgG1 Fc domain.

4. A polynucleotide encoding the variant CD80 polypeptide according to claim 1, wherein the polynucleotide is a synthetic nucleic acid.

5. The polynucleotide according to claim 4, wherein the polynucleotide is operably linked to a transcriptional control element, and the transcriptional control element is a promoter that is functional in a eukaryotic cell.

6. A pharmaceutical composition comprising the variant CD80 polypeptide according to claim 1, wherein the pharmaceutical composition further comprises a pharmaceutically acceptable excipient.

7. A method of modulating an immune response and/or treating a disease or condition in a subject, wherein the method comprises administering to the subject the variant CD80 polypeptide according to claim 1 or the polynucleotide of claim 4, or the pharmaceutical composition of claim 6.

8. The method according to claim 7, wherein the disease or condition is a tumor or cancer; or an autoimmune disease.

9. The method according to claim 8, wherein the tumor or cancer is selected from melanoma, lung cancer, bladder cancer, hematological malignancy, liver cancer, brain cancer, renal cancer, breast cancer, pancreatic cancer, colorectal cancer, spleen cancer, prostate cancer, testicular cancer, ovarian cancer, uterine cancer, gastric carcinoma, musculoskeletal cancer, head and neck cancer, gastrointestinal cancer, germ cell cancer, endocrine cancer, and neuroendocrine cancer.

10. The method according to claim 8, wherein the autoimmune disease is selected from an autoimmune disease resulting from transplantation, Crohn's disease, multiple sclerosis, asthma, rheumatoid arthritis, autoimmune skin disease, rheumatic disease, autoimmune hematological disease, and psoriasis.

* * * * *